US006869789B2

(12) United States Patent
Liu et al.

(10) Patent No.: US 6,869,789 B2
(45) Date of Patent: Mar. 22, 2005

(54) HEPARINASE III AND USES THEREOF

(75) Inventors: Dongfang Liu, Westborough, MA (US);
Kevin Pojasek, Boston, MA (US);
Zachary Shriver, Boston, MA (US);
Kristine Holley, Boston, MA (US);
Yosuf El-Shabrawi, Graz (AT);
Ganesh Venkataraman, Waltham, MA (US); Ram Sasisekharan, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/802,285

(22) Filed: Mar. 8, 2001

(65) Prior Publication Data

US 2002/0122793 A1 Sep. 5, 2002

Related U.S. Application Data

(60) Provisional application No. 60/187,846, filed on Mar. 8, 2000.

(51) Int. Cl.$^7$ .............................. C12N 9/64; C07K 1/00

(52) U.S. Cl. ...................................... 435/232; 530/811

(58) Field of Search .......................... 435/232; 530/811

(56) References Cited

U.S. PATENT DOCUMENTS

| | | | |
|---|---|---|---|
| 4,281,108 A | 7/1981 | Fussi |
| 4,341,869 A | 7/1982 | Langer, Jr. et al. |
| 4,373,023 A | 2/1983 | Langer et al. |
| 4,396,762 A | 8/1983 | Langer et al. |
| 4,443,545 A | 4/1984 | Langer, Jr. et al. |
| 4,551,296 A | 11/1985 | Kavesh et al. |
| 4,679,555 A | 7/1987 | Sackner |
| 4,745,105 A | 5/1988 | Griffin et al. |
| 4,757,056 A | 7/1988 | Van Gorp et al. |
| 4,830,013 A | 5/1989 | Maxwell |
| 4,928,694 A | 5/1990 | Maxwell |
| 4,942,156 A | 7/1990 | Foley et al. |
| 4,990,502 A | 2/1991 | Lormeau et al. |
| 5,010,063 A | 4/1991 | Piani et al. |
| 5,039,529 A | 8/1991 | Bergendal et al. |
| 5,106,734 A | 4/1992 | Nielsen |
| 5,152,784 A | 10/1992 | Tsilibary |
| 5,164,378 A | 11/1992 | Conti et al. |
| 5,169,772 A | 12/1992 | Zimmerman et al. |
| 5,204,323 A | 4/1993 | Findlay et al. |
| 5,252,339 A | 10/1993 | Cristofori et al. |
| 5,262,325 A | 11/1993 | Zimmermann et al. |
| 5,290,695 A | 3/1994 | Morikawa et al. |
| 5,338,677 A | 8/1994 | Zimmermann et al. |
| 5,389,539 A | 2/1995 | Sasisekharan et al. |
| 5,453,171 A | 9/1995 | Ma et al. |
| 5,474,987 A | 12/1995 | Cohen et al. |
| 5,567,417 A | 10/1996 | Sasisekharan et al. |
| 5,569,366 A | 10/1996 | Chen et al. |
| 5,569,600 A | 10/1996 | Sasisekharan et al. |
| 5,576,304 A | 11/1996 | Kakkar et al. |
| 5,599,801 A | 2/1997 | Branellec et al. |
| 5,607,859 A | 3/1997 | Biemann et al. |
| 5,618,917 A | 4/1997 | Toback et al. |
| 5,619,421 A | 4/1997 | Venkataraman et al. |
| 5,681,733 A | 10/1997 | Su et al. |
| 5,687,090 A | 11/1997 | Chen et al. |
| 5,714,376 A | 2/1998 | Sasisekharan et al. |
| 5,744,515 A | 4/1998 | Clapper |
| 5,752,019 A | 5/1998 | Rigoutsos et al. |
| 5,753,445 A | 5/1998 | Fillit et al. |
| 5,759,767 A | 6/1998 | Lakowicz et al. |
| 5,763,427 A | 6/1998 | Weitz et al. |
| 5,767,269 A | 6/1998 | Hirsh et al. |
| 5,776,434 A | 7/1998 | Purewal et al. |
| 5,795,875 A | 8/1998 | Holme et al. |
| 5,808,021 A | 9/1998 | Holme et al. |
| 5,824,299 A | 10/1998 | Luster et al. |
| 5,830,726 A | 11/1998 | Sasisekharan et al. |
| 5,855,913 A | 1/1999 | Hanes et al. |
| 5,856,928 A | 1/1999 | Yan |
| 5,874,064 A | 2/1999 | Edwards et al. |
| 5,879,713 A | 3/1999 | Roth et al. |
| 5,919,693 A | 7/1999 | Su et al. |
| 5,922,358 A | 7/1999 | Doutremepuich et al. |
| 5,952,653 A | 9/1999 | Covey et al. |

(List continued on next page.)

FOREIGN PATENT DOCUMENTS

| | | |
|---|---|---|
| EP | 0 140 781 A2 | 5/1985 |
| EP | 0 114 589 B1 | 9/1987 |
| EP | 0 244 236 A2 | 11/1987 |

(List continued on next page.)

OTHER PUBLICATIONS

Wishart et al, A single mutation converts a novel phosphotyrosine binding domain into a dual–specificity phosphatase. J Biol Chem. Nov. 10, 1995;270(45):26782–5.*

Witkowski et al, Conversion of a beta–ketoacyl synthase to a malonyl decarboxylase by replacement of the active–site cysteine with glutamine. Biochemistry. Sep. 7, 1999;38(36):11643–50.*

DL Lohse and RJ Linhardt Purification and characterization of heparin lyases from *Flavobacterium heparinum* J. Biol. Chem. 1992 267:24347–24355.*

(List continued on next page.)

*Primary Examiner*—Rebecca E. Prouty
*Assistant Examiner*—Sheridan L. Swope
(74) *Attorney, Agent, or Firm*—Wolf, Greenfield & Sacks, P.C.

(57) ABSTRACT

The invention relates to heparinase III and mutants thereof. Modified forms of heparinase III having reduced enzymatic activity which are useful for a variety of purposes, including sequencing of heparin-like glycosaminoglycans (HLGAGs), removing active heparan sulfate from a solution, inhibition of angiogenesis, etc. have been discovered according to the invention. The invention in other aspects relates to methods of treating cancer and inhibiting tumor cell growth and/or metastasis using heparinase III, or products produced by enzymatic cleavage by heparinase III of HLGAGs.

10 Claims, 17 Drawing Sheets

U.S. PATENT DOCUMENTS

| | | | |
|---|---|---|---|
| 5,968,822 | A | 10/1999 | Pecker et al. |
| 5,985,309 | A | 11/1999 | Edwards et al. |
| 5,990,097 | A | 11/1999 | Kennedy |
| 5,993,846 | A | 11/1999 | Friedman et al. |
| 5,997,863 | A | 12/1999 | Zimmermann et al. |
| 6,013,628 | A | 1/2000 | Skubitz et al. |
| 6,116,237 | A | 9/2000 | Schultz et al. |
| 6,136,295 | A | 10/2000 | Edwards et al. |
| 6,190,875 | B1 | 2/2001 | Ben-Artzi et al. |
| 6,217,863 | B1 | 4/2001 | Godavarti et al. |
| 6,268,146 | B1 | 7/2001 | Shultz et al. |
| 6,291,439 | B1 | 9/2001 | Klock |
| 6,309,853 | B1 | 10/2001 | Friedman et al. |
| 6,333,051 | B1 | 12/2001 | Kabanov et al. |
| 6,597,996 | B1 | 7/2003 | Venkataraman et al. |

FOREIGN PATENT DOCUMENTS

| | | | |
|---|---|---|---|
| EP | 0 394 971 A1 | 10/1990 | |
| EP | 0 433 225 A1 | 6/1991 | |
| EP | 0 342 215 B1 | 8/1993 | |
| EP | 0 557 887 A2 | 9/1993 | |
| WO | WO 92/01003 A1 | 1/1992 | |
| WO | WO 93/05167 A1 | 3/1993 | |
| WO | WO 93/08289 A1 | 4/1993 | |
| WO | WO 93/10450 | 5/1993 | |
| WO | WO 93/15406 | 8/1993 | |
| WO | WO 93/19096 A1 | 9/1993 | |
| WO | WO 93/19734 | 10/1993 | |
| WO | WO 94/12618 A1 | 6/1994 | |
| WO | WO 94/21689 A1 | 9/1994 | |
| WO | WO 95/13830 A1 | 5/1995 | |
| WO | WO 95/34635 A1 | 12/1995 | |
| WO | WO 96/01648 A1 | 1/1996 | |
| WO | WO 96/32149 | 10/1996 | |
| WO | WO 97/06783 | 2/1997 | |
| WO | WO 97/11684 * | 4/1997 | A61K/9/14 |
| WO | WO 97/16556 A1 | 5/1997 | |
| WO | WO 97/35562 | 10/1997 | |
| WO | WO 98/04902 | 2/1998 | |
| WO | WO 98/31346 | 7/1998 | |
| WO | WO 00/12726 A2 | 3/2000 | |
| WO | WO 00/65521 A2 | 11/2000 | |

OTHER PUBLICATIONS

Alderman, C.P. et al., "Continuous Subcutaneous Heparin Infusion for Treatment of Trousseau's Syndrome", *The Annals of Pharmacotherapy*, Jul./Aug. 1995, pp. 710–713, vol. 29.

Baumann, U. et al., "Three–dimensional structure of the alkaline protease of *Pseudomonas aeruginosa*: a two–domain protein with a calcium binding parallel beta roll motif", *The EMBO Journal*, 1993, pp. 3357–3364, vol. 12, No. 9.

Bernstein, H. et al., "Immobilized Heparin Lyase System for Blood Deheparinization", *Methods in Enzymology*, 1988, pp. 515–529, vol. 137, Academic Press, Inc.

Cardin, A.D. et al., "Molecular Modeling of Protein–Glycosaminglycan Interactions", *Arteriosclerosis*, Jan./Feb. 1989, pp. 21–32, vol. 9, No. 1.

Cohen, F.E., "The Parallel β Helix of Pectate Lyase C: Something to Sneeze At", *Science*, Jun. 4, 1993, pp. 1444–1445, vol. 260.

Comfort, A.R. et al., "Immobilized Enzyme Cellulose Hollow Fibers: III. Physical Properties and In Vitro Biocompatibility", *Biotechnology and Bioengineering*, 1989, pp. 1383–1390, vol. 34, John Wiley & Sons, Inc.

Enriquez–Harris, P. et al., "Growth factors and the extracellular matrix", *Meeting Report, Trends in Cell Biology*, 1994, 2 Pages.

Ernst, S. et al., "Direct evidence for a predominantly exolytic processive mechanism for depolymerization of heparin–like glycosaminoglycans by heparinase I", *Proc. Natl. Acad. Sci. USA*, Apr. 1998, pp. 4182–4187, vol. 95, Biochemistry.

Feingold, D.S. et al., "Conformational aspects of the reaction mechanisms of polysaccharide lyases and epimerases", *FEB Letters*, Nov. 1987, pp. 207–211, vol. 223, No. 2, Elsevier Science Publishers B.V.

Franklin, M.J. et al., "*Pseudomonas aeruginosa* AlgG is a Polymer Level Alginate C5–Mannuronan Epimerase", *Journal of Bacteriology*, Apr. 1994, pp. 1821–1830, vol. 176, No. 7, American Society for Microbiology.

Gacesa, P., "*Hypothesis* Alginate–modifying enzymes, A proposed unified mechanism of action for the lyases and epimerases", *FEB Letters*, Feb. 1987, pp. 199–202, vol. 212, No. 2, Elsevier Science Publishers B.V.

Godavarti, R. et al., "Heparinase I from *Flavobacterium heparinum*. Identification of a Critical Histidine Residue Essential for Catalysis as Probed by Chemical Modification and Site–Directed Mutagenesis", *Biochemistry*, 1996, pp. 6846–6852, vol. 35, No. 21, American Chemical Society.

Godavarti, R. et al., "Heparinase III for *Flavobacterium heparinum*: cloning and recombinant expression in *Escherichia coli*", *Biochem. Biophys. Res. Commun.*, Aug. 23, 1996, pp. 751–758, vol. 225, No. 3, Academic Press, Inc.

Godavarti, R. et al., "A comparative analysis of the primary sequences and characteristics of heparinases I, II, and III from *Flavobacterium heparinum*", *Biochem. Biophys. Res. Commun.*, Dec. 24, 1996, pp. 770–777, vol. 229, No. 3, Academic Press, Inc.

Hart, G.W., "Glycosylation", *Current Opinion in Cell Biology*, 1992, pp. 1017–1023, vol. 4.

Higuchi, R., "Recombinant PCR", *PCR Protocols: A Guide to Methods and Applications*, 1990, pp. 177–183, Academic Press, Inc.

Huang, J.N. et al., "Low–Molecular–Weight Heparins", *Hematology/Oncology Clinics of North America*, Dec. 1998, pp. 1251–1281, vol. 12, No. 6.

Jackson, R.L. et al., "Glycosaminoglycans: Molecular Properties, Protein Interactions, and Role in Physiological Processes", *Physiological Reviews*, Apr. 1991, pp. 481–539, vol. 71, No. 2, The American Physiological Society.

Kakkar, A.K. et al., "Venous thromboembolism and cancer", *Baillier's Clinical Haematology*, Sep. 1998, pp. 675–687, vol. 11, No. 3, Bailliere Tindall.

Kretsinger, R.H. et al., "Structure and Evolution of Calcium–Modulated Proteins", *CRC Critical Reviews in Biochemistry*, Jul. 1980, pp. 119–174, vol. 8, No. 2.

Leckband, D. et al., "An Approach for the Stable Immobilization of Proteins", *Biotechnology and Bioengineering*, 1991, pp. 227–237, vol. 37, John Wiley & Sons, Inc.

Lewin, B., "Cells Obey the Laws of Physics and Chemistry", *Genes V*, 1994, p. 13, Oxford University Press.

Linhardt, R.J. et al., "Polysaccharide Lyases", *Applied Biochemistry and Biotechnology*, 1986, pp. 135–176, vol. 12.

Linhardt, R.J. et al., "Examination of the Substrate Specificity of Heparin and Heparan Sulfate Lyases", *Biochemistry*, 1990, pp. 2611–2617, vol. 29, No. 10, American Chemical Society.

Linhardt, R.J. et al., "Production and Chemical Processing of Low Molecular Weight Heparins", *Seminars in Thrombosis and Hemostatis*, 1999, pp. 5–16, vol. 25, Suppl. No. 3, Thiemo Medical Publishers, Inc.

Liu, D. et al., "The Calcium–binding Sites of Heparinase I from *Flavobacterium heparinum* are Essential for Enzymatic Activity", *The Journal of Biological Chemistry*, Feb. 12, 1999, pp. 4089–4095, vol. 274, No. 7, The American Society for Biochemistry and Molecular Biology, Inc.

Liu, J. et al., "Heparan Sulfate D–Glucosaminyl 3–0–Sulfotransferase–3A Sulfates N–Unsubstituted Glucosamine Residues", *The Journal of Biological Chemistry*, Dec. 31, 1999, pp. 38155–38162, vol. 274, No. 53, The American Society for Biochemistry and Molecular Biology, Inc.

Lohse, D.L. et al., "Purification and Characterization of Heparin Lyases from *Flavobacterium heparinum*", *The Journal of Biological Chemistry*, Dec. 5, 1992, pp. 24347–24355, vol. 267, No. 34, The American Society for Biochemistry and Molecular Biology, Inc.

Lustig, F. et al., "Alternative Splicing Determines the Binding of Platelet–Derived Growth Factor (PDGF–AA) to Glycosaminoglycans", *Biochemistry*, 1996, pp. 12077–12085, vol. 35, No. 37, American Chemical Society.

Pojasek, K. et al., "Histidine 295 and histidine 510 are crucial for the enzymatic degradation of heparan sulfate by heparinase III", *Biochemistry*, Apr. 11, 2000, pp. 4012–4019, vol. 39, No. 14, American Chemistry Society.

Rhomberg, A.J. et al., "Mass spectrometric and capillary electrophoretic investigation of the enzymatic degradation of heparin–like glycosaminoglycans", *Proc. Natl. Acad. Sci. USA*, Apr. 1998, pp. 4176–4181, vol. 95, Biochemistry.

Rhomberg, A.J. et al., "Mass spectrometric evidence for the enzymatic mechanism of the depolymerization of heparin–like glycosaminoglycans by heparinase II", *Proc. Natl. Acad. Sci. USA*, Oct. 1998, pp. 12232–12237, vol. 95, Biochemistry.

Sasisekharan, R. et al., "Cloning and expression of heparinase I gene from *Flavobacterium heparinum*", *Proc. Natl. Acad. Sci. USA*, Apr. 1993, pp. 3660–3664, vol. 90, Applied Biological Sciences.

Sasisekharan, R. et al., "Heparinase inhibits neovascularization", *Proc. Natl. Acad. Sci. USA*, Feb. 1994, pp. 1524–1528, vol. 91, Cell Biology.

Sasisekharan, R. et al., "Heparinase I from *Flavobacterium heparinum*: The Role of the Cysteine Residue in Catalysis as Probed by Chemical Modification and Site–Directed Mutagenesis", *Biochemistry*, 1995, pp. 14441–14448, vol. 34, No. 44, American Chemical Society.

Sasisekharan, R. et al., "Heparinase I from *Flavobacterium heparinum*, Mapping and Characterization of the Heparin Binding Domain", *The Journal of Biological Chemistry*, Feb. 9, 1996, pp. 3124–3131, vol. 271, No. 6, The American Society for Biochemistry and Molecular Biology, Inc.

Sasisekharan, R. et al., "Heparin and heparan sulfate: biosynthesis, structure and function", *Curr. Opin. Chem. Biol.*, Dec. 2000, pp. 626–631, vol. 4, No. 6, The American Society for Biochemistry and Molecular Biology, Inc.

Shriver, Z. et al., "Heparinase II from *Flavobacterium heparinum*, Role of Histidine Residues in Enzymatic Activity as Probed by Chemical Modification and Site–Directed Mutagenesis", *The Journal of Biological Chemistry*, Apr. 24, 1998, pp. 10160–10167, vol. 273, No. 17, The American Society for Biochemistry and Molecular Biology, Inc.

Shriver, Z. et al., "Heparinase II from *Flavobacterium heparinum*, Role of cysteine in Enzymatic Activity as Probed by Chemical Modification and Site–Directed Mutagenesis", *The Journal of Biological Chemistry*, Sep. 4, 1998, pp. 22904–22912, vol. 273, No. 36, The American Society for Biochemistry and Molecular Biology, Inc.

Shriver, Z. et al., "Biochemical Investigations and Mapping of the Calcium–binding Sites of Heparinase I from *Flavobacterium heparinum*", *The Journal of Biological Chemistry*, Feb. 12, 1999, pp. 4082–4088, vol. 274, No. 7, The American Society for Biochemistry and Molecular Biology, Inc.

Shriver, Z. et al., "Sequencing of 3–0 sulfate containing heparin decasaccharides with a partial antithrombin III binding site", *Proc. Natl. Acad. Sci. USA*, Sep. 12, 2000, pp. 10359–10364, vol. 97, No. 19.

Shriver, Z. et al., "Cleavage of the antithrombin III binding site in heparin by heparinases and its implication in the generation of low molecular weight heparin", *Proc. Natl. Acad. Sci. USA*, Sep. 12, 2000, pp. 10365–10370, vol. 97, No. 19.

Valentine, K.A. et al., "Low–Molecular–Weight Heparin Therapy and Mortality", *Seminars in Thrombosis and Hemostatis*, 1997, pp. 173–178, vol. 23, No. 2, Thieme Medical Publishers, Inc.

Venkataraman, G. et al., "Sequencing complex polysaccharides", *Science*, Oct. 15, 1999, pp. 537–542, vol. 286(5439).

Yang, V.C. et al., "Purification and Characterization of Heparinase from *Flavobacterium heparinum*", *The Journal of Biological Chemistry*, Feb. 10, 1985, pp. 1849–1857, vol. 260, No. 3, The American Society of Biological Chemists, Inc.

Yoder, M.D. et al., "New Domain Motif: The Structure of Pectate Lyase C, a Secreted Plant Virulence Factor", *Science*, Jun. 4, 1993, pp. 1503–1506, vol. 260.

Yoder, M.D. et al., "Unusual structural features in the parallel β–helix in pectate lyases", *Structure*, Dec. 15, 1993, pp. 241–251, vol. 1, Current Biology Ltd.

Zacharski, L.R. et al., "Blood Coagulation Activation in Cancer: Challenges for Cancer Treatment", *Hamostaseologic*, 1995, pp. 14–20, vol. 15, F.K. Schattauer Verlagsgesellschaft mbH.

Keiser, N. et al., "Direct isolation and sequencing of specific protein–binding glycosaminoglycans", *Nature Medicine*, Jan. 2001, pp. 123–128, vol. 7, No. 1.

Pojasek, K. et al., "Recombinant Expression, Purification, and Kinetic Characterization of Chondroitinase AC and Chondroitinase B from *Flavobacterium heparinum*", *Biochem. Biophys. Res. Commun.*, Aug. 17, 2001, pp. 343–351, vol. 286, No. 2, Academic Press.

Zhang, L. et al., "6–0–Sulfotransferase–1 Represents a Critical Enzyme in the Anticoagulant Heparan Sulfate Ciosynthetic Pathway", *J. Biol. Chem.*, Nov. 9, 2001, pp. 42311–42321, vol. 276, No. 45, The American Society for Biochemistry and Molecular biology, Inc. USA.

Yamada, S. et al, *Structural Studies on the Bacterial Lyase–Resistant Tetrasaccharides Derived From the Antithrombin III–Binding Site of Porcine Intestinal Heparin*, J. Biol. Chem. 268(7):4780 (1993).

Biemann, K., *J Am Soc Mass Spectrom*, 13(11):1254–1272, 2002.

Carlson, T.H. et al., *The Journal of Biological Chemistry*, 263(5):2187–2194, 1988.

Claverie et al., Computers Chem, vol. 17, No. 2: pp 191–201 1993.

Crum et al., "A new class of steroids inhibits angiogenesis in the presence of heparin or a heparin fragment", *Science*, 230: 1375–1378, 1985.

Dull et al., "Lung endothelial heparan sulfates mediate cationic peptide–induced barrier dysfunction: a new role for the glycocalyx", *Am. J. Physiol. Lung Cell Mol. Physiol.*, 285:L986–995, 2003.

Edwards, D.A. et al., *Science Reprint Series* 276:1868–1871, 1997.

Edwards, D.A. et al.,*J. Appl. Physiol.*, 85(2):379–385, 1998.

Ernst et al., "Expression in *Escherichia coli*, purification and characterization of heparinase I from *Flavobacterium heparinum*", *Biochem. J.*, 315:589–597, 1996.

Folkman et al., "Angiogenesis inhibition and tumor regression caused by heparin or a heparin fragment in the presence of cortisone", *Science*, 221:719–725, 1983.

Gioldassi, J., *Liquid Chromatography and Related Technology*, 22(13):1997–2007, 1999.

Godavarti et al., "Heparinase I from *Flavobacterium heparinum*", *The Journal of Biological Chemistry*, 273(1):248–255, 1998.

Guerrini et al., "A novel computational approach to integrate NMR spectroscopy and capillary electrophoresis for structure assignment of heparin and heparan sulfate oligosaccharides", *Glycobiology*, 12(11):713–719, 2002.

Harenberg, J., et al., *Blood Coagulation and Fibrinolysis*, 7:477–482, 1996.

Hayes, B., *American Scientist*, 86(3):216–221, 1998.

Horner, A.A., *Biochem. J.*, 244:693–698, 1987.

Johnson et al., "Endothelial cells preparing to die by apoptosis initiate a program of transcriptome and glycome regulation", *FASEB Journal*, 18:188–190, 2004.

Kanabrocki, E.L. et al., *Chronobiology International*, 8(3):210–233, 1991.

Kanabrocki, E.L. et al., *Quarterly Journal of Medicine*, 83(300):259–282, 1992.

Keiser et al., "Direct isolation and sequencing of specific protein–binding glycosaminoglycans", *Nature Medicine*, 7(1):123–128, 2001.

Kishibe et al., *J. Biol. Chem.*, 275(20):15321–15329, 2000.

Kreitz, M.R. et al., *Biomaterials*, 18:1645–1651, 1997.

Leckband, D., et al., *Abstracts of Papers from the Fourth Chemical Congress of North America*, 202(1):a56, 1991.

Liu, *Glycobiology*, 5(8): 765–774, 1995.

Liu, D, et al., "Tumor cell surface heparan sulfate as cryptic promoters or inhibitors of tumor growth and metastasis", *PNAS*, 99(2):568–573, 2002.

Liu, D. et al., "Dynamic regulation of tumor growth and metastasis by heparan sulfate glycosaminoglycans", *Seminars in Thrombosis and Hemostasis*, 28(1): 67–78, 2002.

Liu, J. et al., "Characterization of a heparan sulfate octasaccharide that binds to herpes simplex virus type 1 glycoprotein D", *The Journal of Biological Chemistry*, 277(36), 33456–33467, 2002.

Marciniak, E., *Blood*, 59(3):576–581, 1982.

McLean, M.W., et al., "Enzymic Removal of 2–0–Sulphato–$\Delta_{4,5}$–Glycuronic Acid Residues from Heparin Oligosaccharides", Proceeding of the $7^{th}$ International Symposium of Glycoconjugates, pp. 68–69, 1983.

Myette et al., "Molecular cloning of the heparin/heparan sulfate $\Delta 4,5$ unsaturated glycuronidase from *Flavobacterium heparinum*, its recombinant expression in *Escherichia coli*, and biochemical determination of its unique substrate specificity", *Biochemistry*, 41:7424–7434, 2002.

Myette et al., "The heparin/heparan sulfate 2–O–sulfatase from *Flavobacterium heparinum*", *The Journal of Biological Chemistry*, 278(14):12157–12166, 2003.

Myette et al., "Expression in *Escherichia coli*, purification and kinetic characterization of human heparan sulfate 3–O–sulfotransferase–1", *Biochemical and Biophysical Research Communications*, 290:1206–1213, 2002.

Nesheim, M. et al., *The Journal of Biological Chemistry*, 261(7):3214–3221, 1986.

Pixley, R. et al., *Thrombosis Research*, 26:129–133, 1982.

Pojasek et al., "Biochemical characterization of the chondroitinase B active site", *The Journal of Biological Chemistry*, 277(34):31179–31186, 2002.

Raman et al., "Identification of structural motifs and amino acids within the structure of the human heparan sulfate 3–O–sulfotransferase that mediate enzymatic function", *Biochemical and Biophysical Research Communications*, 290:1214–1219, 2002.

Raman et al., "The heparin/ heparan sulfate 2–O–sulfatase from *Flavobacterium heparinum*", *The Journal of Biological Chemistry*, 278(14):12167–12174, 2003.

Rhomberg, A.J., Proc. $45^{th}$ Annual Conference on Mass Spectrometry Allied Topics, 1026–1027, 1997 Abstract Only.

Rhomberg, A.J., MIT (*Department of Chemistry*), 1998 Thesis.

Rudd, P.M., et al., *Nature*, 388(6638):205–207, 1997.

Sasisekharan et al., "Roles of heparan–sulphate glycosaminoglycans in cancer", *Nature Reviews*, 2:521–528, 2002.

Shriver et al., "Emerging views of heparan sulfate glycosaminoglycan structure/activity relationships modulating dynamic biological functions", *TCM*, 12(2): 71–77, 2002.

Sundaram et al., "Rational design of low–molecular weight heparins with improved in vivo activity", *PNAS*, 100(2): 651–656, 2003.

Taylor et al., "Protamine is an inhibitor of angiogenesis", *Nature*, 297:307–312, 1982.

Yan, J.F., et al., *J. Theor. Biol.*, 151:333–341, 1991.

Zhao, Y., et al., *Proc. Natl. Acad. Sci.*, 94:1629–1633, 1997.

Ameer, G.A. et al., "A New Approach to Regional Heparinization: Design and Development of a Novel Immobilized Heparinas Device", *Blood Purification Meeting Info: Third International Conference on Continuous Renal Replacement Therapies, San Diego, CA, USA*, Mar. 5–7, 1998, pp. 107–108, vol. 16, No. 2, Abstract.

Berry, D. et al., "Distinct heparan sulfate glycosaminoglycans are responsible for mediating fibroblast growth factor–2 biological activity through different fibroblast growth factor receptors", *The FASEB Journal Express Article 10,1096/fj.00–0661fje.*, Published online Apr. 6, 2001, pp. 1–19.

Ernst, S. et al., "Enzymatic Degradation of Glycosaminoglycans", *Critical Reviews in Biochemistry and Molecular Biology*, 1995, pp. 387–444, vol. 30, No. 5, CRC Press, Inc.

Murphy, P.R. et al., "Basic fibroblast growth factor binding and processing by human glioma cells", *Molecular and Cellular Endocrinology*, 1995, pp. 193–203, vol. 114, No. 1–2, Elsevier Science Ireland Ltd.

Natke, B. et al., "Heparinase treatment of bovine smooth muscle cells inhibits fibroblast growth factor–2 binding to fibroblast growth factor receptor but not FGF–2 mediated cellular proliferation", *Angiogenesis*, 1999, pp. 249–257, vol. 3, No. 3, Khuwer Academic Publishers Netherlands.

Padera, R. et al., "FGF–2/fibroblast growth factor receptor/heparin–like glycosiminoglycan interactions: a compensatoin model for FGF–2 signaling", *The FASEB Journal*, Oct. 1999, pp. 1677–1687, vol. 13, No. 13.

* cited by examiner

| Sacch. code | HEP I | HEP III |
|---|---|---|
| D ΔU$_{2S}$-H$_{NS,6S}$ | 1 | 10 |
| 9 ΔU$_{2S}$-H$_{NS}$ | 0 | 6 |
| 5 ΔU-H$_{NS,6S}$ | 11 | 8 |
| C ΔU$_{2S}$-H$_{NAc,6S}$ | 3 | 5 |
| 1 ΔU-H$_{NS}$ | 23 | 12 |
| 8 ΔU$_{2S}$-H$_{NAc}$ | 8 | 18 |
| 4 ΔU-H$_{NAc,6S}$ | 13 | 8 |
| 0 ΔU-H | 41 | 33 |

| RESPONSE | FGF2 | Hep I FRAG. | Hep III FRAG. |
|---|---|---|---|
| CLOCK HOURS | 2.4 ± 0.24[#] | 3.4 ± 0.19 | 0.2 ± 0.12 |
| VESSEL LENGTH (mm) | 1.9 ± 0.05 | 2.0 ± 0.07 | 0.4 ± 0.22 |

HEPARINASE III AND USES THEREOF

RELATED APPLICATIONS

This application claims priority to U.S. Provisional Application Ser. No. 60/187,846 filed Mar. 8, 2000, the entire contents of which are incorporated herein by reference.

GOVERNMENT SUPPORT

Some aspects of the invention were made with government support under NIH Contract No. GM57073. The government may have certain rights in the invention.

FIELD OF THE INVENTION

The invention relates to heparinase III and mutants thereof. In particular, the invention relates to modified forms of heparinase III having reduced enzymatic activity which are useful for a variety of purposes, including sequencing of heparin-like glycosaminoglycans (HLGAGs), removing HLGAGs from a solution, inhibition of angiogenesis, inhibiting coagulation, etc. The invention in other aspects relates to methods of treating cancer and inhibiting tumor cell growth and/or metastasis using heparinase III, or HLGAG products produced by enzymatic cleavage with heparinase III.

BACKGROUND OF THE INVENTION

Heparin like glycosaminoglycans (HLGAGs) are important components of the extracellular matrix that are believed to regulate a wide variety of cellular activities including invasion, migration, proliferation and adhesion. Khodapkar, et al. 1998; Woods, et al., 1998) HLGAGs accomplish some of these functions by binding to and regulating the biological activities of diverse molecules, including growth factors, morphogens, enzymes, extracellular proteins. HLGAGs are linear polysaccharides characterized by a disaccharide-repeat unit of a uronic acid [α-L-iduronic acid (I) or β-D-glucuronic acid (G)] linked 1, 4 to α-B-hexosamine (H). (1) These polymers of 20–100 disaccharide units can be additionally modified through N-and O-sulfation, epimerization at the C5 position of the uronic acid moiety, adding an additional micro-heterogenecity to these information dense molecules (1.5).

Although the structure and chemistry of HLGAGs are fairly well understood, information on how specific HLGAG sequences modulate different biological processes has proven harder to obtain. The inventors have recently developed a rapid sequencing methodology for polysaccharides using chemical and enzymatic tools to modify or degrade an unknown HLGAG polymer in a sequence-specific manner. (Venkataraman, G., et al., *Science*, 286, 537–542 (1999), and U.S. patent applications Ser. Nos. 09/557,997 and 09/558, 137, both filed on Apr. 24, 2000). An important enzymatic tool in this sequencing process is the heparinases, including heparinases I, II and III. The three heparinases are HLGAG degrading enzymes which can be produced by *Flavobacterium heparinum*. Each of the heparinases has its own unique HLGAG sequence at which it cleaves, making these enzymes valuable tools in obtaining sequence specific information. Heparinase I primarily cleaves HLGAGs at the $H_{NS,6X}-I_{2S}^2$-linkage found primarily in heparin-like regions (Ernst, S., et al., *Crit, Rev. Biochem. Mol. Biol.*, 30, 387–444 (1995)). Desai, U., et al., *Biochemistry*, 32, 8140–8145 (1993)), and Jandik, K., et al., *Glycobiology*, 4, 289–296 (1994)). Heparinase III cleaves at the $H_{NAC}$-I and $H_{NY,6X}$-$G^2$ linkages which are the major disaccharides found in heparan sulfate (Ernst, et al., (1995), supra, and Linhardt, R., et al., *Biochemistry*, 29, 2611–2617 (1990)). Heparinase II is capable of recognizing and cleaving both sets of substrate linkages (Ernst, et al., (1995), supra). We have recently identified several residues which are critical to the activity of heparinase I and heparinase II. Cysteine 135 and histidine 203, as well as lysines 198, 199, and 132 of heparinase I were found to be critical to the enzymatic activity of the molecule. Cysteine 348 and histidines 238, 451, and 579 were determined to be crucial for heparinase II activity. (Pending U.S. patent application Ser. No., 09/384,959; Sasisekharan, R., et al., *Biochemistry*, 34, 14441–14448 (1995); Godavarti, R., et al., *Biochemistry*, 35, 6846–6852 (1996); Godavarti, R., and Sasisekharan, R., *J. Biol. Chem.* 273, 248–255 (1998); Shriver, Z., et al., *J. Biol. Chem.*, 273, 22904–22912 (1998); and Shriver, Z., *J. Biol. Chem.*, 273, 10160–10167 (1998)).

Heparinase III is unique in that it is the only member of the heparinase family that recognizes and preferentially cleaves heparan sulfate. Heparinase III also contains no cysteines in its amino acid sequence.

Tumor metastasis involves the spread of tumor cells primarily via the vasculature to remote sites in the body. It is believed that as the extracellular matrix is degraded, the tumor cell-extracellular matrix interactions are disassembled, freeing the tumor cell to extravagate through the capillary bed. Extraordinary progress has been made to elucidate the roles of collagen and related proteins, enzymes (collagenases and others) that degrade the extracellular matrix proteins to regulate tumor angiogenesis and/or tumor cell invasion. It has also recently been hypothesized that HLGAG degrading enzymes, heparinases, assist in the breakdown of the extracellular matrix to regulate tumor growth, angiogenesis and metastasis. It has been suggested that the expression of heparinases in association with tumor development, represents a switch from a metastatic tumor to a non-metastatic tumor and plays a role in initiating the process of metastasis. The hypothesis was reaffirmed by recent cloning of a human heparinase gene and by the demonstration of enhanced malignancy of cancer cells by over-expression of the gene product for heparinase. (Hulett, et al., 1999 and Vlodavsky, et al., 1999).

SUMMARY OF THE INVENTION

It has been discovered, according to one aspect of the invention, that expression of heparinases does not necessarily represent a switch from a primary tumor to a metastatic diseased state. Consistent with the current paradigm, heparinase I activity was found to accelerate tumor growth and correlate with increased metastasis. Surprisingly, heparinase III, however, was found to inhibit primary tumor growth and significantly reduce metastasis. Thus, in one aspect the invention is a method for preventing growth of a tumor by exposing a tumor cell to an effective amount of heparinase III for preventing proliferation of the tumor cells in order to prevent growth of the tumor. In other aspects, the invention is a method for preventing tumor cell metastasis by exposing a tumor cell to an effective amount of heparinase III for preventing invasion of the tumor cell across a barrier. The heparinase III may be a native heparinase III molecule or a modified heparinase III molecule. Native heparinase III may be synthesized or isolated.

Additionally, it has been discovered according to the invention that therapeutic HLGAG fragments can be used to treat cancer. These fragments are useful for preventing the growth of a tumor as well as preventing metastasis. These fragments can be generated by heparinase III treatment of cancer cells. The fragments generated from the heparinase III treatment of a cancer cell can be used to prevent or treat cancer from the same or different cancer cells than are used to generate the fragments. Additionally, they can be used to treat or prevent cancer in the same or a different subject than was used to generate the fragments.

The tumor cell can be exposed to the heparinase III by any method known in the art. For instance, when the tumor cell is a tumor cell in vitro, heparinase III may be added to the in vitro culture. When the tumor cell is in vivo, the heparinase III may be administered by any method for delivering the heparinase III to the tumor. For instance, in some embodiments the heparinase III may be administered systemically, such as by oral delivery, injection, etc. or locally, such as by direct injection into the tumor or tumor site or by direct application during surgical manipulation, etc.

The heparinase III may be administered alone or in conjunction with other therapies such as an anti-cancer drug. In some embodiments, the tumor is a prostate tumor or a melanoma.

In other aspects, the invention is a method for preparing therapeutic agents for the treatment of a tumor. The method involves isolating at least a portion of a tumor, treating the portion of the tumor with heparinase III to produce HLGAG fragments, and isolating the HLGAG fragments, wherein the HLGAG fragments are the therapeutic agent. In some embodiments, the method may also include the step of determining the sequence of the HLGAG fragments.

In other aspects of the invention, a method for treating a subject having a tumor is provided. The method involves administering to the subject therapeutic HLGAG fragments to treat the tumor. Optionally the method may involve identifying a therapeutic HLGAG fragment by identifying an HLGAG produced when the tumor is contacted with heparinase III. In some embodiments, the therapeutic HLGAG fragment is a synthetic HLGAG fragment generated based on the sequence of the HLGAG fragment identified when the tumor is contacted with heparinase III. In other embodiments, the HLGAG fragment administered to the subject is an isolated HLGAG fragment produced when the tumor is contacted with the heparinase III.

In another aspect the invention is a method for treating or preventing a subject having a cancer or at risk of developing a cancer by administering to the subject a therapeutic HLGAG fragment. In some embodiments the therapeutic HLGAG fragment is a composition of HLGAG fragments wherein at least 50%, 75%, or 90% of the HLGAG fragments are di- or tri-sulfated disaccharides. In other embodiments the therapeutic HLGAG fragment is free of mono- or un-sulfated disaccharides.

According to another aspect of the invention, a composition is provided. The composition includes heparinase III or a therapeutic HLGAG fragment in an effective amount for preventing metastasis of a tumor cell, and a targeting molecule for targeting the heparinase III to the tumor, in a pharmaceutically-acceptable carrier. In some embodiments the heparinase III is a modified heparinase III and in other embodiments it is a native heparinase III. The targeting molecule may be, for instance, a compound which binds specifically to an antigen on the surface of a tumor cell.

The invention in another aspect is a composition of a heparinase III or a therapeutic HLGAG fragment in an effective amount for preventing metastasis of a tumor cell, and an anti-cancer compound in a pharmaceutically-acceptable carrier.

The invention in other aspects is based on the identification of important residues within the heparinase III molecule. It has been discovered according to the invention that modification of certain histidine residues within the heparinase III molecule causes changes in the enzymatic rate of the enzyme as well as the product profile produced by the enzyme. In particular, it was discovered that histidine 295 and histidine 510 are important for enzymatic degradation of heparan sulfate by heparinase III. When these two histidines were changed to other amino acids, all of the activity of the enzyme was lost. Modification of the other histidine residues resulted in changes in kinetic constants of the enzyme, but the enzyme still retained activity. Thus, in another aspect the invention is a substantially pure heparinase III comprising a polypeptide having the amino acid sequence of the mature peptide of SEQ ID NO:2 or having conservative substitutions thereof within residues non-essential to enzymatic function, wherein at least one histidine residue selected from the group consisting of His 36, His 105, His 110, His 139, His 152, His 225, His 234, His 241, His 424, His 469, and His 539 has been substituted with a residue selected from the group consisting of alanine, serine, tyrosine, threonine, and lysine. In some embodiments the polypeptide has a substitution at His 110 or His 241. In other aspects, the invention is a substantially pure heparinase III comprising a polypeptide having the amino acid sequence of the mature peptide of SEQ ID NO:2 or having conservative substitutions thereof within residues non-essential to enzymatic function, wherein at least one histidine residue selected from the group consisting of His 295 and His 510 has been substituted with any other amino acid.

In another aspect, the invention is a substantially pure heparinase III which is a modified heparinase III having a modified product profile, wherein the modified product profile of the modified heparinase III is at least 10% different than a native product profile of a native heparinase III.

In another aspect, the invention is a substantially pure heparinase III that is a modified heparinase III that can cleave a HLGAG substrate having a modified heparinase III $k_{cat}$ value, wherein the modified heparinase III $k_{cat}$ value is at least 10% different than a native heparinase III $k_{cat}$ value. The invention also encompasses pharmaceutical preparations of any of the substantially pure heparinase III molecules with a pharmaceutically-acceptable carrier. The invention also encompasses the modified heparinase III of the invention immobilized on a solid support membrane.

A method of specifically cleaving a HLGAG is provided according to another aspect of the invention. The method of specifically cleaving a HLGAG includes the step of contacting an HLGAG with the modified heparinase III of the invention. In some embodiments, the method is a method for preventing tumor cell proliferation or metastasis, as described above. In other embodiments, the method is a method for sequencing HLGAGs. In yet other embodiments, the method is a method for removing active HLGAGs from an HLGAG-containing fluid, a method for inhibiting angiogenesis, a method for inhibiting neovascularization, e.g., such as that associated with eye disease, a method for treating psoriasis, or a method for inhibiting coagulation.

The invention also includes a method for preparing LMWH by contacting an HLGAG sample with a modified heparinase III molecule to produce LMWH. In other aspects the invention is a composition of the LMWH produced by this method. In yet another aspect the invention is also a method for treating or preventing a disorder associated with coagulation, tumor, psoriasis, or neovascularization, by administering to a subject an effective amount of this composition to treat or prevent a disorder associated with coagulation, tumor, psoriasis, or neovascularization.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 8, panel B, is a graph depicting tumor volume in mice treated with PBS, inactive heparinase III, active heparinase III, and heparinase I.

FIG. 10, panel B is a bar graph which quantitates the number of lung nodules of the mice described in panel A.

FIG. 13, panel B, depicts the analysis of the heparinase III-generated fragments. FIG. 13, panel C, depicts the analysis with PBS as a control. FIG. 13, panel D, provides a table showing the relative percentage of HLGAG disaccharides in the heparinase I and heparinase III-generated fragments. FIG. 13, panels E and F, show the mass spectrometric oligosaccharide mapping of heparinase I and heparinase III derived HLGAG saccharide fragments.

BRIEF DESCRIPTION OF THE SEQUENCES

Figure 1:
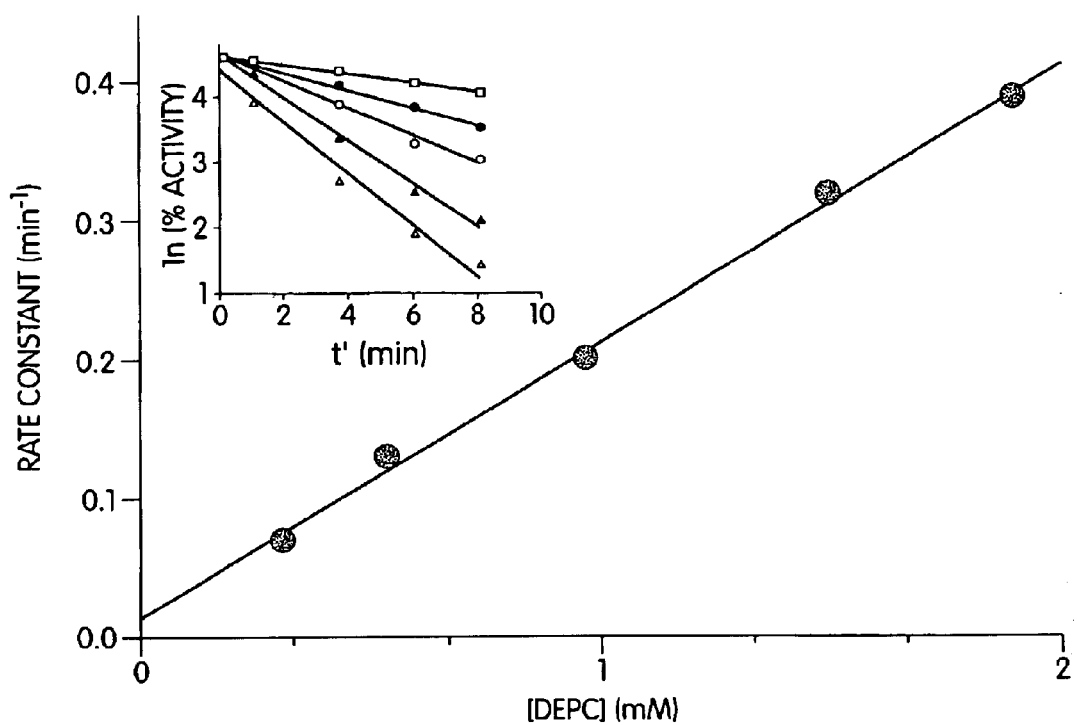
FIG. 1 is a graph depicting the effect of DEPC inactivation of heparinase III on rate constant.

Sequence ID No. 1 is the nucleic acid sequence of heparinase III from *F. bacterium*.

Sequence ID No. 2 is the amino acid sequence of heparinase III from *F. bacterium*.

Sequence ID No. 3 is a peptide fragment.

DETAILED DESCRIPTION

The invention in some aspects relates to heparinase III, modified forms thereof and uses thereof. The invention arose from several scientific findings which expand the field of heparinase biology. In particular the invention is based in part on the discovery of new modified forms of heparinase that have varying enzymatic activity and produce differing product profiles. The invention is also based on the finding that native heparinase III, modified forms of heparinase III, and modified forms of heparinase II having heparinase III like activity are useful for the treatment and prevention of tumor cell growth and metastasis.

The present invention provides a series of new modified heparinase III molecules. In particular, based upon a detailed structural and functional characterization of heparinase III, new heparinases with altered stability, activity and specificity are provided. The modified heparinases of the invention have many in vivo, in vitro and ex vivo utilities. For instance, they have great value in generating low molecular weight HLGAGs, heparan sulfate, or heparan sulfate fragments for clinical use. Additionally they can be used to neutralize the function of heparan sulfate containing HLGAGs or they can be used to identify the sequence of HLGAGs. Other uses are described herein.

Heparinase III is unique in that it is the only member of the heparinase family that recognizes and cleaves heparan sulfate as its only substrate. Heparinase III is also unique among its heparin-degrading family members in that it contains no cysteines in its primary amino acid sequence (Su, H., Blain, F., Musil, R. A., Zimmermann, J. J., Gu, K., and Bennett, D. C. (1996) *Appl. Environ. Micro.* 62,2723–34 and Godavarti, R., Davis, M., Venkataraman, G., Cooney, C. L., Langer, R., and Sasisekharan, R. (1996) *Biochem. and Biophys. Res. Comm.* 225, 751–58). Heparinase III, however, does contain thirteen histidines of which one or several might be involved in the activity of the enzyme. Through a combination of chemical modification, peptide mapping, and site-directed mutagenesis studies, the role of histidines in the catalytic activity of heparinase III has been identified, according to the invention.

The nucleotide and amino acid sequences of heparinase III are provided in SEQ ID NO: 1 and SEQ ID NO: 2. The sequence of heparinase III has been reported in Su, H., Blain, F., Musil, R. A., Zimmermann, J. J., Gu, K., and Bennett, D. C. (1996) *Appl. Environ. Micro.* 62, 2723–34. and Godavarti, R., Davis, M., Venkataraman, G., Cooney, C. L., Langer, R., and Sasisekharan, R. (1996) *Biochem. and Biophys. Res. Comm.* 225, 751–58, U.S. Pat. Nos. 5,919,693 and 5,681,733, and is listed in Accession number 171365. These sequences have provided the first insight into the primary structure of the native heparinase III of *F. heparinum*.

The present disclosure provides additional information about the secondary and tertiary structure of the heparinase III, as well as, information relating to the functional roles of the various regions of the enzyme. This information is based upon detailed biochemical mapping of the important sites within the enzyme and characterization of these sites through kinetic studies, characterization of mutants created by site-directed mutagenesis, etc. The result is a detailed picture of the primary, secondary, and tertiary structures of heparinase III and the functional roles of various regions of the enzyme as well as the functions of specific mutants thereof.

The invention is based on several scientific findings. It was discovered according to the invention that various amino acid residues within heparinase III are essential to the catalytic function of these enzymes and can be modified to alter the enzymatic activity of these compounds. It was also discovered that other amino acid residues are absolutely critical to the function of heparinase III and if they are substituted or modified the activity of these compounds is lost completely. In particular, it has been shown according to the invention through a combination of chemical modification, peptide mapping, and site-directed mutagenesis experiments that two histidines, histidine 295 and histidine 510, are critical for the enzymatic degradation of HLGAGs by heparinase As shown in the Examples section, DEPC was used in the first step of the analysis of heparinase III. DEPC is extremely useful in elucidating the role of histidines in enzymatic function. Care has to be taken, though, to ensure that DEPC doesn't modify other nucleophilic amino acids such as tyrosine, lysine or cysteine (Godavarti, R., Cooney, C. L., Langer, R., and Sasisekharan, R. (1996) *Biochemistry* 35, 6846–52 and Shriver, Z., Hu, Y., and Sasisekharan, R. (1998) *J. Biol. Chem.* 273, 10160–67). In the case of heparinase III, there are no cysteine residues in the primary amino acid sequence, eliminating this amino acid as a potential confounding factor in the chemical modification studies. Also, no decrease in the absorbance at 278 nm was observed after heparinase III was incubated with DEPC, indicating that tyrosine residues were not modified. An increase in the inactivation kinetics without a change in the order of the reaction was observed from pH 6.0–7.5 upon DEPC treatment. Furthermore, the DEPC modification was 90% reversible upon incubation with 300 mM hydroxylamine. Above pH 8.0, the inactivation kinetics were no longer first order for DEPC and the modification could not be reversed by hydroxylamine, indicating that residues other than histidines (i.e. lysines) were being modified at those pHs. However, at neutral pH, the data indicates that DEPC specifically modifies the histidine residues of heparinase III.

Consistent with the observation that DEPC is modifying a histidine residue, there was an increase in the absorbance at 240 nm as a function of time. This is indicative of formation of an N-carbethoxyhistidyl derivative, the product of a reaction between DEPC and a histidine residue. Over the course of ten minutes, 1.8 histidine residues were modified and the enzymatic activity was decreased by 90%. Also, pre-incubation with heparan sulfate resulted in lower inactivation kinetics of heparinase III by DEPC. These data indicated that DEPC specifically modified a critical histidine residue proximate to the substrate binding/active site of heparinase III, inactivating the enzyme.

An apparent discrepancy arose from these results in that the reaction of DEPC with heparinase III follows pseudo-first order kinetics, yet two histidines appeared to be independently modified, suggesting that two surface accessible histidines react with DEPC at identical rates. It could be the case that either one or both of the modified residues is responsible for inactivating the enzyme. Site-directed mutagenesis experiments were performed to determine if two histidines were essential for heparinase III's catalytic activity. The results from the site-directed mutagenesis experiments confirmed and expanded upon the chemical modification data in that surface accessible histidines are critical for heparinase III activity. These results identify histidine 295 and histidine 510 as the primary histidines involved in the degradation of HLGAGs by heparinase III. When these residues are replaced with alanines, the enzyme loses all activity towards its substrate. None of the other histidine residues when mutated to alanine show a complete loss of activity. The results from the peptide mapping studies confirm the importance of the surface accessibility of histidine 295.

The loss of activity with the H295A and H510A enzymes can be explained in several ways. It may be that these histidines are necessary for proper folding of heparinase III. However, the CD spectrum of H295A, H510A, and recombinant heparinase III were nearly identical, strongly indicating that this is not the case. It is more likely that histidine 295 and histidine 510 play a direct role in the binding of HLGAGs to the enzyme or that histidine 295 and histidine 510 are critical active site residues directly involved in the catalytic degradation of HLGAGs. Modified heparinase III molecules having a change in amino acid at His 295 or 510 can be useful for a variety of purposes, e.g., as a competitive inhibitor to functional heparinase III.

The studies described in the Examples section also identified several heparinase III mutants which had altered levels of activity but which were still active. These mutants include heparinase III molecules having the following residues mutated or substituted: His36, His105, His110, His139, His152, His225, His234, His241, His424, His469, and His539. Thus, the present invention provides for novel modified heparinases rationally designed on the basis of the sequence of the heparinase III of *F. heparinum* and the structural and functional characterizations disclosed herein.

In the description herein, reference is made to the amino acid residues and residue positions of native heparinase III disclosed in SEQ ID NO 2. In particular, residues and residue positions are referred to as "corresponding to" a particular residue or residue position of heparinase III. As will be obvious to one of ordinary skill in the art, these positions are relative and, therefore, insertions or deletions of one or more residues would have the effect of altering the numbering of downstream residues. In particular, N-terminal insertions or deletions would alter the numbering of all subsequent residues. Therefore, as used herein, a residue in a recombinant modified heparinase will be referred to as "corresponding to" a residue of the full heparinase III if, using standard sequence comparison programs, they would be aligned. Many such sequence alignment programs are now available to one of ordinary skill in the art and their use in sequence comparisons has become standard. As used herein, this convention of referring to the positions of residues of the recombinant modified heparinases by their corresponding heparinase III residues shall extend not only to embodiments including N-terminal insertions or deletions but also to internal insertions or deletions (e.g., insertions or deletions in "loop" regions).

In addition, in the description herein, certain substitutions of one amino acid residue for another in a recombinant modified heparinase are referred to as "conservative substitutions." As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). The term "conservative amino acid substitution" also refers to the use of amino acid analogs or variants.

Methods for making amino acid substitutions, additions or deletions are well known in the art and are described in detail in the Examples below. The terms "conservative substitution", "non-conservative substitutions", "non-polar amino acids", "polar amino acids", and "acidic amino acids" are all used consistently with the prior art terminology. Each of these terms is well-known in the art and has been extensively described in numerous publications, including standard biochemistry text books, such as "Biochemistry" by Geoffrey Zubay, Addison-Wesley Publishing Co., 1986 edition, which describes conservative and non-conservative substitutions, and properties of amino acids which lead to their definition as polar, non-polar or acidic.

Even when it is difficult to predict the exact effect of a substitution in advance of doing so, one skilled in the art will appreciate that the effect can be evaluated by routine screening assays, preferably the biological assays described herein. Modifications of peptide properties including thermal stability, hydrophobicity, susceptibility to proteolytic degradation or the tendency to aggregate with carriers or into multimers are assayed by methods well known to the ordinarily skilled artisan. For additional detailed description of protein chemistry and structure, see Schulz, G. E. et al., Principles of Protein Structure, Springer-Verlag, New York, 1979, and Creighton, T. E., Proteins: Structure and Molecular Principles, W. H. Freeman & Co., San Francisco, 1984.

Additionally, some of the amino acid substitutions are non-conservative substitutions. In certain embodiments where the substitution is remote from the active or binding sites, the non-conservative substitutions are easily tolerated provided that they preserve the tertiary structure characteristic of native heparinase, thereby preserving the active and binding sites. Non-conservative substitutions, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain.

In one aspect, the invention is a substantially pure heparinase which is a modified heparinase III having a modified heparinase III $k_{cat}$ value, wherein the modified heparinase III $k_{cat}$ value is at least 10% different than a native heparinase III $k_{cat}$ value. In a preferred embodiment, the modified heparinase III $k_{cat}$ value is at least 20% different than a native heparinase III $k_{cat}$ value. In another preferred embodiment the modified heparinase III $k_{cat}$ value is at least 50% different than a native heparinase III $k_{cat}$ value. A "modified heparinase III $k_{cat}$ value" as used herein is a measurement of the catalytic activity of the modified heparinase III enzyme with respect to a heparan sulfate-like glycosaminoglycan substrate.

The $k_{cat}$ value may be determined using any enzymatic activity assay which is useful for assessing the activity of a heparinase enzyme, such as the assays set forth in the Examples below. Several such assays are well-known in the art. For instance, an assay for measuring $k_{cat}$ is described in (Ernst, S. E., Venkataraman, G., Winkler, S., Godavarti, R., Langer, R., Cooney, C. and Sasisekharan. R. (1996) Biochem. J. 315, 589–597. The "native heparinase III $k_{cat}$ value" is the measure of enzymatic activity of the native heparinase III.

The modified heparinase may have a reduced enzymatic activity with respect to HLGAGs. A "reduced enzymatic activity" is assessed by comparing the $k_{cat}$ value of the modified heparinase with that of native heparinase. Preferably the $k_{cat}$ value of the modified heparinase III will be less than or equal to 75% of the native heparinase III $k_{cat}$ value. A modified heparinase having reduced enzymatic activity with respect to HLGAGs is one which has modifications in the residues essential for catalytic activity. For instance, mutation of His[110] or His[241] causes the heparinase III to have a reduced enzymatic activity. A modified heparinase III which has a increased enzymatic activity is one which has altered residues which produce an enzyme with greater enzymatic activity. For instance, mutation of His[139] produces modified heparinase III molecules having increased enzymatic activity. Additionally, when His[225] is mutated in heparinase III, a modified heparinase III is produced which displays nearly the same enzymatic activity as native heparinase III. These enzymes are also useful.

As used herein, with respect to heparinases, the term "substantially pure" means that the heparinases are essentially free of other substances with which they may be found in nature or in vivo systems to an extent practical and appropriate for their intended use. In particular, the heparinases are sufficiently free from other biological constituents of their hosts cells so as to be useful in, for example, producing pharmaceutical preparations or sequencing. Because the heparinases of the invention may be admixed with a pharmaceutically acceptable carrier in a pharmaceutical preparation, the heparinase may comprise only a small percentage by weight of the preparation. The heparinase is nonetheless substantially pure in that it has been substantially separated from the substances with which it may be associated in living systems.

Based on the disclosure provided herein, those of ordinary skill in the art will be able to identify other modified heparinase III molecules having altered enzymatic activity with respect to the native heparinase III molecule.

In another aspect, the invention is a substantially pure heparinase which is a modified heparinase III having a modified product profile, wherein the modified product profile of the modified heparinase III is at least 10% different than a native product profile of a native heparinase III. Preferably it is at least 20% or even at least 50%. A "modified product profile" as used herein is a set of degradation products produced by a modified heparinase which differ from the degradation products which are produced by a native heparinase under identical enzymatic conditions. The difference in the product profile may be due to the presence of different enzymatic products or simply in the number of enzymatic products formed by the modified heparinase compared to the native heparinase, or a combination of the two. For instance, the formation of different enzymatic products by a modified heparinase as opposed to the native heparinase, would constitute a modified product profile. Additionally, the production of the same types of enzymatic products but in a lesser or greater amount by the modified heparinase as opposed to the native heparinase, would also constitute a modified product profile.

The product profile produced by a modified heparinase or a native heparinase may be determined by any method known in the art for examining the type or quantity of degradation product produced by heparinase. One preferred method for determining the type and quantity of product is described in Rhomberg, A. J. et al., *PNAS*, v. 95, p. 4176–4181 (April 1998), which is hereby incorporated in its entirety by reference. The method disclosed in the Rhomberg reference utilizes a combination of mass spectrometry and capillary electrophoretic techniques to identify the enzymatic products produced by heparinase. The Rhomberg study utilizes heparinase to degrade HLGAGs to produce HLGAG oligosaccharides. MALDI (Matrix-Assisted Laser Desorption Ionization) mass spectrometry can be used for the identification and semiquantitative measurement of substrates, enzymes, and end products in the enzymatic reaction. The capillary electrophoresis technique separates the products to resolve even small differences amongst the products and is applied in combination with mass spectrometry to quantitate the products produced. Capillary electrophoresis may even resolve the difference between a disaccharide and its semicarbazone derivative. Detailed methods for sequencing polysaccharides and other polymers are disclosed in co-pending U.S. patent applications Ser. Nos. 09/557,997 and 09/558,137, both filed on Apr. 24, 2000 and having common inventorship. The entire contents of both applications are hereby incorporated by reference.

Briefly, the method is performed by enzymatic digestion, followed by mass spectrometry and capillary electrophoresis. The enzymatic assays can be performed in a variety of manners, as long as the assays are performed identically on the modified heparinase and the native heparinase, so that the results may be compared. In the example described in the Rhomberg reference, enzymatic reactions are performed by adding 1 mL of enzyme solution to 5 mL of substrate solution. The digestion is then carried out at room temperature (22° C.), and the reaction is stopped at various time points by removing 0.5 mL of the reaction mixture and adding it to 4.5 mL of a MALDI matrix solution, such as caffeic acid (approximately 12 mg/mL) and 70% acetonitrile/water. The reaction mixture is then subjected to MALDI mass spectrometry. The MALDI surface is prepared by the method of Xiang and Beavis (Xiang and Beavis (1994) *Rapid. Commun. Mass. Spectrom.* 8, 199–204). A two-fold lower access of basic peptide $(Arg/Gly)_{15}$ is pre-mixed with matrix before being added to the oligosaccharide solution. A 1 mL aliquot of sample/matrix mixture containing 1–3 picomoles of oligosaccharide is deposited on the surface. After crystallization occurs (typically within 60 seconds), excess liquid is rinsed off with water. MALDI mass spectrometry spectra is then acquired in the linear mode by using a PerSeptive Biosystems (Framingham, Mass.) Voyager Elite reflectron time-of-flight instrument fitted with a 337 nanometer nitrogen laser. Delayed extraction is used to increase resolution (22 kV, grid at 93%, guidewire at 0.15%, pulse delay 150 ns, low mass gate at 1,000, 128 shots averaged). Mass spectra are calibrated externally by using the signals for proteinated $(Arg/Gly)_{15}$ and its complex with the oligosaccharide.

Capillary electrophoresis is then performed on a Hewlett-Packard[3D] CE unit by using uncoated fused silica capillaries (internal diameter 75 micrometers, outer diameter 363 micrometers, $1_{det}$ 72.1 cm, and $1_{tot}$ 85 cm). Analytes are monitored by using UV detection at 230 mn and an extended light path cell (Hewlett-Packard). The electrolyte is a solution of 10 mL dextran sulfate and 50 millimolar Tris/phosphoric acid (pH2.5). Dextran sulfate is used to suppress nonspecific interactions of the heparin oligosaccharides with a silica wall. Separations are carried out at 30 kV with the anode at the detector side (reversed polarity). A mixture of a ⅕-naphtalenedisulfonic acid and 2-naphtalenesulfonic acid (10 micromolar each) is used as an internal standard.

Other methods for assessing the product profile may also be utilized. For instance, other methods include methods which rely on parameters such as viscosity (Jandik, K. A., Gu, K. and Linhardt, R. J., (1994), *Glycobiology*, 4:284–296) or total UV absorbance (Ernst, S. et al., (1996), *Biochem. J.*, 315:589–597) or mass spectrometry or capillary electrophoresis alone.

The modified heparinases of the invention may be used for any of the same purposes as native heparinase III. For instance, the modified heparinase III molecules can be used to specifically cleave a HLGAG by contacting the HLGAG substrate with one of the modified heparinases of the invention. The invention is useful in a variety of in vitro, in vivo and ex vivo methods in which it is useful to cleave HLGAGs.

The modified heparinase III may be used, for instance, in a method for inhibiting angiogenesis. In this method an effective amount for inhibiting angiogenesis of the heparinase III is administered to a subject in need of treatment thereof. Angiogenesis as used herein is the inappropriate formation of new blood vessels. "Angiogenesis" often occurs in tumors when endothelial cells secrete a group of growth factors that are mitogenic for endothelium causing the elongation and proliferation of endothelial cells which results in a generation of new blood vessels. Several of the angiogenic mitogens are heparin or heparan sulfate binding peptides which are related to endothelial cell growth factors.

The modified heparinases are also useful for treating or preventing cancer cell growth or metastasis. This aspect of the invention is discussed in more detail below, with respect to both native and modified heparinase III.

The modified heparinases are also useful for inhibiting neovascularization associated with disease such as eye disease. Neovascularization, or angiogenesis, is the growth and development of new arteries. It is critical to the normal development of the vascular system, including injury-repair. There are, however, conditions characterized by abnormal neovascularization, including diabetic retinopathy, neovascular glaucoma, rheumatoid arthritis, and certain cancers. For example, diabetic retinopathy is a leading cause of blindness. There are two types of diabetic retinopathy, simple and proliferative. Proliferative retinopathy is characterized by neovascularization and scarring. About one-half of those patients with proliferative retinopathy progress to blindness within about five years.

Another example of abnormal neovascularization is that associated with solid tumors. It is now established that unrestricted growth of tumors is dependant upon angiogenesis, and that induction of angiogenesis by liberation of angiogenic factors can be an important step in carcinogenesis. For example, basic fibroblast growth factor (bFGF) is liberated by several cancer cells and plays a crucial role in cancer angiogenesis. As used herein, an angiogenic condition means a disease or undesirable medical condition having a pathology including neovascularization. Such diseases or conditions include diabetic retinopathy, neovascular glaucoma and rheumatoid arthritis (non-cancer angiogenic conditions). Cancer angiogenic conditions are solid tumors and cancers or tumors otherwise associated with neovascularization such as hemangioendotheliomas, hemangiomas and Kaposi's sarcoma.

Proliferation of endothelial and vascular smooth muscle cells is the main feature of neovascularization. Thus the modified heparinase III of the invention is useful for preventing proliferation and, therefore, inhibiting or arresting altogether the progression of the angiogenic condition which depends in whole or in part upon such neovascularization.

Neovascularization and angiogenesis are also important in a number of other pathological processes, including arthritis, psoriasis, diabetic retinopathy, chronic inflammation, scleroderma, hemangioma, retrolental fibroplasia and abnormal capillary proliferation in hemophiliac joints, prolonged menstruation and bleeding, and other disorders of the female reproductive system (J. Folkman, Nature Medicine, Vol 1, p. 27–31, (1995); J. W. Miller, et al., J. Pathol., Vol. 145, pp. 574–584 (1994); A. P. Adamid, et al., Amer. J. Ophthal., Vol. 118, pp. 445–450 (1994); K. Takahashi, at al., J. Clin. Invest., Vol. 93, pp. 2357–2364 (1994); D. J. Peacock, et al., J. Exp. Med., Vol. 175, pp. 1135–1138 (1992); B. J. Nickoloff, et al., Amer. J. Pathol., Vol. 44, pp. 820–828 (1994); J. Folkman, Steroid Hormones and Uterine Bleeding, N. J. Alexander and C. d'Arcangues, Eds., American Association for the Advancement of Science Press, Washington, D.C., U.S.A., pp. 144–158 (1992)). Thus, in another embodiment, the modified heparinase is administered to treat diseases such as psoriasis. Psoriasis is a common dermatological disease caused by chronic inflammation.

The H295A and H510A modified heparinases are also useful according to the invention as inhibitors of heparinase III activity. These modified heparinases have a minimum one base pair modification from native heparinase but have no enzymatic activity. Thus, modified heparinases having a H295A or H510A modification can be used as competitive inhibitors of native or functional modified forms of heparinase III. These compounds are useful any time it is desirable to block heparinase III activity, e.g., when cell proliferation and migration is desirable or to block the activity of heparinase III in a solution.

The modified heparinases of the invention are also useful as tools for sequencing HLGAGs. Detailed methods for sequencing polysaccharides and other polymers are disclosed in co-pending U.S. patent applications Ser. Nos. 09/557,997 and 09/558,137, both filed on Apr. 24, 2000 and having common inventorship. These methods utilize tools such as heparinases in the sequencing process. The modified heparinase III of the invention is useful as such a tool.

The modified heparinases of the invention may also be used to remove active HLGAGs from a HLGAG containing fluid. A HLGAG containing fluid is contacted with the modified heparinase III of the invention to degrade the HLGAG. The method is particularly useful for the ex vivo removal of HLGAGs from blood. In one embodiment of the invention the modified heparinase is immobilized on a solid support as is conventional in the art. The solid support containing the immobilized modified heparinase may be used in extracorporeal medical devices (e.g. hemodialyzer, pump-oxygenator) for systemic heparinization to prevent the blood in the device from clotting. The support membrane containing immobilized heparinase III is positioned at the end of the device to neutralize the HLGAG before the blood is returned to the body.

In another aspect, the invention is an immobilized substantially pure heparinase of the invention. The heparinase may be immobilized to any type of support but if the support is to be used in vivo or ex vivo it is desired that the support is sterile and biocompatible. A biocompatible support is one which would not cause an immune or other type of damaging reaction when used in a subject. The heparinase may be immobilized by any method known in the art. Many methods are known for immobilizing proteins to supports.

The heparinase III is, in some embodiments, immobilized on a solid support. A "solid support" as used herein refers to any solid material to which a protein can be immobilized. Solid supports, for example, include but are not limited to membranes, e.g., natural and modified celluloses such as nitrocellulose or nylon, Sepharose, Agarose, glass, polystyrene, polypropylene, polyethylene, dextran, amylases, polyacrylamides, polyvinylidene difluoride, other agaroses, and magnetite, including magnetic beads. The carrier can be totally insoluble or partially soluble and may have any possible structural configuration. Thus, the support may be spherical, as in a bead, or cylindrical, as in the inside surface of a test tube or microplate well, or the external surface of a rod. Alternatively, the surface may be flat such as a sheet, test strip, bottom surface of a microplate well, etc.

The modified heparinase III molecules are also useful for generating LMWHs which have many therapeutic utilities. The modified heparinase III molecules and LMWH can be used for the treatment of any type of condition in which LMWH therapy has been identified as a useful therapy, e.g., preventing coagulation, preventing psoriasis.

Thus, the modified heparinase molecules are useful for treating or preventing disorders associated with coagulation. A "disease associated with coagulation" as used herein refers to a condition characterized by local inflammation resulting from an interruption in the blood supply to a tissue due to a blockage of the blood vessel responsible for supplying blood to the tissue such as is seen for myocardial or cerebral infarction. A cerebral ischemic attack or cerebral ischemia is a form of ischemic condition in which the blood supply to the brain is blocked. This interruption in the blood supply to the brain may result from a variety of causes, including an intrinsic blockage or occlusion of the blood vessel itself, a remotely originated source of occlusion, decreased perfusion pressure or increased blood viscosity resulting in inadequate cerebral blood flow, or a ruptured blood vessel in the subarachnoid space or intracerebral tissue.

The methods of the invention are useful also for treating cerebral ischemia. Cerebral ischemia may result in either transient or permanent deficits and the seriousness of the neurological damage in a patient who has experienced cerebral ischemia depends on the intensity and duration of the ischemic event. A transient ischemic attack is one in which the blood flow to the brain is interrupted only briefly and causes temporary neurological deficits, which often are clear in less than 24 hours. Symptoms of TIA include numbness or weakness of face or limbs, loss of the ability to speak clearly and/or to understand the speech of others, a loss of vision or dimness of vision, and a feeling of dizziness. Permanent cerebral ischemic attacks, also called stroke, are caused by a longer interruption in blood flow to the brain resulting from either a thromboembolism. A stroke causes a loss of neurons typically resulting in a neurologic deficit that may improve but that does not entirely resolve.

Thromboembolic stroke is due to the occlusion of an extracranial or intracranial blood vessel by a thrombus or embolus. Because it is often difficult to discern whether a stroke is caused by a thrombosis or an embolism, the term "thromboembolism" is used to cover strokes caused by either of these mechanisms.

The methods of the invention in some embodiments are directed to the treatment of acute thromboembolic stroke using modified heparinase III or the LMWHs generated therewith. An acute stroke is a medical syndrome involving neurological injury resulting from an ischemic event, which is an interruption in the blood supply to the brain.

An effective amount of a modified heparinase III or the LMWHs generated therewith alone or in combination with another therapeutic for the treatment of stroke is that amount sufficient to reduce in vivo brain injury resulting from the stroke. A reduction of brain injury is any prevention of injury to the brain which otherwise would have occurred in a subject experiencing a thromboembolic stroke absent the treatment of the invention. Several physiological parameters may be used to assess reduction of brain injury, including smaller infarct size, improved regional cerebral blood flow, and decreased intracranial pressure, for example, as compared to pretreatment patient parameters, untreated stroke patients or stroke patients treated with thrombolytic agents alone.

The modified heparinase III or the LMWHs generated therewith may be used alone or in combination with a therapeutic agent for treating a disease associated with coagulation. Examples of therapeutics useful in the treatment of diseases associated with coagulation include anticoagulation agents, antiplatelet agents, and thrombolytic agents.

Anticoagulation agents prevent the coagulation of blood components and thus prevent clot formation. Anticoagulants include, but are not limited to, heparin, warfarin, coumadin, dicumarol, phenprocoumon, acenocoumarol, ethyl biscoumacetate, and indandione derivatives.

Antiplatelet agents inhibit platelet aggregation and are often used to prevent thromboembolic stroke in patients who have experienced a transient ischemic attack or stroke. Antiplatelet agents include, but are not limited to, aspirin, thienopyridine derivatives such as ticlopodine and clopidogrel, dipyridamole and sulfinpyrazone, as well as RGD mimetics and also antithrombin agents such as, but not limited to, hirudin.

Thrombolytic agents lyse clots which cause the thromboembolic stroke. Thrombolytic agents have been used in the treatment of acute venous thromboembolism and pulmonary emboli and are well known in the art (e.g. see Hennekens et al, *J Am Coll Cardiol*; v. 25 (7 supp), p. 18S–22S (1995); Holmes, et al, *J Am Coll Cardiol*; v.25 (7 suppl), p. 10S–17S(1995)). Thrombolytic agents include, but are not limited to, plasminogen, $a_2$-antiplasmin, streptokinase, antistreplase, tissue plasminogen activator (tPA), and urokinase. "tPA" as used herein includes native tPA and recombinant tPA, as well as modified forms of tPA that retain the enzymatic or fibrinolytic activities of native tPA. The enzymatic activity of tPA can be measured by assessing the ability of the molecule to convert plasminogen to plasmin. The fibrinolytic activity of tPA may be determined by any in vitro clot lysis activity known in the art, such as the purified clot lysis assay described by Carlson, et. al., *Anal. Biochem.* 168, 428–435 (1988) and its modified form described by Bennett, W. F. Et al., 1991, Supra, the entire contents of which are hereby incorporated by reference.

The invention also relates to the discovery that heparinase III, modified forms thereof, modified forms of heparinase II and degradation products of heparinases (HLGAG fragments) actually are useful for treating and preventing cancer cell proliferation and metastasis. Thus, according to another aspect of the invention, there is provided methods for treating subjects having or at risk of having cancer.

Heparinases degrade HLGAGs, which are linear polysaccharides characterized by a disaccharide-repeat unit of a uronic acid [α-L-iduronic acid (I) or β-D-glucuronic acid (G)] linked 1,4 to α-D-hexosamine (H). HLGAGs are the most acidic, heterogeneous and information dense biopolymer found in nature due to the highly variable chemical modification of the disaccharide repeat unit—primarily in the form of sulfation at the N-, 3O and 6O positions of H, and the 2O of the uronic acids. Critically, HLGAGs (along with collagen) are key components of the cell surface-extracellular matrix (ECM) interface. While collagen-like proteins provide the necessary extracellular scaffold for cells to attach and form tissues, the complex polysaccharides fill the space created by the scaffold and act as a molecular sponge by specifically binding and regulating the biological activities of numerous signaling molecules like growth factors, cytokines etc. It has recently been recognized that cells synthesize distinct HLGAG sequences and decorate themselves with these sequences, using the extraordinary information content present in the sequences to bind specifically to many signaling molecules and thereby regulate various biological processes.

Tumor metastasis involves the spread of tumor cells primarily via the vasculature following the disassembly of tumor cell-ECM interactions through the degradation of the ECM, and tumor cell extravasation through the capillary bed. Recent evidence has suggested that collagen (and related proteins), enzymes (collagenases and others) that degrade the proteinaceous component of the ECM may play roles in the regulation of tumor angiogenesis or tumor cell invasion of the ECM. However, the chemical heterogeneity of complex polysaccharides and lack of effective tools, has seriously limited investigations into the roles of HLGAGs in tumor growth and metastasis. Interestingly, however, in parallel with collagen and the proteases, it has been hypothesized that HLGAG degrading enzymes (heparinases) assist in the breakdown of ECM to promote tumor growth, angiogenesis and metastasis. Other evidence such as the recent cloning of tumor heparinase genes has led to the paradigm that, the expression of HLGAG degrading enzymes represents a 'switch' from a primary tumor to a metastatic disease state.

In surprising contrast to the findings of the prior art, it has now been discovered according to the invention that not only is the prior art incorrect in stating that HLGAG degrading enzymes may contribute to tumor growth and metastasis, but in fact that certain HLGAG degrading enzymes and HLGAG fragments (including LMWH compositions generated by heparinase III), actually, are very effective in inhibiting cancer cell growth and metastasis. In particular, it has been discovered that heparinases having similar functional activity to native heparinase III prevent in vivo tumor growth and metastasis. It has also been discovered that the enzymatic products of heparinase III (HLGAG fragments and LMWH) are useful for preventing tumor growth and metastasis.

The Examples section provides in vitro and in vivo data demonstrating the effectiveness of the heparinases in preventing tumor growth and metastasis. Using two different animal models of cancer, B16BL6 and LLC, strikingly similar data was obtained, indicating an important role for HLGAGs in tumor growth and metastasis. The data also demonstrated the differential effects of heparinases I and III, and the HLGAG fragments generated by these heparinases on physiological processes. Heparinase I was unable to prevent cancer cell proliferation or metastasis, indicating that the effects are specific to heparinase III and functional variants thereof. These results are consistent with the unique specificities of heparinases, and hence the distinct oligosaccharide products they generate. Additionally, the data demonstrated that HLGAG fragments for one cell type were able to influence effects on another cell type, strongly indicating the involvement of specific sequences of HLGAG in modulating effects on tumor growth and metastasis.

Thus, the invention includes methods for treating or preventing tumor formation and/or metastasis by administering to a subject a heparinase III molecule (native or modified) and/or therapeutic HLGAG fragments (including LMWH).

The heparinases useful in this aspect of the invention include native heparinase III, modified heparinase III and modified heparinases having the functional activity of heparinase III. "Native heparinase III" as used herein refers to the naturally occurring heparinase III molecule in an isolated form. The sequence of the naturally occurring molecule from F. heparinum is provided as SEQ ID NO.: 1 (nucleic acid sequence) and 2 (amino acid sequence), and has been extensively described in art including in issued patents. An isolated molecule is a molecule that is substantially pure and is free of other substances with which it is ordinarily found in nature or in vivo systems to an extent practical and appropriate for its intended use. In particular, the molecular species are sufficiently pure and are sufficiently free from other biological constituents of host cells so as to be useful in, for example, producing pharmaceutical preparations or sequencing if the molecular species is a nucleic acid, peptide, or polysaccharide. Because an isolated molecular species of the invention may be admixed with a pharmaceutically-acceptable carrier in a pharmaceutical preparation, the molecular species may comprise only a small percentage by weight of the preparation. The molecular species is nonetheless substantially pure in that it has been substantially separated from the substances with which it may be associated in living systems.

A "modified heparinase III" as used herein is any heparinase III molecule which has at least one mutation, deletion or substitution, compared to native heparinase III but which retains the ability to enzymatically cleave heparan sulfate. These include the particular modified heparinases described herein as well as any other modified heparinase having the appropriate function. These can be identified by those of ordinary skill in the art using the methods described above or in the examples section. For instance, the modified heparinase III may have a simple conservative substitution within a region of the molecule which is not critical for enzymatic activity or folding and thus which has no effect on the ability of the heparinase to cleave the substrate. Additionally, substitutions such as the histidine substitutions described herein which influence the enzymatic activity or product profile of the heparinase but which still retain some enzymatic activity are also useful for this aspect of the invention because they are still able to cleave heparan sulfate. The two histidine mutations (His 295 and His 510) which lost all activity, however, are not useful in this aspect of the invention. (These two mutants have other utilities, such as competitive inhibitors.)

The term "modified heparinases having functional activity of heparinase III" as used herein refers to heparinases other than heparinase III which have been modified such that they are enzymatically active towards heparan sulfate but only have minimal or no activity towards heparin. For instance, mutation of $Cys^{348}$ of heparinase II, a residue which is involved in heparin binding, causes the heparinase II to have a reduced enzymatic activity with respect to heparin. This modification produces a modified heparinase II which becomes exclusively a heparan sulfate degrading enzyme. Additionally, when histidine 440 is mutated in heparinase III, a modified heparinase III is produced which has reduced enzymatic activity with respect to heparin but which displays nearly the same enzymatic activity as native heparinase III when heparan sulfate is used as the substrate. Mutation of histidines 451, 238, and 579 of heparinase II produces modified heparinase II molecules having reduced enzymatic activity with respect to heparan sulfate. Thus modified heparinase II molecules in which the $Cys^{348}$ or $His^{440}$ is mutated are "modified heparinases having functional activity of heparinase III" according to the invention, whereas heparinases in which histidines 451, 238, or 579 have been mutated are not within this class of molecules.

The invention also contemplates the use of therapeutic HLGAGs for the treatment and prevention of tumor cell proliferation and metastasis. A therapeutic HLGAG fragment as used herein refers to a molecule or molecules which are pieces or fragments of an HLGAG that have been identified through the use of the native heparinase III, modified heparinase III and modified heparinases having the functional activity of heparinase III described above. HLGAG fragments also include low molecular weight heparins (LMWHs). The compositional analysis of some therapeutic HLGAGs is described below in the Examples section.

The invention also encompasses screening assays for identifying therapeutic HLGAG fragments for the treatment of a tumor and for preventing metastasis. The assays are accomplished by treating a tumor or isolated tumor cells with heparinase III, native or modified and isolating the resultant HLGAG fragments. Surprisingly, these HLGAG fragments have therapeutic activity in the prevention of tumor cell proliferation and metastasis. As described in more detail in the Examples section, these HLGAG fragments are useful as therapeutic agents for the treatment of the tumor cells from which they were generated as well as other tumors. Thus the invention encompasses individualized therapies, in which a tumor or portion of a tumor is isolated from a subject and used to prepare the therapeutic HLGAG fragments. These therapeutic fragments can be re-administered to the subject to protect the subject from further tumor cell proliferation or metastasis or from the initiation of metastasis if the tumor is not yet metastatic. Alternatively the fragments can be used in a different subject having the same type or tumor or a different type of tumor.

The term "therapeutic HLGAG fragment" as used herein refers to an HLGAG which has therapeutic activity in that it prevents the proliferation and/or metastasis of a tumor cell. Such compounds can be generated using heparinase III to produce therapeutic fragments or they can be synthesized de novo. Putative HLGAG fragments can be tested for therapeutic activity using any of the assays described herein or known in the art. Thus the therapeutic HLGAG fragment may be a synthetic HLGAG fragment generated based on the sequence of the HLGAG fragment identified when the tumor is contacted with heparinase III, or having minor variations which do not interfere with the activity of the compound. Alternatively the therapeutic HLGAG fragment may be an isolated HLGAG fragment produced when the tumor is contacted with heparinase III.

The invention is useful for treating and/or preventing tumor cell proliferation or metastasis in a subject. The terms "prevent" and "preventing" as used herein refer to inhibiting completely or partially the proliferation or metastasis of a cancer or tumor cell, as well as inhibiting any increase in the proliferation or metastasis of a cancer or tumor cell.

A "subject having a cancer" is a subject that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

A "subject at risk of having a cancer" as used herein is a subject who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission. When a subject at risk of developing a cancer is treated with a heparinase III the subject may be able to kill the cancer cells as they develop.

Effective amounts of the native heparinase III, modified heparinases, or therapeutic HLGAGs of the invention are administered to subjects in need of such treatment. Effective amounts are those amounts which will result in a desired reduction in cellular proliferation or metastasis without causing other medically unacceptable side effects. Such amounts can be determined with no more than routine experimentation. It is believed that doses ranging from 1 nanogram/kilogram to 100 milligrams/kilogram, depending upon the mode of administration, will be effective. The absolute amount will depend upon a variety of factors (including whether the administration is in conjunction with other methods of treatment, the number of doses and individual patient parameters including age, physical condition, size and weight) and can be determined with routine experimentation. It is preferred generally that a maximum dose be used, that is, the highest safe dose according to sound medical judgment. The mode of administration may be any medically acceptable mode including oral, subcutaneous, intravenous, etc.

In some aspects of the invention the effective amount of heparinase III is that amount effective to prevent invasion of a tumor cell across a barrier. The invasion and metastasis of cancer is a complex process which involves changes in cell adhesion properties which allow a transformed cell to invade and migrate through the extracellular matrix (ECM) and acquire anchorage-independent growth properties. Liotta, L. A., et al., Cell 64:327–336 (1991). Some of these changes occur at focal adhesions, which are cell/ECM contact points containing membrane-associated, cytoskeletal, and intracellular signaling molecules. Metastatic disease occurs when the disseminated foci of tumor cells seed a tissue which supports their growth and propagation, and this secondary spread of tumor cells is responsible for the morbidity and mortality associated with the majority of cancers. Thus the term "metastasis" as used herein refers to the invasion and migration of tumor cells away from the primary tumor site.

The barrier for the tumor cells may be an artificial barrier in vitro or a natural barrier in vivo. In vitro barriers include but are not limited to extracellular matrix coated membranes, such as Matrigel. Thus the heparinase compositions can be tested for their ability to inhibit tumor cell invasion in a Matrigel invasion assay system as described in detail by Parish, C. R., et al., "A Basement-Membrane Permeability Assay which Correlates with the Metastatic Potential of Tumour Cells," Int. J. Cancer (1992) 52:378–383. Matrigel is a reconstituted basement membrane containing type IV collagen, laminin, heparan sulfate proteoglycans such as perlecan, which bind to and localize bFGF, vitronectin as well as transforming growth factor-$\beta$ (TGF-$\beta$), urokinase-type plasminogen activator (uPA), tissue plasminogen activator (tPA), and the serpin known as plasminogen activator inhibitor type 1 (PAI-1). Other in vitro and in vivo assays for metastasis have been described in the prior art, see, e.g., U.S. Pat. No. 5,935,850, issued on Aug. 10, 1999, which is incorporated by reference. An in vivo barrier refers to a cellular barrier present in the body of a subject.

In general, when administered for therapeutic purposes, the formulations of the invention are applied in pharmaceutically acceptable solutions. Such preparations may routinely contain pharmaceutically acceptable concentrations of salt, buffering agents, preservatives, compatible carriers, adjuvants, and optionally other therapeutic ingredients.

The compositions of the invention may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof and are not excluded from the scope of the invention. Such pharmacologically and pharmaceutically acceptable salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, pharmaceutically acceptable salts can be prepared as alkaline metal or alkaline earth salts, such as sodium, potassium or calcium salts of the carboxylic acid group.

Suitable buffering agents include: acetic acid and a salt (1–2% W/V); citric acid and a salt (1–3% W/V); boric acid and a salt (0.5–2.5% W/V); and phosphoric acid and a salt (0.8–2% W/V). Suitable preservatives include benzalkonium chloride (0.003–0.03% W/V); chlorobutanol (0.3–0.9% W/V); parabens (0.01–0.25% W/V) and thimerosal (0.004–0.02% W/V).

The present invention provides pharmaceutical compositions, for medical use, which comprise native heparinase III, modified heparinases of the invention, or therapeutic HLGAG fragments together with one or more pharmaceutically acceptable carriers and optionally other therapeutic ingredients. The term "pharmaceutically-acceptable carrier" as used herein, and described more fully below, means one or more compatible solid or liquid filler, diluents or encapsulating substances which are suitable for administration to a human or other animal. In the present invention, the term "carrier" denotes an organic or inorganic ingredient, natural or synthetic, with which the active ingredient is combined to facilitate the application. The components of the pharmaceutical compositions also are capable of being commingled with the modified heparinases of the present invention, and with each other, in a manner such that there is no interaction which would substantially impair the desired pharmaceutical efficiency.

A variety of administration routes are available. The particular mode selected will depend, of course, upon the particular modified heparinase selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. A preferred mode of administration is a parenteral route. The term "parenteral" includes subcutaneous injections, intravenous, intramuscular, intraperitoneal, intra sternal injection or infusion techniques. Other modes of administration include oral, mucosal, rectal, vaginal, sublingual, intranasal, intratracheal, inhalation, ocular, transdermal, etc.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527–1533, 1990, which is incorporated herein by reference.

The compositions may conveniently be presented in unit dosage form and may be prepared by any of the methods well known in the art of pharmacy. All methods include the step of bringing the active modified heparinase into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The polymer may be stored lyophilized.

Other delivery systems can include time-release, delayed release or sustained release delivery systems. Such systems can avoid repeated administrations of the heparinases of the invention, increasing convenience to the subject and the physician. Many types of release delivery systems are available and known to those of ordinary skill in the art. They include polymer based systems such as polylactic and polyglycolic acid, polyanhydrides and polycaprolactone; non-polymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. Nos. 4,748,034 and 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

A subject is any human or non-human vertebrate, e.g., dog, cat, horse, cow, pig.

When administered to a patient undergoing cancer treatment, the heparinase III compounds may be administered in cocktails containing other anti-cancer agents. The compounds may also be administered in cocktails containing agents that treat the side-effects of radiation therapy, such as anti-emetics, radiation protectants, etc.

Anti-cancer drugs that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma- I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

The heparinase III compounds may also be linked to a targeting molecule. A targeting molecule is any molecule or compound which is specific for a particular cell or tissue and which can be used to direct the heparinase III to the cell or tissue. Preferably the targeting molecule is a molecule which specifically interacts with a cancer cell or a tumor. For instance, the targeting molecule may be a protein or other type of molecule that recognizes and specifically interacts with a tumor antigen.

Tumor-antigens include Melan-A/M A RT -1, Dipeptidyl peptidase IV (DPPIV), adenosine deaminase-binding protein (ADAbp), cyclophilin b, Colorectal associated antigen (CRC)-C017-1A/GA733, Carcinoembryonic Antigen (CEA) and its immunogenic epitopes CAP-1 and CAP-2, etv6, aml1, Prostate Specific Antigen (PSA) and its immunogenic epitopes PSA-1, PSA-2, and PSA-3, prostate-specific membrane antigen (PSMA), T-cell receptor/CD3-zeta chain, MAGE-family of tumor antigens (e.g., MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-family of tumor antigens (e.g., GAGE-1, GAGE-2, GAGE-3, GAGE-4, GAGE-5, GAGE-6, GAGE-7, GAGE-8, GAGE-9), BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin and γ-catenin, p120ctn, gp100$^{Pmel117}$, PRAME, NY-ESO-1, brain glycogen phosphorylase, SSX-1, SSX-2 (HOM-MEL-40), SSX-1, SSX-4, SSX-5, SCP-1, CT-7, cdc27, adenomatous polyposis coli protein (APC), fodrin, P1A, Connexin 37, Ig-idiotype, p15, gp75, GM2 and GD2 gangliosides, viral products such as human papilloma virus proteins, Smad family of tumor antigens, lmp-1, EBV-encoded nuclear antigen (EBNA)-1, and c-erbB-2.

Examples of tumor antigens which bind to either or both MHC class I and MHC class II molecules, see the following references: Coulie, *Stem Cells* 13:393–403, 1995; Traversari et al., *J. Exp. Med.* 176:1453–1457, 1992; Chaux et al., *J. Immunol.* 163:2928–2936, 1999; Fujie et al., *Int. J. Cancer* 80:169–172, 1999; Tanzarella et al., *Cancer Res.* 59:2668–2674, 1999; van der Bruggen et al., *Eur. J. Immunol.* 24:2134–2140, 1994; Chaux et al., *J. Exp. Med.* 189:767–778, 1999; Kawashima et al, *Hum. Immunol.* 59:1–14, 1998; Tahara et al., *Clin. Cancer Res.* 5:2236–2241, 1999; Gaugler et al., *J. Exp. Med.* 179:921–930, 1994; van der Bruggen et al.,*Eur. J. Immunol.* 24:3038–3043, 1994; Tanaka et al., *Cancer Res.* 57:4465–4468, 1997; Oiso et al.,*Int. J. Cancer* 81:387–394, 1999; Herman et al., *Immunogenetics* 43:377–383, 1996; Manici et al., *J. Exp. Med.* 189:871–876, 1999; Duffour et al., *Eur. J. Immunol.* 29:3329–3337, 1999; Zom et al., *Eur. J. Immunol.* 29:602–607, 1999; Huang et al., *J. Immunol.* 162:6849–6854, 1999; Boël et al., *Immunity* 2:167–175, 1995; Van den Eynde et al., *J. Exp. Med.* 182:689–698, 1995; De Backer et al., *Cancer Res.* 59:3157–3165, 1999; Jäger et al.,*J. Exp. Med.* 187:265–270, 1998; Wang et al.,*J. Immunol.* 161:3596–3606, 1998; Aamoudse et al., *Int. J. Cancer* 82:442–448, 1999; Guilloux et al., *J. Exp. Med.* 183:1173–1183, 1996; Lupetti et al., *J. Exp. Med.* 188:1005–1016, 1998; Wölfel et al., *Eur. J. Immunol.* 24:759–764, 1994; Skipper et al., *J. Exp. Med.* 183:527–534, 1996; Kang et al., *J. Immunol.* 155:1343–1348, 1995; Morel et al., *Int. J. Cancer* 83:755–759, 1999; Brichard et al., *Eur. J. Immunol.* 26:224–230, 1996; Kittlesen et al., *J. Immunol.* 160:2099–2106, 1998; Kawakami et al., *J. Immunol.* 161:6985–6992, 1998; Topalian et al., *J. Exp. Med.* 183:1965–1971, 1996; Kobayashi et al., *Cancer Research* 58:296–301, 1998; Kawakami et al., *J. Immunol.* 154:3961–3968, 1995; Tsai et al., *J. Immunol.* 158:1796–1802, 1997; Cox et al., *Science* 264:716–719, 1994; Kawakami et al., *Proc. Natl. Acad Sci. USA* 91:6458–6462, 1994; Skipper et al., *J. Immunol.* 157:5027–5033, 1996; Robbins et al., *J. Immunol.* 159:303–308, 1997; Castelli et al, *J. Immunol.* 162:1739–1748, 1999; Kawakami et al., *J. Exp. Med.* 180:347–352, 1994; Castelli et al., *J. Exp. Med.* 181:363–368, 1995; Schneider et al., *Int. J. Cancer* 75:451–458, 1998; Wang et al., *J. Exp. Med.* 183:1131–1140, 1996; Wang et al., *J. Exp. Med.* 184:2207–2216, 1996; Parkhurst et al., *Cancer Research* 58:4895–4901, 1998; Tsang et al., *J. Natl Cancer Inst* 87:982–990, 1995; Correale et al., *J Natl Cancer Inst* 89:293–300, 1997; Coulie et al.,*Proc. Natl. Acad. Sci. USA* 92:7976–7980, 1995; Wölfel et al.,*Science* 269:1281–1284, 1995; Robbins et al., *J. Exp. Med.* 183:1185–1192, 1996; Brändle et al.,*J. Exp. Med.* 183:2501–2508, 1996; ten Bosch et al., *Blood* 88:3522–3527, 1996; Mandruzzato et al., *J. Exp. Med.* 186:785–793, 1997; Guéguen et al.,*J. Immunol.* 160:6188–6194, 1998; Gjertsen et al., *Int. J. Cancer* 72:784–790, 1997; Gaudin et al., *J. Immunol.* 162:1730–1738, 1999; Chiari et al., *Cancer Res.* 59:5785–5792, 1999; Hogan et al., *Cancer Res.* 58:5144–5150, 1998; Pieper et al., *J. Exp. Med.* 189:757–765, 1999; Wang et al., *Science* 284:1351–1354, 1999; Fisk et al., *J. Exp. Med.* 181:2109–2117, 1995; Brossart et al., *Cancer Res.* 58:732–736, 1998; Röpke et al., *Proc. Natl. Acad. Sci.* USA 93:14704–14707, 1996; Ikeda et al., *Immunity* 6:199–208, 1997; Ronsin et al., *J. Immunol.* 163:483–490, 1999; Vonderheide et al., *Immunity* 10:673–679,1999. These antigens as well as others are disclosed in PCT Application PC/US98/18601.

One of ordinary skill in the art, in light of the present disclosure, is enabled to produce substantially pure preparations of any of the native or modified heparinases by standard technology, including recombinant technology, direct synthesis, mutagenesis, etc. For instance, using recombinant technology one may substitute appropriate codons in SEQ ID NO: 1 to produce the desired amino acid substitutions by standard site-directed mutagenesis techniques. Obviously, one may also use any sequence which differs from SEQ ID NO: 1 only due to the degeneracy of the genetic code as the starting point for site directed mutagenesis. The mutated nucleic acid sequence may then be ligated into an appropriate expression vector and expressed in a host such as *F. heparinum* or *E. coli*. The resultant modified heparinase may then be purified by techniques well known in the art, including those disclosed below and in Sasisekharan, et al. (1993). As used herein, the term "substantially pure" means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations.

In another set of embodiments an isolated nucleic acid encoding the substantially pure modified heparinase of the invention is provided. As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein the coding sequences are operably joined to regulatory sequences. Two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Promoters may be constitutive or inducible. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium, or just a single time per host as the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

As used herein, the term "stringent conditions" refers to parameters known to those skilled in the art. One example of stringent conditions is hybridization at 65° C. in hybridization buffer (3.5×SSC, 0.02% Ficoll, 0.02% polyvinyl pyrolidone, 0.02% bovine serum albumin (BSA), 25 mM $NaH_2PO_4$ (pH7), 0.5% SDS, 2 mM EDTA). SSC is 0.15M sodium chloride/0.15M sodium citrate, pH7; SDS is sodium dodecylsulphate; and EDTA is ethylene diamine tetra acetic acid. There are other conditions, reagents, and so forth which can be used, which result in the same degree of stringency. A skilled artisan will be familiar with such conditions, and thus they are not given here. The skilled artisan also is familiar with the methodology for screening cells for expression of such molecules, which then are routinely isolated, followed by isolation of the pertinent nucleic acid. Thus, homologs and alleles of the substantially pure modified heparinases of the invention, as well as nucleic acids encoding the same, may be obtained routinely, and the invention is not intended to be limited to the specific sequences disclosed.

For prokaryotic systems, plasmid vectors that contain replication sites and control sequences derived from a species compatible with the host may be used. Examples of suitable plasmid vectors include pBR322, pUC18, pUC19 and the like; suitable phage or bacteriophage vectors include λgt10, λgt11 and the like; and suitable virus vectors include pMAM-neo, pKRC and the like. Preferably, the selected vector of the present invention has the capacity to autonomously replicate in the selected host cell. Useful prokaryotic hosts include bacteria such as *E. coli, Flavobacterium heparinum, Bacillus, Streptomyces, Pseudomonas, Salmonella, Serratia*, and the like.

To express the substantially pure modified heparinases of the invention in a prokaryotic cell, it is necessary to operably join the nucleic acid sequence of a substantially pure modified heparinase of the invention to a functional prokaryotic promoter. Such promoter may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, and the like. Examples of inducible prokaryotic promoters include the major right and left promoters of bacteriophage λ ($P_L$ and $P_R$), the trp, recA, lacZ, lacI, and gal promoters of *E. coli*, the α-amylase (Ulmanen et al., *J. Bacteriol.* 162:176–182 (1985)) and the ζ-28-specific promoters of *B subtilis* (Gilman et al., *Gene sequence* 32:11–20 (1984)), the promoters of the bacteriophages of Bacillus (Gryczan, In: *The Molecular Biology of the Bacilli*, Academic Press, Inc., NY (1982)), and Streptomyces promoters (Ward et al., *Mol. Gen. Genet.* 203:468–478 (1986)).

Prokaryotic promoters are reviewed by Glick (*J. Ind. Microbiol.* 1:277–282 (1987)); Cenatiempo (*Biochimie* 68:505–516 (1986)); and Gottesman (*Ann. Rev. Genet.* 18:415–442 (1984)).

Proper expression in a prokaryotic cell also requires the presence of a ribosome binding site upstream of the encoding sequence. Such ribosome binding sites are disclosed, for example, by Gold et al. (*Ann. Rev. Microbiol.* 35:365–404 (1981)).

Because prokaryotic cells will not produce the modified heparinases of the invention with normal eukaryotic glycosylation, expression of the modified heparinases of the invention of the invention by eukaryotic hosts is possible when glycosylation is desired. Preferred eukaryotic hosts include, for example, yeast, fungi, insect cells, and mammalian cells, either in vivo or in tissue culture. Mammalian cells which may be useful as hosts include HeLa cells, cells of fibroblast origin such as VERO or CHO-K1, or cells of lymphoid origin, such as the hybridoma SP2/0-AG14 or the myeloma P3x63Sg8, and their derivatives. Preferred mammalian host cells include SP2/0 and J558L, as well as neuroblastoma cell lines such as IMR 332 that may provide better capacities for correct post-translational processing. Embryonic cells and mature cells of a transplantable organ also are useful according to some aspects of the invention.

In addition, plant cells are also available as hosts, and control sequences compatible with plant cells are available, such as the nopaline synthase promoter and polyadenylation signal sequences.

Another preferred host is an insect cell, for example in *Drosophila* larvae. Using insect cells as hosts, the *Drosophila* alcohol dehydrogenase promoter can be used (Rubin, *Science* 240:1453–1459 (1988)). Alternatively, baculovirus vectors can be engineered to express large amounts of the modified heparinases of the invention in insects cells (Jasny, *Science* 238:1653 (1987); Miller et al., In: *Genetic Engineering* (1986), Setlow, J. K., et al., eds., Plenum, Vol. 8, pp. 277–297).

Any of a series of yeast gene sequence expression systems which incorporate promoter and termination elements from the genes coding for glycolytic enzymes and which are produced in large quantities when the yeast are grown in media rich in glucose may also be utilized. Known glycolytic gene sequences can also provide very efficient transcriptional control signals. Yeast provide substantial advantages in that they can also carry out post-translational peptide modifications. A number of recombinant DNA strategies exist which utilize strong promoter sequences and high copy number plasmids which can be utilized for production of the desired proteins in yeast. Yeast recognize leader sequences on cloned mammalian gene sequence products and secrete peptides bearing leader sequences (i.e., prepeptides).

A wide variety of transcriptional and translational regulatory sequences may be employed, depending upon the nature of the host. The transcriptional and translational regulatory signals may be derived from viral sources, such as adenovirus, bovine papilloma virus, simian virus, or the like, where the regulatory signals are associated with a particular gene sequence which has a high level of expression. Alternatively, promoters from mammalian expression products, such as actin, collagen, myosin, and the like, may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or which are subject to chemical (such as metabolite) regulation.

As discussed above, expression of the modified heparinases of the invention in eukaryotic hosts requires the use of eukaryotic regulatory regions. Such regions will, in general, include a promoter region sufficient to direct the initiation of RNA synthesis. Preferred eukaryotic promoters include, for example, the promoter of the mouse metallothionein I gene sequence (Hamer et al., *J. Mol. Appl. Gen.* 1:273–288 (1982)); the TK promoter of Herpes virus (McKnight, *Cell* 31:355–365 (1982)); the SV40 early promoter (Benoist et al., *Nature (London)* 290:304–310 (1981)); the yeast gal4 gene sequence promoter (Johnston et al., *Proc. Natl. Acad. Sci. (USA)* 79:6971–6975 (1982); Silver et al., *Proc. Natl. Acad. Sci. (USA)* 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes the modified heparinases of the invention does not contain any intervening codons which are capable of encoding a methionine (i.e., AUG). The presence of such codons results either in the formation of a fusion protein (if the AUG codon is in the same reading frame as the modified heparinases of the invention coding sequence) or a frame-shift mutation (if the AUG codon is not in the same reading frame as the modified heparinases of the invention coding sequence).

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may, for example, provide for prototrophy to an auxotrophic host or may confer biocide resistance to, e.g., antibiotics, heavy metals, or the like. The selectable marker gene sequence can either be directly linked to the DNA gene sequences to be expressed, or introduced into the same cell by co-transfection. Additional elements may also be needed for optimal synthesis of the modified heparinases of the invention mRNA. These elements may include splice signals, as well as transcription promoters, enhancers, and termination signals. cDNA expression vectors incorporating such elements include those described by Okayama, *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species. Preferred prokaryotic vectors include plasmids such as those capable of replication in *E. coli* (such as, for example, pBR322, ColE1, pSC101, pACYC 184, and πVX. Such plasmids are, for example, disclosed by Sambrook, et al. (*Molecular Cloning: A Laboratory Manual*, second edition, edited by Sambrook, Fritsch, & Maniatis, Cold Spring Harbor Laboratory, 1989)). *Bacillus* plasmids include pC194, pC221, pT127, and the like. Such plasmids are disclosed by Gryczan (In: *The Molecular Biology of the Bacilli*, Academic Press, NY (1982), pp. 307–329). Suitable *Streptomyces* plasmids include pIJ101 (Kendall et al., *J. Bacteriol.* 169:4177–4183 (1987)), and *streptomyces* bacteriophages such as φC31 (Chater et al., In: *Sixth International Symposium on Actinomycetales Biology*, Akademiai Kaido, Budapest, Hungary (1986), pp. 45–54). Pseudomonas plasmids are reviewed by John et al. (*Rev. Infect. Dis.* 8:693–704 (1986)), and Izaki (*Jpn. J. Bacteriol.* 33:729–742 (1978)).

Preferred eukaryotic plasmids include, for example, BPV, EBV, SV40, 2-micron circle, and the like, or their derivatives. Such plasmids are well known in the art (Botstein et al., *Miami Wntr. Symp.* 19:265–274 (1982); Broach, In: *The Molecular Biology of the Yeast Saccharomyces: Life Cycle and Inheritance*, Cold Spring Harbor Laboratory, Cold Spring Harbor, N.Y., p. 445–470 (1981); Broach, *Cell* 28:203–204 (1982); Bollon et al., *J. Clin. Hematol. Oncol.* 10:39–48 (1980); Maniatis, In: *Cell Biology: A Comprehensive Treatise*, Vol. 3, Gene Sequence Expression, Academic Press, NY, pp. 563–608 (1980)). Other preferred eukaryotic vectors are viral vectors. For example, and not by way of limitation, the pox virus, herpes virus, adenovirus and various retroviruses may be employed. The viral vectors may include either DNA or RNA viruses to cause expression of the insert DNA or insert RNA. Additionally, DNA or RNA encoding the modified heparinases of the invention polypeptides may be directly injected into cells or may be impelled through cell membranes after being adhered to microparticles.

Once the vector or DNA sequence containing the construct(s) has been prepared for expression, the DNA construct(s) may be introduced into an appropriate host cell by any of a variety of suitable means, i.e., transformation, transfection, conjugation, protoplast fusion, electroporation, calcium phosphate-precipitation, direct microinjection, and the like. After the introduction of the vector, recipient cells are grown in a selective medium, which selects for the growth of vector-containing cells. Expression of the cloned gene sequence(s) results in the production of the modified heparinases of the invention. This can take place in the transformed cells as such, or following the induction of these cells to differentiate (for example, by administration of bromodeoxyuracil to neuroblastoma cells or the like).

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Materials and Methods

Chemicals and Materials. Hydroxylamine hydrochloride and urea were from EM Science (Gibbstown, N.J.). The chemical modification reagent diethylpyrocarbonate (DEPC) was purchased from Sigma and used as received (Milwaukee, Wis.). Heparan sulfate was purchased from Celsus Laboratories (Cincinnati, Ohio). Lys-C from *Lysobacter enzymogenes* (EC 3.4.21.50) was from Roche Molecular Biochemicals (Indianapolis, Ind.). Heparinase III from *Flavobacterium heparinum* (EC 4.2.2.8) was purified as described previously (Godavarti, R., Cooney, C. L., Langer, R., and Sasisekharan, R. (1996) *Biochemistry* 35, 6846–52 and Lohse, D. and Linhardt, R. J. (1992) *J. Biol. Chem.* 267, 781–87) and was a gift from IBEX Technologies (Montreal, Canada).

Heparinase III Activity Assay

The activity of heparinase III was measured using a UV 232 nm assay similar to those reported for heparinase I and heparinase II (Godavarti, R., Cooney, C. L., Langer, R., and Sasisekharan, R. (1996) *Biochemistry* 35, 6846–52; Shriver, Z., Hu, Y., and Sasisekharan, R. (1998) *J. Biol. Chem.* 273, 10160–67; and Lohse, D. and Linhardt, R. J. (1992) *J. Biol. Chem.* 267, 781–87). Briefly, the increase in absorbance at 232 nm as a function of time was monitored under saturating substrate conditions. All assays were performed with heparan sulfate at a concentration of 2 mg/ml in 50 mM sodium phosphate, pH 7.6. The temperature for enzymatic activity measurements was kept constant at 35° C.

Chemical Modification of Heparinase III with DEPC (A) DEPC Inactivation of Heparinase III. At pH values ranging from 6.0 to 8.0, heparinase III (50 µg/mL) was incubated with DEPC in 50 mM sodium phosphate buffer at 25° C. The DEPC stock solution (6.9 M) was diluted with ethanol. Control reactions contained an equivalent amount of ethanol instead of DEPC and were found to not affect enzymatic activity over the experimental time range. At each pH, three reactions were run using different concentrations of DEPC, ranging from 50 µM to 2.5 mM. At fixed time intervals, 25 µL aliquots were withdrawn from the reaction mixtures for the UV 232 nm activity assay.

The kinetics of DEPC inactivation of heparinase III was determined by plotting the natural log of percent activity versus an adjusted time term (to account for the decomposition of DEPC). Briefly, this adjusted time term (t') was calculated according to the following equation:

$$t' = \frac{1 - e^{k't}}{k'}$$

In this equation, k' is the first order rate constant for DEPC hydrolysis and t is the measured time after addition of DEPC to the heparinase III solution. At each pH, the order of the reaction in DEPC was determined by plotting the observed rate constants of inactivation at each pH vs. log [DEPC]. The slope of this graph is n, the order of the reaction with respect to DEPC (Lundblad, R. (1995) *Techniques in Protein Modification*, CRC Press, Boca Raton).

(B) Reactivation of DEPC—Modified Enzyme with Hydroxylamine. Similar to what was completed with heparinase I and II (Godavarti, R., Cooney, C. L., Langer, R., and Sasisekharan, R. (1996) *Biochemistry* 35, 6846–52 and Shriver, Z., Hu, Y., and Sasisekharan, R. (1998) *J. Biol. Chem.* 273, 10160–67), heparinase III (50 µg/mL) was incubated with 0.97 mM DEPC, pH 6.5 until its enzymatic activity was reduced to 50% of its initial value. Hydroxylamine was then immediately added to the reaction mixture to a final concentration of 0.5 M. The reaction was incubated at room temperature for 6 hours. Aliquots were withdrawn every hour for the activity assay. The control mixture contained no DEPC but the same concentration of hydroxylamine to account for the loss of nonspecific activity. The ratio of the activity of the reaction mixture over the activity of the control was calculated to determine recovery of enzymatic activity.

(C) Substrate Protection of Heparinase III against DEPC Inactivation. Heparinase III (50 µg/mL) was pre-incubated with 2 mg/mL heparan sulfate in 50 mM sodium phosphate, pH 7.6 for 30 minutes prior to the addition of 1.5 mM DEPC. A control reaction with no prior incubation of substrate was also completed. The time course of inactivation for both was determined using the heparinase III activity assay.

(D) Quantification of the Number of Histidines Modified by DEPC. The extent of modification of an enzyme by DEPC can be determined by monitoring the formation of the N-carbethoxylhistidyl adduct at 240 nm. At time zero, 1.5 mM DEPC was added to the cuvette containing heparinase III in sodium phosphate buffer, pH 7.0. The change in absorbance at 240 nm was monitored every minute for 10 min. The number of modified residues was determined using a molar extinction coefficient of 3,200 $M^{-1}cm^{-1}$ (Lundblad, R. (1995) *Techniques in Protein Modification*, CRC Press, Boca Raton).

Peptide Mapping Studies

To determine which histidine residues were modified by DEPC, mapping studies using the protease Lys-C were completed. Heparinase III (1 nmole) was incubated with 4 mM DEPC for fifteen minutes, denatured with 6.5 M urea at 55° C. and diluted with water. Subsequently, the denatured, modified heparinase III was digested with Lys-C.

Peptides derived from heparinase III digestion were separated by reverse phase high performance liquid chromatography (RPHPLC) and monitored at 210, 277, and 240 nm. Peptide peaks not present in the control digest were collected and sequenced using an Applied Biosystems Sequencer model 477 with an on-line model 120 PTH amino acid analyzer (Biopolymers Laboratory, MIT).

Site-directed Mutagenesis

Each of the thirteen histidine residues of heparinase III was mutated to alanine using overlap extension PCR for 15 cycles (Higuchi, R. (1990) in *PCR Protocols. A Guide to Methods and Applications* (Innis, M., Gelfand, D. H., Sninsky, J. J., and White, T. J., Ed.) pp 177–83, Academic Press, San Diego). The PCR reactions were separated on a low-melt Agarose gel and the band corresponding to the proper molecular weight was excised. The DNA was extracted from the gel using a Gel Purification Kit (QIAGEN, Valencia, Calif.) and the insert was subcloned into pCR 2.1 (Invitrogen, Carlsbad, Calif.). The validity of all the point mutations and the integrity of the rest of the gene were verified by sequencing. The thirteen mutant heparinase III sequences were prepared in pCR2. 1 using a Miniprep kit (QIAGEN, Valencia, Calif.) and cloned using Nde I/BamH I (New England Biolabs, Beverly, Mass.) into pET-15b (Novagen, Madison, Wis.) for expression. The pET-15b plasmid contains a $NH_2$-terminal His-Tag for $Ni^{2+}$-column purification. Recombinant heparinase III was also expressed and compared to the native heparinase III isolated directly from *Flavobacterium heparinum*.

Expression, Isolation, and Purification of r-heparinase III and Mutants in *E. coli*

Overnight cultures of Luria-Bertani (LB) broth (5 ml) containing 0.02 mg/ml ampicillin (amp) were used to inoculate 500 ml LB/amp cultures at an initial $OD_{600}$ of 0.1. The cultures were induced with 1 mM isopropyl-B-D-thiogalactopyranoside (IPTG) in mid-log phase ($OD_{600}$ 0.7–0.9) and incubated for another hour at 37° C. To harvest the cells, the cultures were spun at 5,000 rpm and the supernatant was discarded.

The cell pellet was re-suspended in 20 mM Tris, 500 mM NaCl, 5 mM immidazole-HCl, pH 7.9 (1/50 of the initial culture volume). The re-suspended cells were placed on ice and sonicated as described previously (Ernst, S., Venkataraman, G., Winkler, S., Godavarti, R., Langer, R., Cooney, C. L., and Sasisekharan, R. (1996) *Biochem. J.* 315, 589–97). The soluble protein of the cell lysate was isolated by centrifugation at 12,000 rpm for 20 min. at 4° C. The supernant was filtered through a 0.45 µm filter and loaded onto a nickel column using a Biocad Perfusion Chromatography system (PerSeptive Biosystems, Framingham, Mass.). The column was washed and the protein was subsequently eluted in 20 mM Tris, 500 mM NaCl, 500 mM immidazole-HCl, pH 7.9. SDS-polyacrylamide gel electrophoresis analysis using precast 12% gels, the Mini-Protean II apparatus, and the Silver Stain Pus kit (Bio-Rad, Hercules, Calif.) was performed to determine the concentration and purity of the individual proteins.

HPLC Analysis of Saccharide Products of Heparinase III Activity

Exhaustive digests of 3 mg/ml heparan sulfate in 50 mM sodium phosphate buffer, pH 7.6 were performed overnight at 37° C. for each of the mutants (20 µg protein). The reactions were loaded onto a Spherisorb S5 SAX column (Waters) and eluted using a linear gradient of 0.2–1.0 M NaCl, pH 3.5. The products were monitored at 232 nm and each of the major peaks was collected. To determine their composition, the collected fractions were analyzed by capillary electrophoresis and identified by comigration with known standards.

Circular Dichroism (CD)

Recombinantly expressed heparinase III and the heparinase III mutants, H295A and H510A were concentrated and buffer-exchanged into 50 mM sodium phosphate, pH 7.0 using a Centricon 30 Filter (Millipore, Watertown, Mass.). CD spectra were collected on an Aviv 62DS spectropolarimeter equipped with a thermostatic temperature controller and interfaced to an IBM microcomputer. Measurements were performed in a quartz cell with a 1 mm path length. Spectra were recorded at 25° C., in an average of 10 scans between 205 and 260 nm, with a 1.0 nm bandwidth and a scan rate of 3 nm/min. CD band intensities are expressed as molar ellipticities, $\theta_M$, in degrees·$cm^2$·$dmol^{-1}$.

Transfection of B16 cells:

B16BL6 melanoma cells were transfected with antisense 2OST in pcDNA3.1. Stable transfectant clones were selected with G418 and propagated. The success of transfection was confirmed with PCR screening of transfected cells.

In vitro invasion assay:

$10^5$ of B16BL6 and B16BL6 transfectant were loaded onto inserts coated with 15 ug of Matrigel. MEM-α with 40 ng/ml of bFGF was used as chemoattractant. After 20 hours incubation at 37° C., inserts were fixed and stained. Unmigrated cells were removed and migrated cells were counted under light microscope.

In vivo primary tumor growth:

$4 \times 10^5$ B16BL6, transfected and untransfected respectively, were inoculated subcutaneously to the flank of nude mice. Measurement of tumor size started on day 10 after tumor cell injection. and mice were euthanized on day 16 after the injection.

In vivo lung metastasis:

$2 \times 10^5$ B16BL6 in 0.2 ml PBS, transfected and untransfected respectively, were injected via tail vein of C57BL6 mice. 13 days later, the mice were euthanized, lungs harvested and analyzed.

Compositional Analysis of HLGAGs resulting from heparinase treatment of B16 cells:

B16 cells were treated with either heparinase I, III or PBS. The supernatant was collected, boiled, and filtered through a 0.45 µm filter. This sample was then subjected to fractionation using a centricon spin column with a nominal molecular weight cutoff of 5 kDa. The retentate was exchanged into water and concentrated 50-fold by lyophilization.

Compositional analysis of oligosaccharides was completed by exhaustive digest of the high molecular weight fraction with heparinases I–III. To 9 µL of aqueous oligosaccharide was added 1 mU of heparinases I–III in 25 mM sodium acetate, 2 mM calcium chloride buffer at pH 7.0. The reaction was allowed to proceed at 37° C. overnight after which CE analysis was completed.

Compositional analysis was completed on a Hewlett Packard 3D CE unit by using uncoated fused silica capillaries (i.d. 75 µM). Analytes were measured using an extended path length capillary. The electrolyte was 50 mM tris/phosphate pH 2.5. Separations were carried out at 30 kV with reverse polarity. Assignments and quantification of disaccharides were made by comparison with known standards.

Results

Example 1
DEPC Inactivates Heparinase III

As a first step towards identifying histidines that are critical for the enzymatic activity of heparinase III, the effect of the modification reagent DEPC on the enzymatic activity of heparinase III was determined. DEPC is a common reagent used for the determination of catalytically critical histidines in enzymes. As stated in early publications (Godavarti, R., Cooney, C. L., Langer, R., and Sasisekharan, R. (1996) *Biochemistry* 35, 6846–52 and Shriver, Z., Hu, Y., and Sasisekharan, R. (1998) *J. Biol. Chem.* 273, 10160–67), DEPC is useful for the determination of catalytically critical histidines, however care needs to be taken to ensure that other nucleophilic residues, namely tyrosines, lysines, and cysteines are not modified.

Heparinase III was incubated with 0.31 (□), 0.54 (●), 0.97 (○), 1.5 (▲), 1.9 (Δ) mM DEPC at pH 6.5 and at 25°

C. (shown in inset of FIG. 1). The natural log of the percent activity remaining was plotted versus an adjusted time term (t') to account for the decomposition of DEPC. The slope of each of the lines at the various DEPC concentrations represents the pseudo-first order rate constants of inactivation. Plotting these pseudo-first order rate constants versus the respective DEPC concentrations yields a second-order rate constant of inactivation of 0.20±0.04 mM$^{-1}$min$^{-1}$.

For heparinase III, similar to heparinase I and II, DEPC was found to inhibit in a dose-dependent fashion. A measured second order rate constant of 0.20±0.04 min$^{-1}$mM$^{-1}$ is obtained by varying the concentration of the inhibitor. Consistent with this reaction being first order in both heparinase III and DEPC, a plot of $k_{inact}$ vs. log [DEPC] yielded a line with a slope of 1 (FIG. 1).

The fact that DEPC inactivates heparinase III in a pseudo-first order, dose-dependent manner suggests that DEPC is directly modifying a residue involved in the catalytic degradation of heparan sulfate. The second-order rate constant of inactivation (0.20±0.04 min$^{-1}$mM$^{-1}$) also suggests that DEPC is a potent inhibitor of heparinase III function.

To ensure that the interaction of DEPC with heparinase III is through histidine modification, we investigated whether other nucleophilic amino acids of heparinase III interact with DEPC. First, unlike with heparinase I or II, there is no possibility for cysteine modification since heparinase III contains no cysteines in its primary amino acid sequence. Furthermore, there was no loss of absorbance at 278 nm upon incubation of DEPC with heparinase III as would be expected if tyrosines were modified. Finally, addition of hydroxylamine to DEPC-modified heparinase III reversed most of the inactivation indicating that strongly nucleophilic residues, such as lysine, were not modified by DEPC (Table 1).

TABLE 1

Hydroxylamine Reversibility of DEPC Inactivation.

| Time (min) | Activity (%) |
|---|---|
| 0 | 51 |
| 30 | 60 |
| 60 | 66 |
| 90 | 72 |
| 180 | 76 |
| 240 | 78 |
| 360 | 80 |

Figure 2:
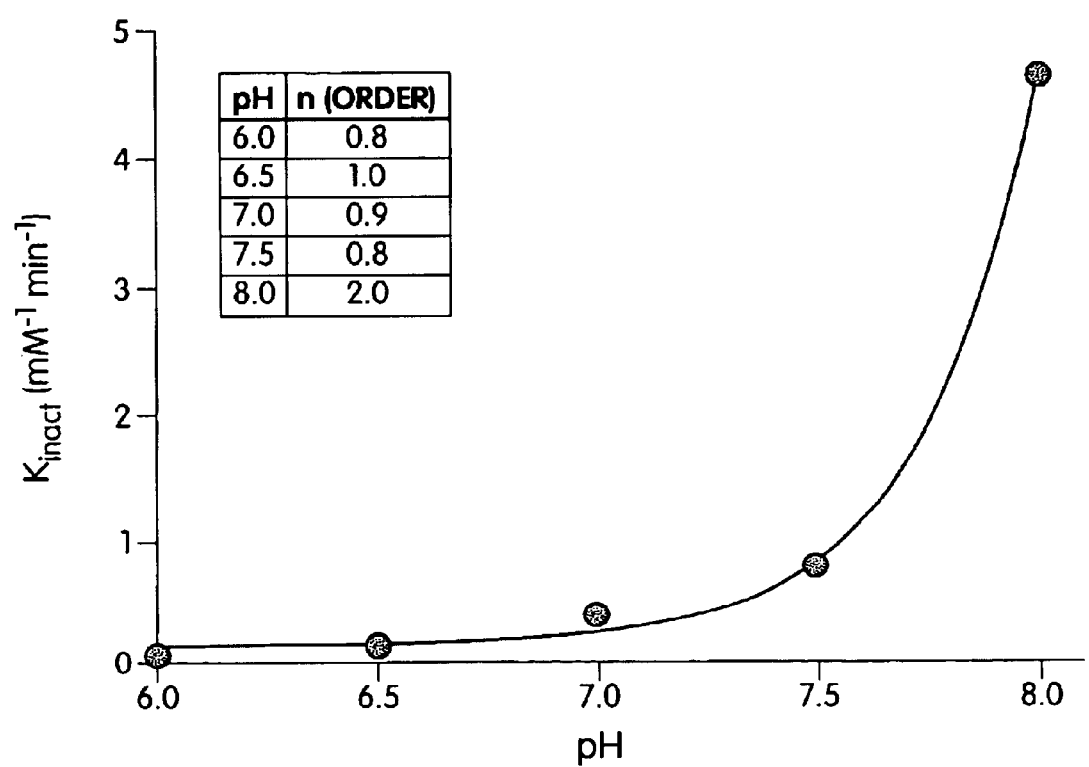
FIG. 2 is a graph depicting the pH dependence of the second order rate constant of inactivation upon incubation of heparinase III with varying concentrations of DEPC.

In an attempt to further define the interaction of DEPC with the histidines of heparinase III, the effect of the pH on the inactivation kinetics was examined. Examination of the rate of inactivation as a function of pH has been used to derive a pKa for a modified residue, since, in the case of histidine, the unprotonated form is much more readily modified than is the protonated form. The pH dependence of the second-order rate constant of inactivation is shown in FIG. 2. (Heparinase III was incubated with 50 μM to 2.5 mM DEPC at pH's 6.0–8.0 at 25° C. and the second-order rate constant of inactivation was calculated for each pH). With heparinase III, increasing the pH of the reaction from 6.0–7.5 results in an increase in the inactivation kinetics without changing the order of the reaction (FIG. 2). However, at pH 8.0 and higher, the reaction is no longer first order in DEPC, indicating other residues (possibly lysines) are interacting with DEPC at this pH. Consistent with this interpretation, hydroxylamine is no longer able to reverse inaction at pH 8.0. Therefore, the mapping studies and substrate protection experiments discussed below were conducted at pH 7.0 which maximized the reactivity while ensuring that only histidines were the target of DEPC modification.

Figure 3:
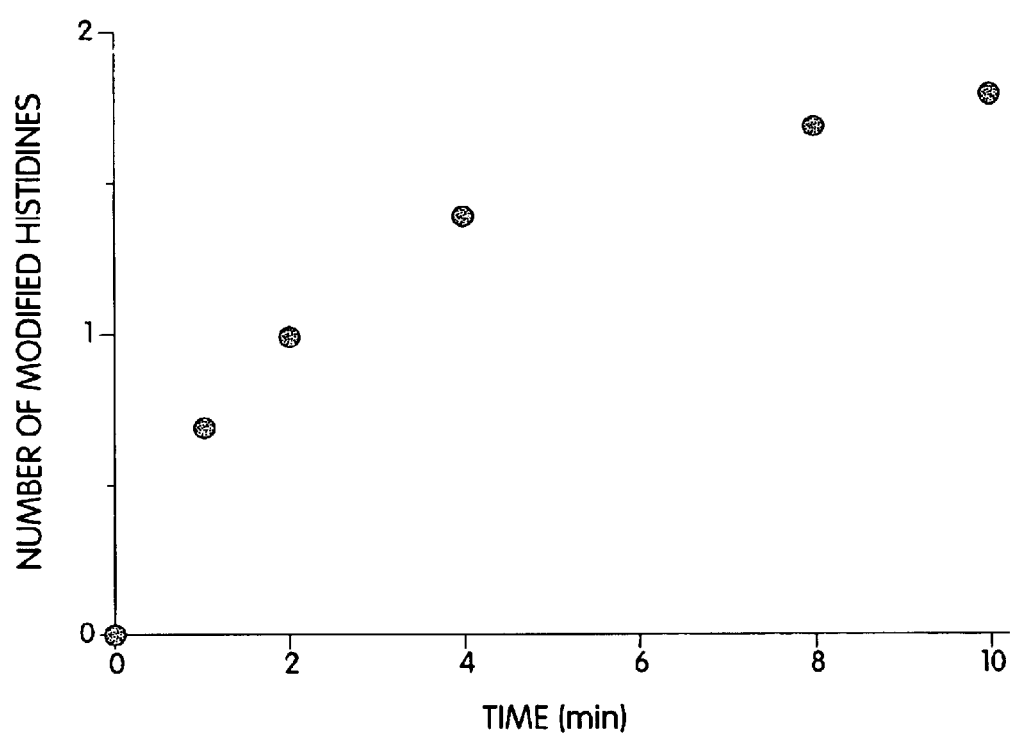
FIG. 3 is a graph depicting the quantification of DEPC-modified histidine residues in heparinase III over a period of time.

DEPC-modified histidine residues in heparinase III were quantified (shown in FIG. 3). At time zero, 1.5 mM DEPC was added to a cuvette containing heparinase III (540 μg/mL) in sodium phosphate buffer, pH 7.0. The change in absorbance at 240 nm was monitored at time intervals for 10 min. The number of modified histidines was calculated using a $\epsilon=3200$ M$^{-1}$cm$^{-1}$. At the beginning and end of the experiment, aliquots of heparinase III were withdrawn and tested for activity. Less than 5% of initial activity remained after 10 minutes incubation with DEPC.

Consistent with the idea that DEPC is interacting with a histidine residue in heparinase III, there is an increase in absorbance at 240 nm as a function of time, resulting from N-carbethoxyhistdyl derivatives. FIG. 3 shows the quantitation of the number of modified histidines. Over the course of 10 minutes, 1.8 histidines were modified per enzyme molecule resulting in a loss of greater than 90% activity. Thus, it appears that one or possibly two histidines, modified by DEPC, result in loss of enzymatic activity for heparinase III.

Figure 4:
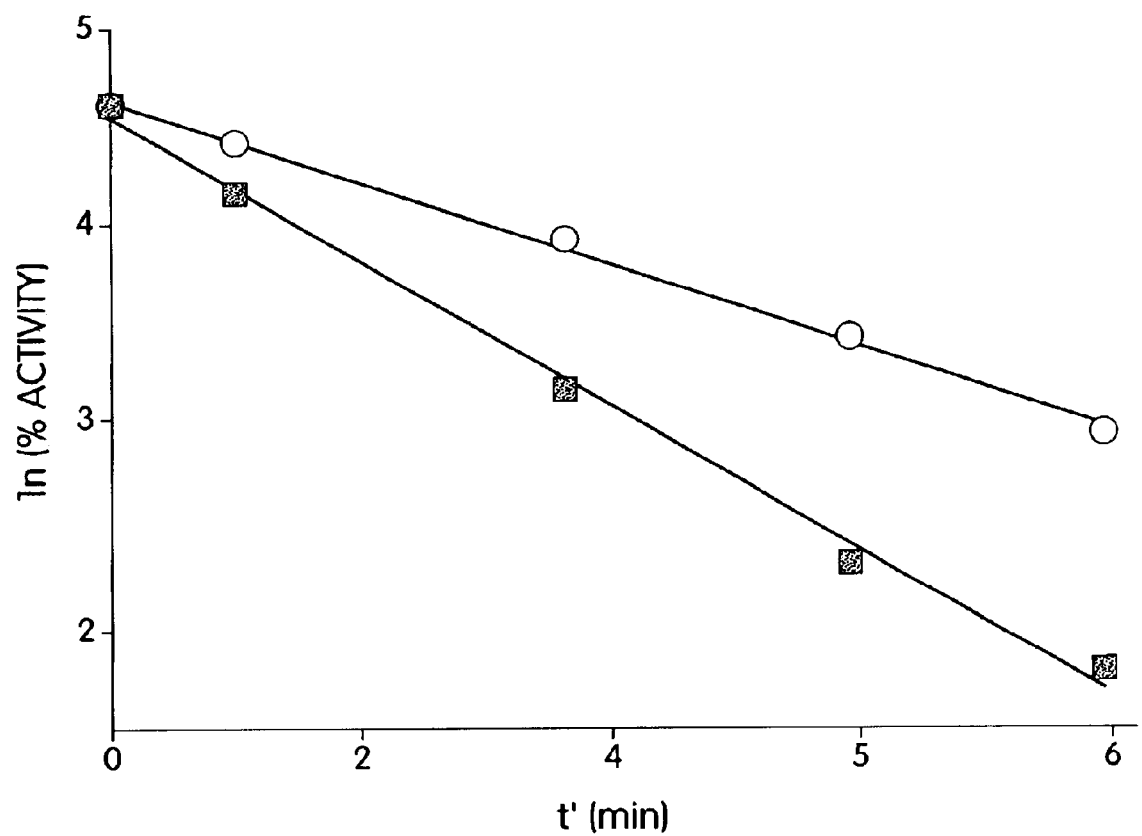
FIG. 4 is a graph depicting the substrate protection of heparinase III inactivation by DEPC.

Substrate protection of heparinase III inactivation by DEPC was also assessed (FIG. 4). Heparinase III (50 μg/mL) was incubated with 2 mg/mL heparan sulfate for 30 min. 1.5 mM DEPC was added to the reaction and time course of inactivation was completed using the heparinase III activity assay (○). A control reaction without preincubation with heparan sulfate was also done (□).

Preincubation of heparinase III with heparan sulfate substrate before addition of DEPC resulted in lower inactivation kinetics (FIG. 4) suggesting that the histidine(s) modified by DEPC are proximate to the substrate binding and/or active site of heparinase III, similar to what was observed for heparinase I and II (Godavarti, R., Cooney, C. L., Langer, R., and Sasisekharan, R. (1996) *Biochemistry* 35, 6846–52 AND Shriver, Z., Hu, Y., and Sasisekharan, R. (1998) *J. Biol. Chem.* 273, 10160–67).

Example 2

Peptide Mapping of the Histidine Modified by DEPC

Figure 5:
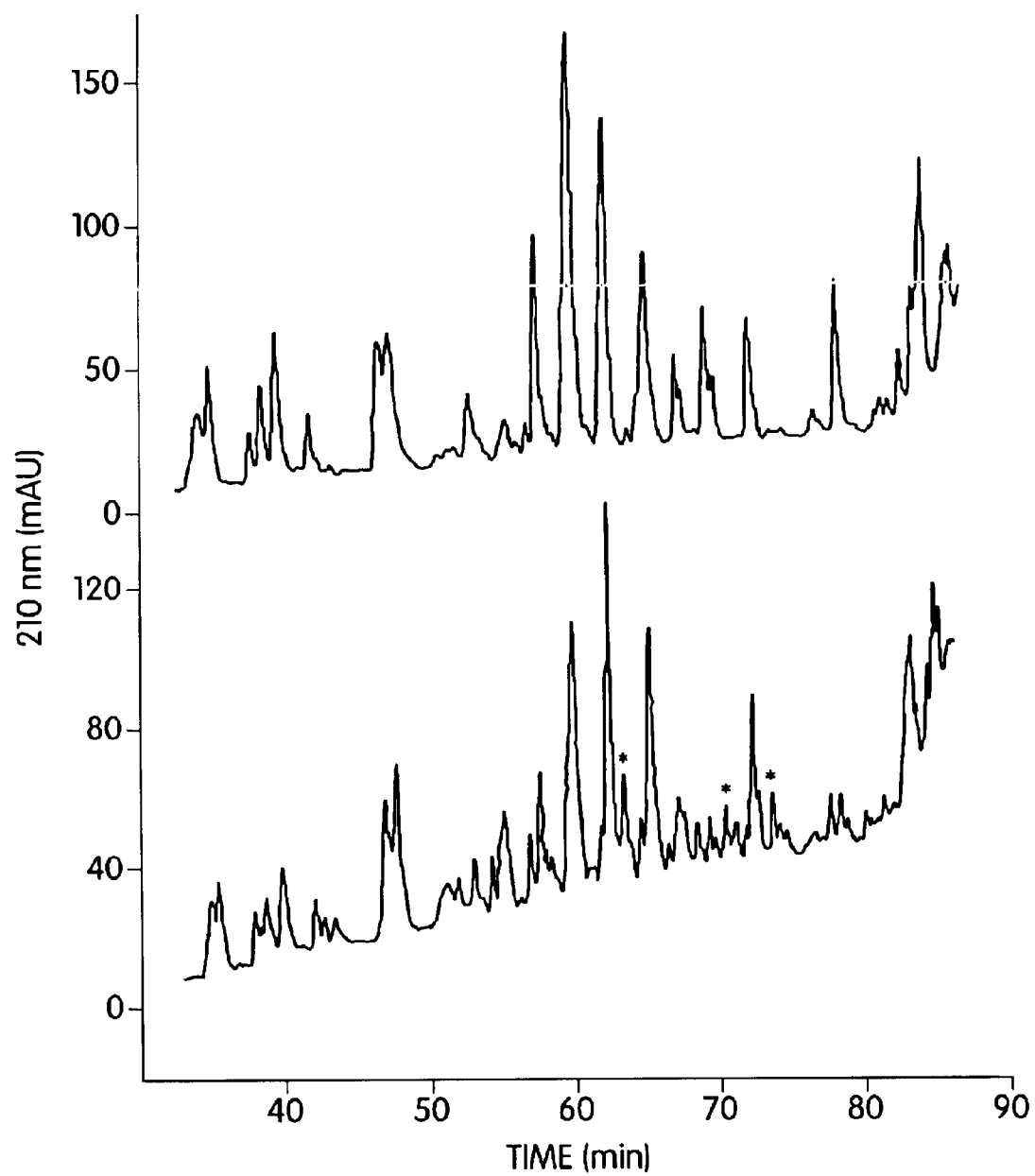
FIG. 5 is a reverse phase HPLC profile of a lys-C digest of heparinase III which was not exposed to DEPC (top panel) and a peptide profile of heparinase III labeled with DEPC (bottom panel).
Figure 6A:
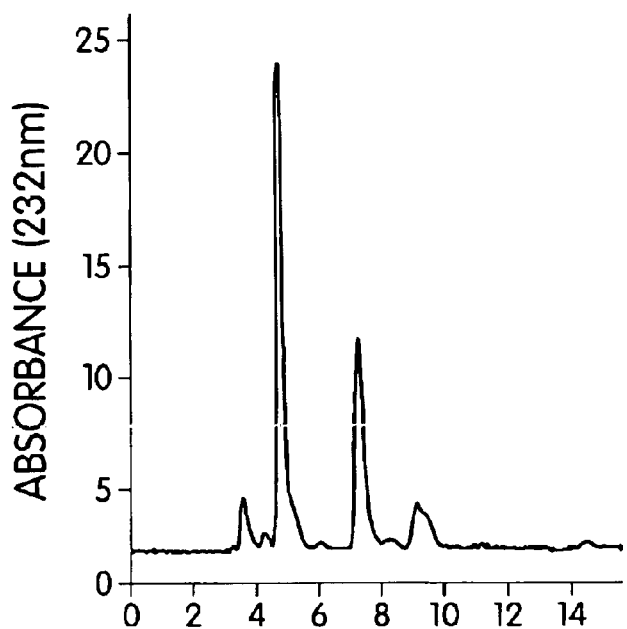
FIG. 6 is a series of graphs depicting SAX analysis of exhaustive heparinase III digests of heparan sulfate. Heparan sulfate was digested with either heparinase III from *F. heparinum* (panel A), recombinant heparinase III (panel B), H295A mutant enzyme (panel C), H510A mutant enzyme (panel D), or the H105A mutant enzyme (panel E).
Figure 6B:
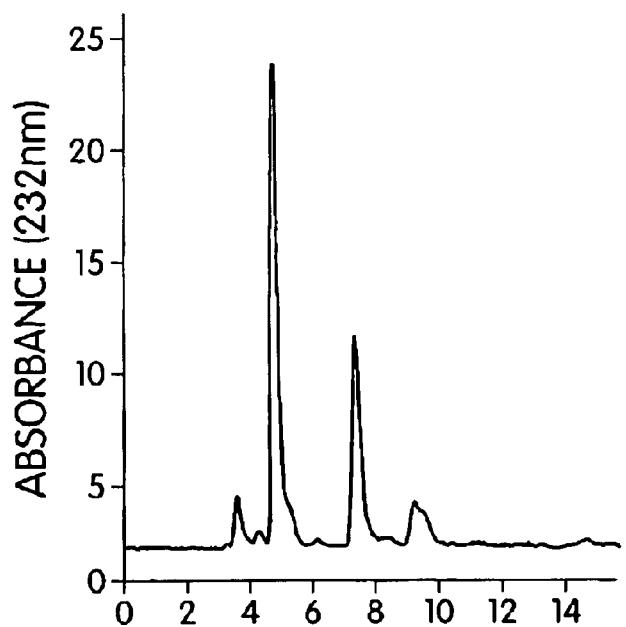
Figure 6C:
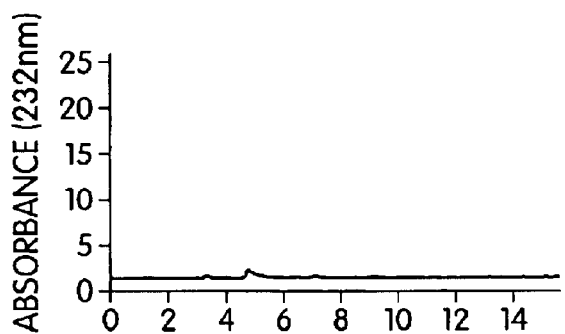
Figure 6D:
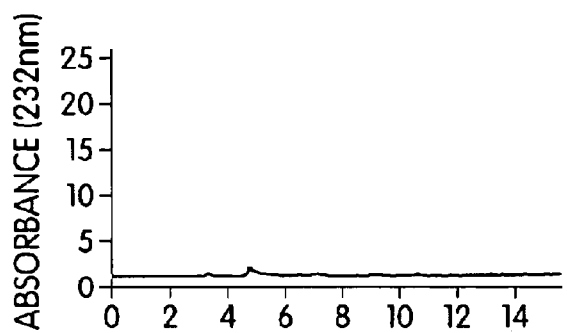
Figure 6E:
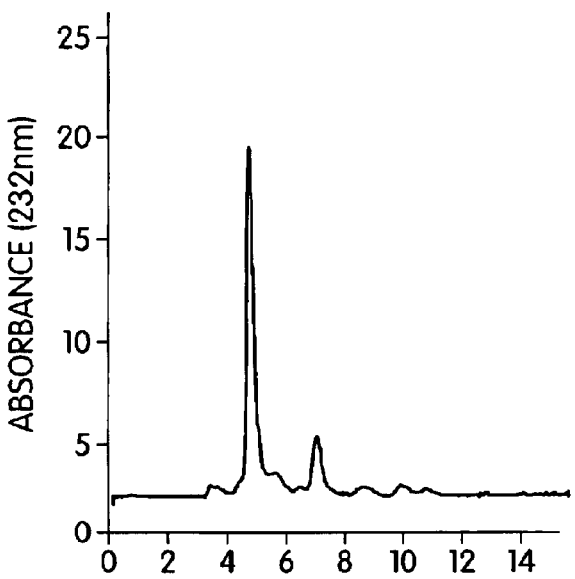

To identify the histidine(s) modified by DEPC that resulted in the loss of enzymatic activity, DEPC-modified heparinase III was digested with Lys-C. Peptides that had altered retention times and an increased in absorbance at 240 nm as compared to a control digest were collected and sequenced (FIG. 5). Three peptides had altered retention times and increased absorbance at 240 nm were isolated and sequenced. Two of the peptides contained histidine 295 and one contained no modified histidine residues.

Labeling of the DEPC-reactive histidines was completed by first reacting heparinase III with DEPC, then denaturing the protein in urea. Following an overnight digest with Lys-C, the resultant peptides were separated by using a 1.6%–78.4% acetonitrile gradient over 120 minutes, which included a 5 min isocratic phase (1.6% acetonitrile, 0.1% trifluoroacetic acid) at the beginning of the run. Lys-C peptides were monitored at 210, 240, and 277 nm. New peptide peaks, not present in the control digest and with a marked absorbance at 277 nm were collected and sequenced. These peptides are marked with an asterisk in the chromatogram. The peptides migrating at 62 and 71 min. contained the sequence QVYADGMQFELSPIYHVAAIDIFLK (SEQ ID NO.:3) including histidine 295. The other consistently labeled peptide did not contain a histidine. FIG. 5A shows C4 RPHLPLC profile of the Lys-C digest of heparinase III which was not exposed to DEPC and FIG. 5B shows the peptide profile of heparinase III labeled with DEPC.

Example 3
Site-Directed Mutagenesis of Heparinase III

In parallel to the mapping studies and to confirm the results of the chemical modification experiments, each of the thirteen histidine residues present in heparinase III was mutated to alanine. The recombinant heparinase III mutant proteins were expressed, purified, and assessed for enzymatic activity towards heparan sulfate (Table 2).

| Enzyme | $K_M$ (uM)[a] | $k_{cat}$ (s$^{-1}$) |
|---|---|---|
| wild-type r-heparinase III | 80 | 78 |
| H36A | 98 | 86 |
| H105A | ND[b] | ND[b] |
| H110A | 9 | 37 |
| H139A | 191 | 68 |
| H152A | 58 | 83 |
| H225A | 80 | 22 |
| H234A | 75 | 23 |
| H241A | 16 | 5 |
| H295A | ND | ND |
| H424A | 59 | 24 |
| H469A | 71 | 100 |
| H510A | ND | ND |
| H539A | 92 | 132 |

[a]Calculated assuming a molecular weight for heparan sulfate of 15 kDa.
[b]Protein expression levels were too low for heparinase III kinetic assay.

As a control, the r-heparinase III construct without its putative signal sequence was expressed. The concentration and purity of all recombinant enzyme preparations were determined using SDS-PAGE. The recombinantly expressed heparinase III was also compared to the heparinase III isolated from *F. heparinum* to ensure that they were the same molecular weight. SAX analysis of exhaustive heparinase III digests of heparan sulfate is shown in FIG. 6. Heparinase III (20 μg/mL) was incubated with a 4 mg/mL of heparan sulfate overnight at 37° C. The reaction was loaded onto a SAX column and the saccharide products were eluted using a gradient of 0.2–1.0 M NaCl, pH 3.5 over 30 min. and monitored at 232 nm. (A) Heparan sulfate digested with heparinase III from *F. heparinum*. (B) Heparan sulfate digested with recombinant heparinase III. (C) Heparan sulfate digested with the H295A mutant enzyme. (D) Heparan sulfate digested with the H510A mutant enzyme. (E) Heparan sulfate digested with the H105A mutant enzyme.

Both enzymes displayed similar kinetic activity towards heparan sulfate and yielded the same degradation profiles as determined by SAX-HPLC (FIG. 6). The products of the exhaustive digests were then analyzed using capillary electrophoresis. The first major peak (5 min) observed in the SAX-HPLC chromatograms has a migration time that is identical to $\Delta U$-$H_{NAc}$. The second peak (7.5 min) has a migration time that is identical to $\Delta U$-$H_{NS}$ (data not shown). Thus, the heparan sulfate degradation by recombinant heparinase III produces an identical product profile to that of wild type heparinase III indicating that, at least functionally, these enzymes are the same.

The replacement of histidine 295 and histidine 510 with alanine residues completely eliminated the activity of heparinase III towards heparan sulfate (Table 2). The H295A and H510A mutant enzyme showed no differences in terms of expression level or molecular weight. However, both the kinetic data and the exhaustive digest profile for H295A and H510A suggest that the enzymes are completely inactive (FIG. 6). Nine of the histidine mutants (H36A, H152A, H225A, H234A, H241A, H469A, H424A, H510A and H539A) showed no significant changes in recombinant protein yield, enzyme activity, or kinetic parameters when compared with r-heparinase III. Interestingly enough, three (H105A, H110A, and H139A) of the thirteen histidine mutants yielded much less recombinant protein than either recombinant heparinase III or the other mutants. Despite lower protein levels, the H110A and H139A mutant proteins were amenable to kinetic analysis whereas the H105A mutant protein was not. However, SAX-HPLC analysis of overnight heparan sulfate digests confirmed that despite lower levels of recombinant expression, all three of these under-expressed enzymes retain their catalytic activity (FIG. 6).

Figure 7:
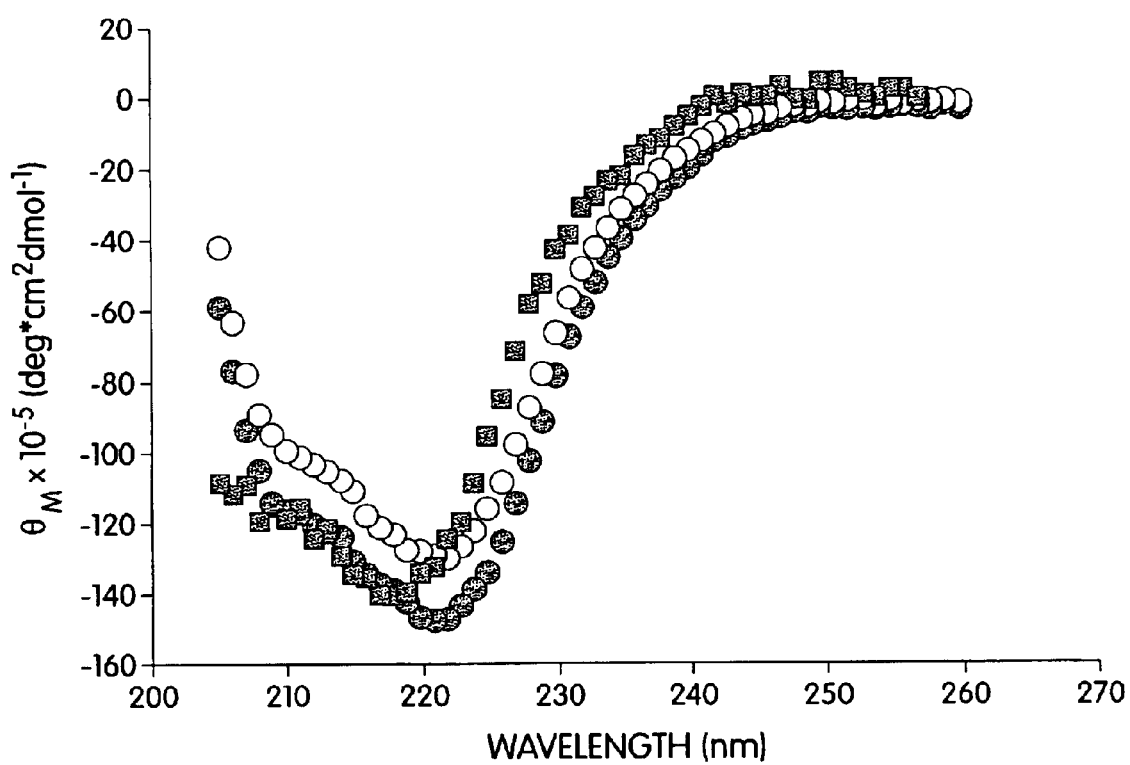
FIG. 7 depicts a circular dichroism analysis of recombinant heparinase III and the H295A mutant enzyme, and the H510A mutant enzyme.

The recombinantly expressed heparinase III, the H295A mutant, and the H510A mutant were compared using circular dichroism (CD). Circular dichroism analysis of recombinant heparinase III and the H295A mutant enzyme is shown in FIG. 7. The recombinant heparinase III (●), the H295A mutant enzyme (○), and the H510A mutant enzyme (■) were concentrated and buffer exchanged into 50 mM sodium phosphate buffer, pH 7.0. Readings were taken using a quartz cell with a 1 mm path length at 25° C. Spectra were recorded between 205 and 260 mn with an average of 10 scans; the bandwidth was 1.0 nm; and the scan rate was 3 m/min. The CD band intensities are expressed as molar ellipticities, $\theta_M$, in degrees·cm$^2$·dmol$^{-1}$.

The possibility remained that the histidine 295 and/or histidine 510 were somehow responsible for the folding or the tertiary structure of the enzyme and not directly involved in catalysis. However, the CD spectrum for H295A and H510A were nearly identical to that of recombinant heparinase III (FIG. 7). While the near identity of the CD profiles does not preclude the possibility that there are perturbations in the local environment surrounding histidine 295 and histidine 510 that are not represented in the CD profile, it does suggest there are no gross conformational changes induced by mutating histidine 295 and histidine 510 to alanine.

Figure 8:
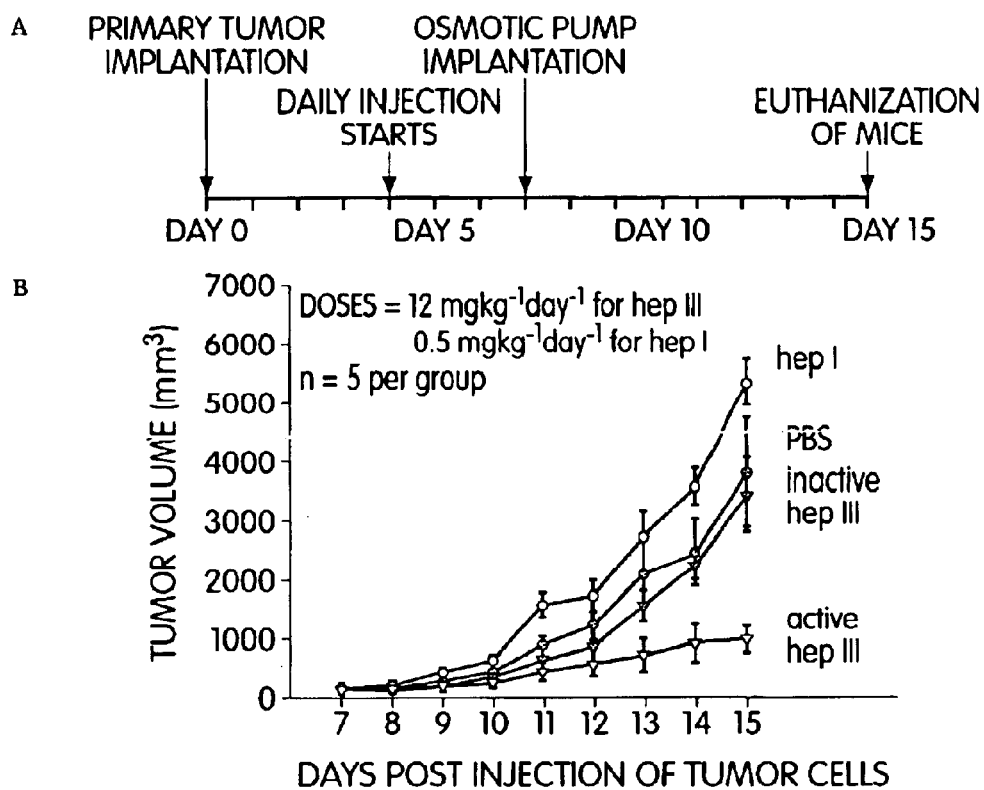
FIG. 8, panel A, depicts the timecourse of the experiment on tumor growth and metastasis in tumor-bearing mice.

Example 4
Comparison of the Heparinase I and III re Tumor Growth and Metastasis Heparinases I and III, which have very distinct substrate specificities for cleaving HLGAGs, were employed as tools to investigate the role of HLGAGs in tumor growth and metastasis. While heparinase I cleaves at the highly sulfated regions of HLGAGs, heparinase III only cleaves at the under-sulfated regions of the polysaccharide chain, thereby rendering these enzymes powerful tools to investigate in vivo and in vitro roles of HLGAGs, in development, morphogenesis, angiogenesis etc. To examine the roles of HLGAGs in tumor growth and metastasis, we used B16BL6 melanoma as a model system and treated tumor-bearing mice with either heparinases I or III to investigate both primary tumor growth as well as tumor metastasis. Consistent with the current paradigm, heparinase I accelerated tumor growth (FIG. 8). At a dosage of 0.5 mg/kg/day of heparinase I, tumor growth was increased by about 39%. However and most surprisingly, heparinase III inhibited primary tumor growth (FIG. 8). The inhibition of melanoma growth by heparinase III was shown to be dose dependent. Inhibition of primary tumor growth by heparinase III was first observed at 2 mg/kg per day. Tumor growth was inhibited by 73% at 12 mg/kg per day, the maximum dosage tested in the study (FIG. 8). Control mice treated with heat inactivated heparinase III exhibited comparable growth curves with that of mice treated with PBS (FIG. 8), suggesting that the catalytic activity of heparinase III was responsible for heparinase III's ability to inhibit primary tumor growth. Histological examination of tumor samples revealed increased apoptosis in heparinase III treated tumors, while heparinase I treated tumors revealed reduced apoptosis.

Mice, 15 days after tumor implantation with B16BL6 melanoma, were examined. $4 \times 10^5$ log growth phase B16BL6 melanoma cells in 0.1 ml PBS were injected to the flank of C57BL/6 mice on day 1. Daily injection of 0.1 ml of PBS, heat inactivated hep III or active heparinase III (2 mg/ml, recombinantly expressed, purified, buffer exchanged with PBS, and concentrated) started at the day 4 and continued throughout the experiment. At day 7, osmotic pumps (100 μl capacity delivering at 0.5 μl per hour) containing PBS or 3 mg/ml hep III were implanted subcutaneously at a place remote from the tumor site. Mice were sacrificed at day 15. Upon visual inspection, the control the mice treated with PBS or inactive Hep III had significantly larger tumor masses than the mice treated with active Hep III.

FIG. 8 depicts the tumor volume of the tumors isolated from the mice described above. Tumor volume was measured daily after day 7 with a caliper and calculated with the formula [volume=$0.52 \times (width)^2 \times (length)$]. The data was depicted as growth curves of mice bearing melanoma treated with PBS, inactive hep III and active hep III.

To ensure that these observations were not limited to the tumor model chosen, hep III was used to treat mice bearing Lewis lung carcinoma (LLC) tumors. Growth curves of primary tumor growth for LLC tumor in C57BL/6 mice treated with either PBS or heparinase III were plotted. $4 \times 10^5$ log phase LLC cells were injected subcutaneously to the flank of mice on day 1. Daily injection of 0.1 ml of either PBS or 2 mg/ml recombinantly expressed heparinase III started at the day 4 and continued throughout the experiment. At day 8, osmotic pumps (100 μl capacity delivering at 0.5 μl per hour) containing PBS or 3 mg/ml hep III were implanted subcutaneously at a place remote from the tumor site. Mice were sacrificed at day 20. Lung metastasis of LLC cells injected through tail vein were quantitated as number of lung nodules. Log growth LLC cells were trypsinized for 30 seconds and resuspended in PBS to a final concentration of $1 \times 10^6$ per ml. For experimental group, cells were incubated with 200 nm hep III for 30 minutes at 37° C. before injecting 0.2 ml of cell suspension via tail vein. Mice were euthanized 12 days after tail vein injections, lungs were harvested, rinsed in tap water and fixed overnight in Bouin's solution. The number of nodules on lung surface was counted with the aid of a dissection microscope.

Similar to the B16BL6, heparinase III treatment of mice-bearing LLC tumor at 12 mg/kg per day showed inhibition in tumor growth. In addition, removal of the HLGAG coat present on the LLC cells upon heparinase III treatment (and the presence of HLGAG fragments) inhibited the LLC cells to colonize in the lungs similar to the B16BL6 experiment. We investigated the ability of HLGAG fragments derived from LLC cells to either support or inhibit B16BL6 tumor growth and metastasis. Both, heparinase I and III generated HLGAG fragments from the LLC cells were isolated, harvested in PBS. Consistent with the B16BL6 results, heparinase I generated LLC HLGAG fragments promoted growth of B16BL6 tumor cells, while heparinase III generated LLC HLGAG fragments showed minimal effect on growth of B16BL6 cells. Similarly, when B16BL6 cells were incubated with the heparinase derived LLC HLGAG fragments prior to injection into mice, heparinase III derived LLC HLGAG fragments inhibited B16BL6 metastasis to the lungs. Thus, the in vivo studies, along with in vitro cell culture experiments points to the enzymatic action of hep III reducing the tumorigenicity of a variety of tumor cell types.

There are two possible mechanisms by which heparinase may be acting on tumor cells. For instance, heparinase III treatment of cells may result in cells losing their unique surface HLGAG coat and this directly or indirectly may impinge on their ability to grow or metastasize. On the other hand heparinase III treatment of cells may also result in the generation of distinct HLGAG fragments, and these fragments could then directly or indirectly modulate tumor cell function. It was thought that heparinase III may function though either one of these mechanisms or through some combination of these mechanisms. To investigate the mechanisms of action further, we treated B16BL6 cells with either heparinases I or III, to remove the HLGAG coat on the tumor cell surface. Interestingly, the removal of the HLGAG coat, either by heparinase I or III, had no effect on the ability of these cells to grow in mice compared to untreated cells. As shown below, we also found that HLGAG fragments were capable of modulating tumor cell function, suggesting that this is the mechanism through which heparinase III exerts its anti-tumor and anti-metastasis functions.

Figure 9:
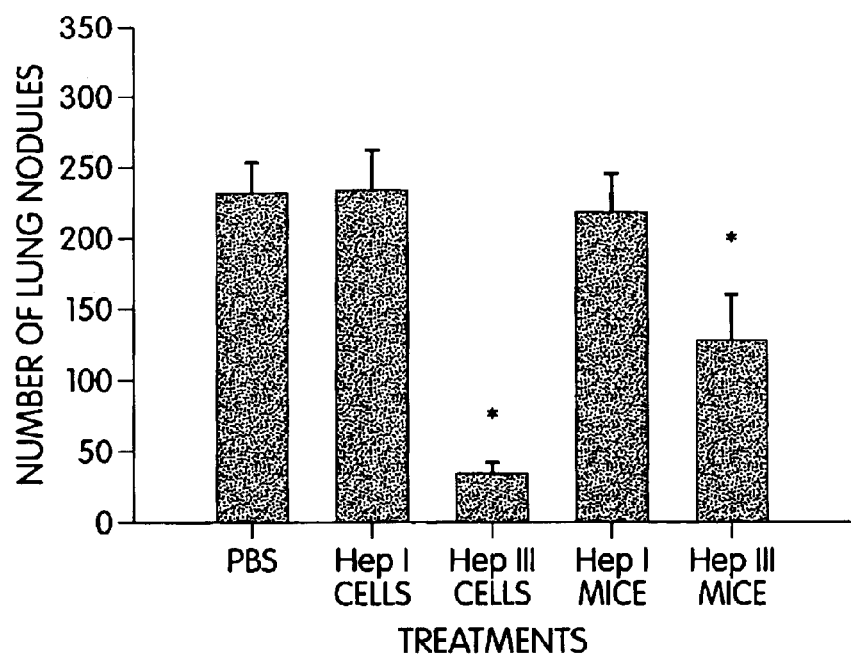
FIG. 9 is a bar graph depicting number of lung nodules that developed 13 days after tail vein injection of B16 BL6 cells. The cells were either treated with PBS, heparinase I, or heparinase III.

We next investigated the ability of heparinase treated B16BL6 melanoma cells to metastasize to the lungs. Lung metastasis of B16BL6 melanoma 13 days after tail vein injection of B16BL6 cells is shown in FIG. 9. B16BL6 cells in log growth phase were briefly trypsinized and resuspended in PBS to a final concentration of $1 \times 10^6$ per ml. Prior to injection, cells were treated with either PBS, hep I (200 mn) or hep III (200 nm) for 30 min. at 37° C. 0.2 ml cell suspensions ($2 \times 10^5$ cells) were injected slowly via tail vein. Mice were sacrificed 13 days later and lungs were harvested, rinsed with tap water. The number of nodules on lung surface were counted with the assistance of a dissection microscope. *indicates $p<0.05$ (Mann-Whitney test).

B16BL6 cells were treated with either heparinases I or III and then injected via tail vein of syngeneic mice. Interestingly, heparinase III treated B16BL6 cells were significantly less able to metastasize to the lungs, while heparinase I treated cells were marginally effected, if any, in their ability to metastasize to the lungs when compared to the control PBS treated cells (FIG. 9). Thus, the removal of specific HLGAG coat present on the B16BL6 tumor cells significantly affected the ability of the tumor cells to metastasize but had no effect on the growth of B16BL6 tumor cells. It should be pointed out that heparinase treatment of cells would generate HLGAG fragments that might still bind to specific proteins on the B16BL6 surface to inhibit tumor metastasis.

Figure 10A:
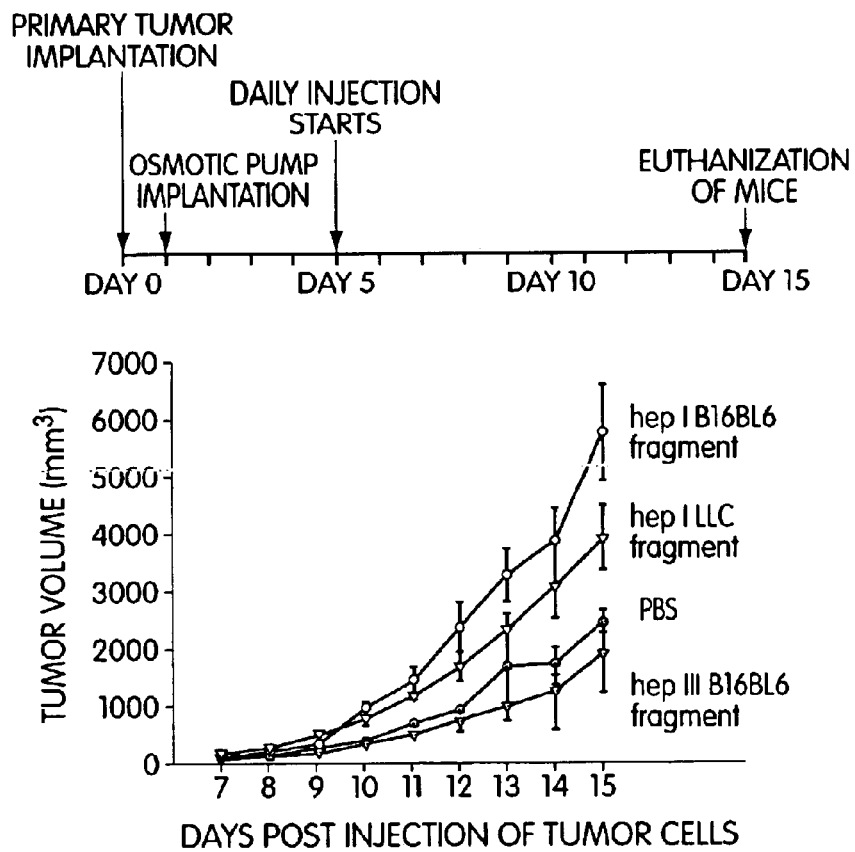
FIG. 10, panel A, depicts the tumor volume of mice that were treated with GAG fragments generated from treatment of B16 BL6 cells with either heparinase I, heparinase III, or PBS or fragments generated from heparinase I treatment of LLC cells. Tumor volume was measured over time between 7 and 15 days post-injection of the tumor cells.
Figure 10B:
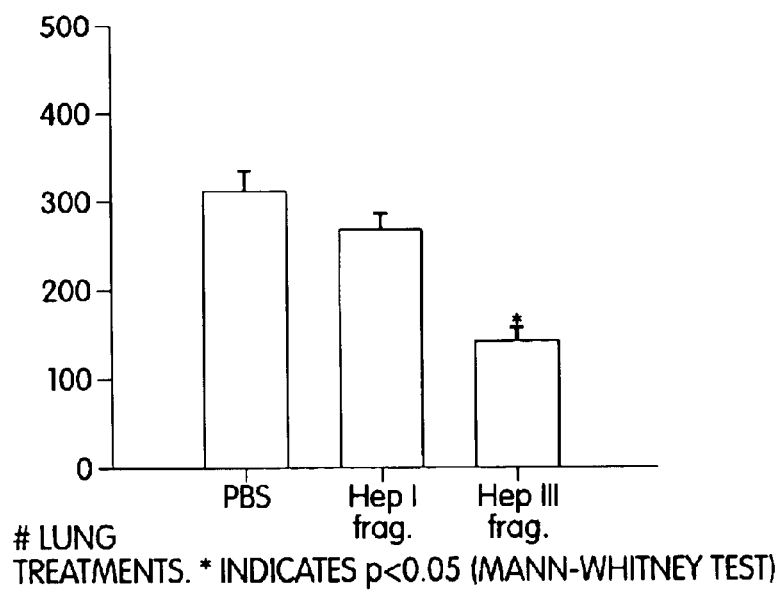

In order to investigate a plausible role in tumor growth and metastasis for the HLGAG fragments generated upon heparinase treatment of the B16BL6 HLGAG coat, both the heparinase I and III generated HLGAG fragments from the B16BL6 cells were isolated, harvested in PBS and tested (FIG. 10). B16BL6 melanoma were treated with GAG fragments generated from treatment of B16BL6 cells with hep I and III. Briefly, 80–90% confluent cells were washed with PBS once. 1.5 ml of PBS containing 200 nm of heparinase I or III were added to the flasks, incubated at 37° C. on a shaker for 2 h. Supernatant was pooled into a tube, centrifuged for 5 minutes at 3000 rpm, boiled for 15 minutes and filtered. The solution was finally incubated with Chondroitinase ABC for 2 h at 37° C., the reaction was stopped by boiling for 1 min. $4 \times 10^5$ B16BL6 cells were injected subcutaneously as described in FIG. 8 on day 1. Osmotic pumps (200 ul capacity delivering 0.5 ul per hour) were implanted subcutaneously on day 2. Daily injection of 0.1 ml GAG fragment solution and PBS was started on day 5 and continued throughout the experiment. The mice were euthanized on day 15. Tumor volume is shown in FIG. 10A. Lung metastasis of B16BL6 melanoma were examined. $2 \times 10^5$ of B16BL6 resuspended in PBS, heparinase I generated fragment and heparinase III generated fragment solutions were injected via tail vein of mice (n=7 or 8). Lungs were harvested 13 days after injection, treated and counted as described earlier. * indicates p<0.05 (Mann-Whitney test). The number of lung nodules was calculated.

Interestingly, heparinase I generated HLGAG fragments significantly promoted primary tumor growth, while heparinase III generated fragments showed did not (FIG. 10). Consistent with the enhanced tumor growth, histological examination of tumor samples revealed reduced apoptosis for heparinase I generated HLGAG fragment treatment. On the other hand and most intriguingly, when B16BL6 cells were suspended in the PBS containing heparinase III generated HLGAG fragments prior to injection via tail vein of mice, these fragments inhibited lung metastasis of B16BL6 cells, while heparinase I generated fragments showed marginal effect, if any. Thus, the HLGAG fragments generated from B16BL6 cells by heparinase treatment also appear to play a role in tumor growth and metastasis.

In further support of this conclusion ex vivo digestion of the HLGAG coat present on tumor cells with either heparinase, followed by centrifugation and resuspension in PBS to remove the enzyme and HLGAG fragments released from the cell surface, prior to in vivo injection results in the cells being functionally identical to controls. Thus the released tumor cell HLGAG fragments appear to play the key role in modulating tumor growth and metastasis.

Immunohistochemistry was done as described (Parangi et al., 1996; O'Reilly et al., 1994) with minor modifications. Briefly, tumor tissues were fixed in either 4% (vol/vol) formaldehyde overnight for von Willebrand factor (vWF) staining and terminal deoxynucleotide transferase (TdT) labeling or in Glyo-Fixx solution overnight for Ki-67 nuclear antigen staining. Tissues were embedded in paraffin according to standard histological procedures. For vWF staining, sections (5 μm thick) were incubated with 0.2 N HCl for 10 min. autoclaved in a Coplin jar immersed with Target retrieval Solution (Dako) for 15 min. and permeabilized with 2 μg/ml proteinase K at 37° C. for 15 min. Sections were incubated with rabbit anti-human vWF antibody coupled with horseradish peroxidase (HRP) (Dako). Positive staining was detected by substrate reaction with diaminobenzidine. Sections were counterstained with Gill's hematoxylin and mounted in Permount (Fisher). Ki-67 antigen staining (rabbit anti-human Ki-67 antigen antibody coupled with HRP, Dako) and TdT labeling (DeadEnd Colorimetric Apoptosis Detection System, Promega) were done essentially according to manufacture's protocol. Capillary density was determined by counting the number of vWF-positive capillaries per high power field (HPF, ×200). The proliferative and apoptotic indices of tumor cells within areas of viable tumor were estimated from the percentage of cells scored under a light microscope at 400-fold magnification. A minimum of 2000 cells were counted in each animal. # indicates standard error.

The overall similarity of data for the B16BL6 and the LLC animal models suggests an important role for HLGAGs in tumor growth and metastasis. The differential effects of heparinases I and III, and the HLGAG fragments generated by heparinases are consistent with the unique specificities of heparinases, and hence the distinct oligosaccharide products they generate. Moreover, HLGAG fragments for one cell type is able to influence effects on another cell type, strongly suggesting the involvement of specific sequences of HLGAG in modulating effects on tumor growth and metastasis.

Figure 11:
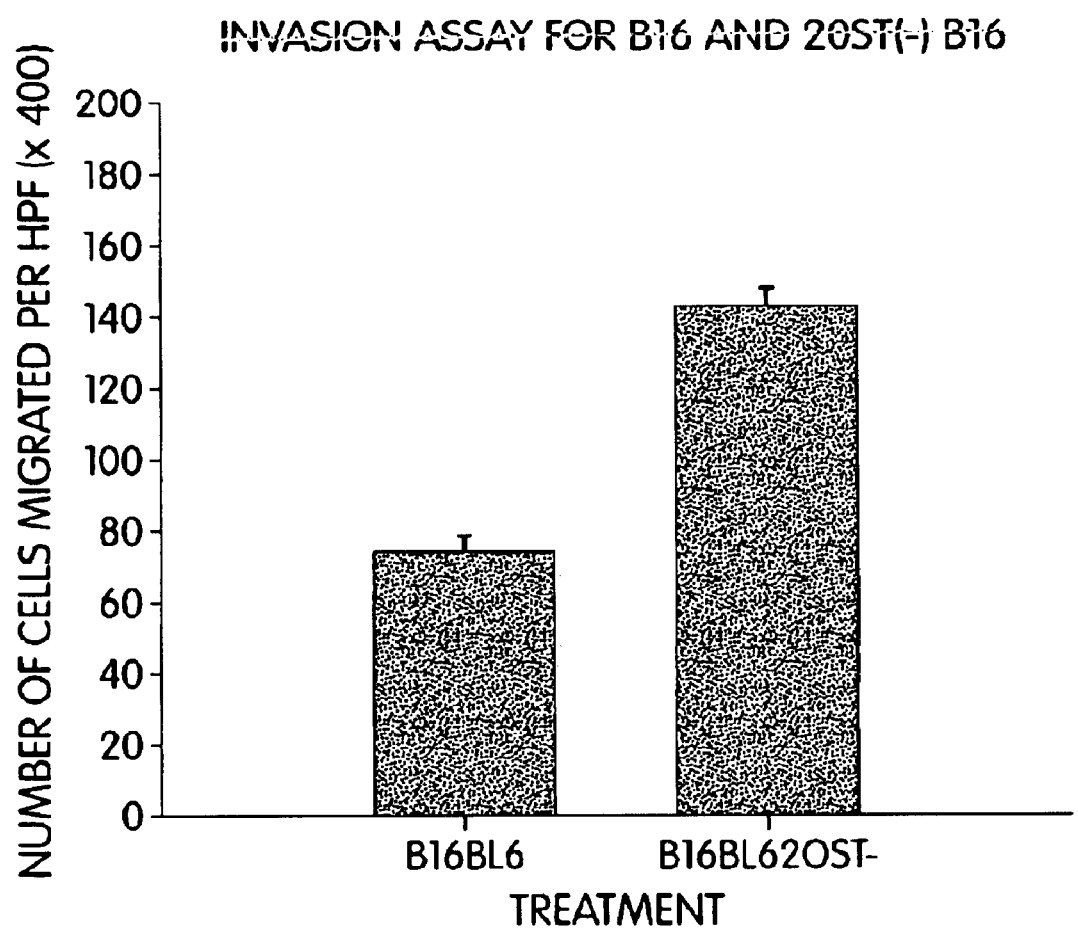
FIG. 11 is a bar graph depicting the effect on B16 cellular migration and invasion of transfection with antisense 2OST in pcDNA3.1.

B16BL6 melanoma cells were transfected with antisense 2OST in pcDNA3.1 and tested in an in vitro invasion assay. The cells that migrated were removed and counted. The number of cells migrated per high power field (×400) for antisense 2OST transfected cells was twice as much as that of untransfected B16BL6 cells. The results are shown in the bar graph of FIG. 11.

Figure 12A:
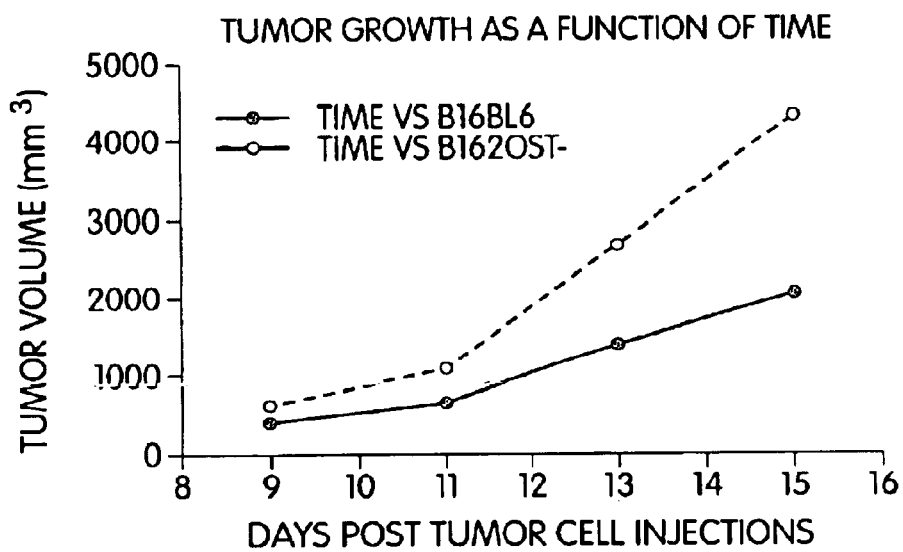
FIG. 12 shows bar graphs depicting the ability of the transfected cells of FIG. 12 to develop into primary tumors as assessed by mean tumor volume (12*a*) and tumor weight (12*b*).
Figure 12B:
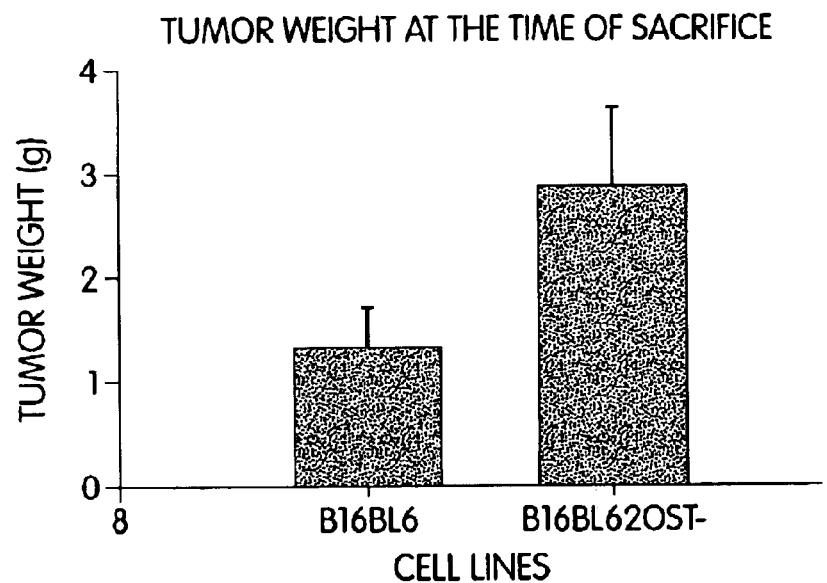

The ability of the transfected cells to develop into primary tumors was assessed by subcutaneous inoculation of $4 \times 10^5$ B16BL6, transfected and untransfected respectively into the flank of nude mice. The mean tumor volume and tumor weight of transfected group was more than two fold greater than that of the untransfected control group, as shown in FIG. 12a and b respectively.

The ability of the transfected cells to metastasize was determined by injection of $2 \times 10^5$ B16BL6 in 0.2 ml PBS, of transfected and untransfected cells via tail vein of C57BL6 mice. The number of metastatic nodules on the lung surface for the transfected group was more than three fold greater than that of the untransfected control. Thus the 2OST antisense transfected B16BL6 appear to be more invasive with higher metastatic potential and growth rate.

Example 5

HLGAG Fragments with Distinct Composition are Potent Inhibitors of Tumor Growth and Metastasis Methods: B16BL6 cells were treated with either a, hep I; b, hep III; or c, a PBS control and the released HLGAG fragments harvested. Saccharide fragments were collected in PBS, and subjected to purification and fractionation. First, samples were bound to an Ultrafree-DEAE membrane, which had been equilibrated with pH 6.0 sodium phosphate, 0.15 M NaCl. They were washed with the same buffer and eluted with 0.1 M sodium phosphate buffer pH 6.0 that contained 1.0 M NaCl. The fragments were then concentrated and buffer exchanged into ultrapure water by application to a microcon column (MWCO=3,000 Da). The sample was digested overnight with a cocktail of hep I–III (1 mU each) in 25 mM sodium acetate 1 mM calcium acetate, pH 7.0. Analysis was completed by capillary electrophoresis using a high sensitivity flow cell under reverse polarity with a running buffer of 50 mM tris/phosphate pH 2.5. Disaccharide identification was made by comigration with known standards, identity of peaks is enumerated in a and b. d, Table showing the relative percentage of the HLGAG disaccharides in hep I and hep III-generated fragments. The percentage was obtained based on the normalized peak areas of the different disaccharides in a and b. Note that the relative composition of the hep I and hep III-generated fragments are very different. The alphanumeric assignment of each disaccharide is also listed as outlined previously (Venkataraman, G., Shriver, Z., Raman, R. & Sasisekharan, R. Sequencing complex polysaccharides. *Science* 286, 537–42 (1999).). Saccharide analysis of the B16BL6 cells that were transfected with the 2OST(−) indicated that there was an absence of 2-O sulfate-containing saccharides, specifically the trisulfated disaccharide $\Delta U_{2S}$-$H_{NS,6S}$. Mass spectrometric oligosaccharide mapping of hep I (e) and hep III (f) derived HLGAG saccharide fragments. Hep I or hep III-derived HLGAG saccharide fragments were subjected to partial enzymatic cleavage by 100 mM (8 μg/ml) heparinase II in 10 mM ethylenediamine, 10 μM ovalbumin, 1 μM dextran sulfate pH 7.0 for one hour.

Resulting digests were complexed with the basic peptide $(RG)_{19}R$ and subjected to matrix-assisted laser desorption ionization mass spectrometry. The HLGAG fragment fingerprint is different for the hep I vs hep III generated fragments consistent with each being structurally distinct.

Figure 13A:
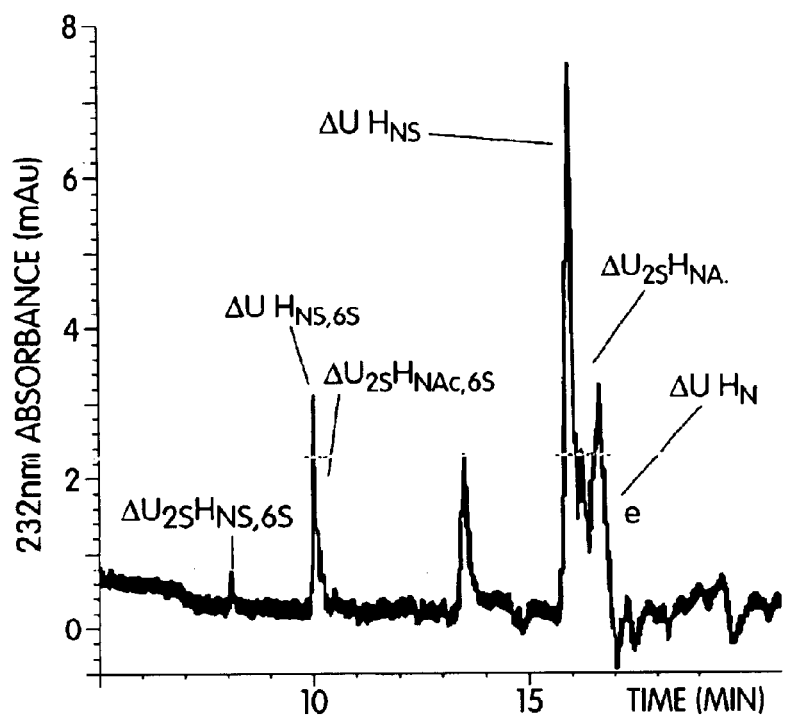
FIG. 13, panel A, depicts the analysis of the heparinase 1-generated fragments.
Figure 13B:
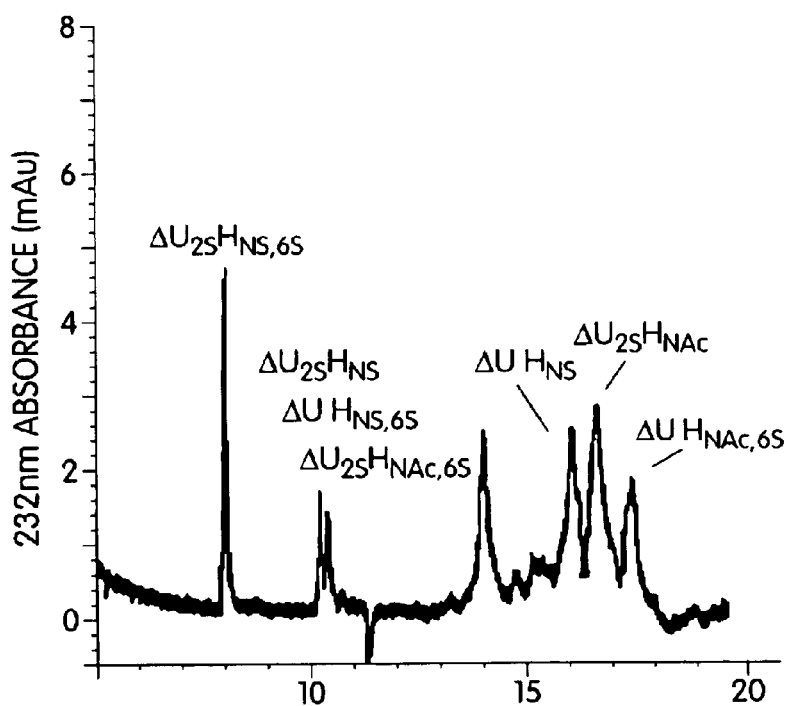
Figures 13C, 13D:
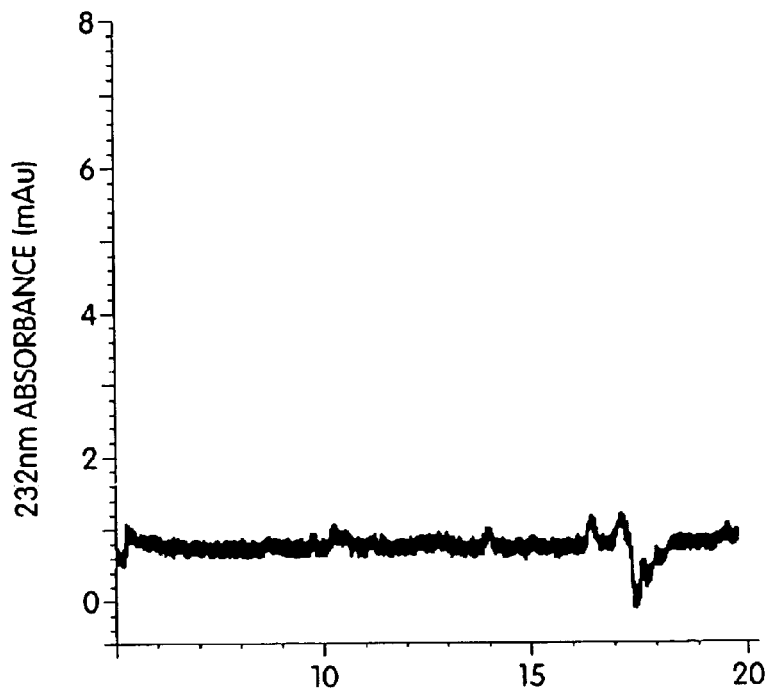
Figure 13E:
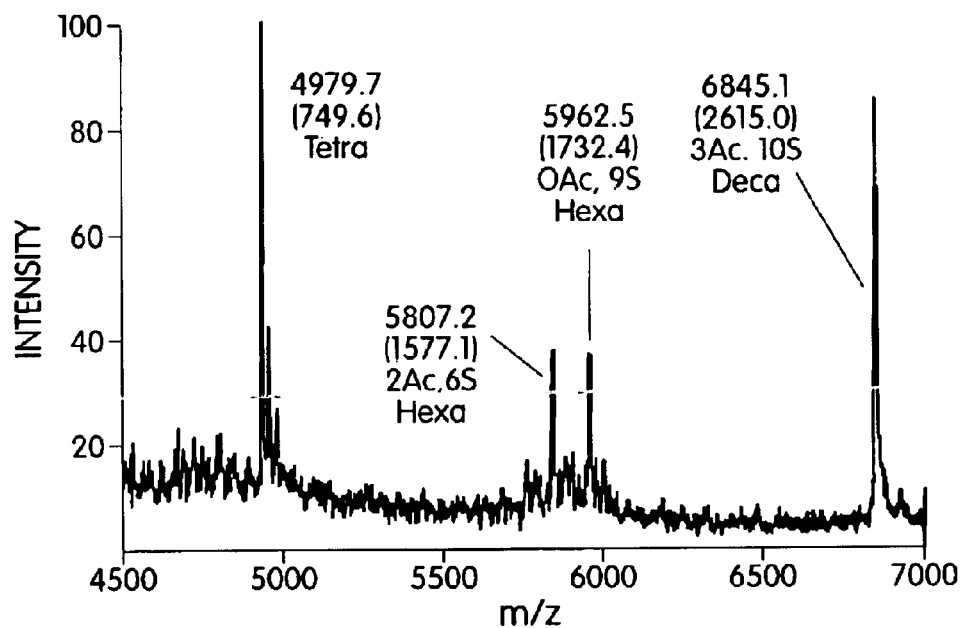
Figure 13F:
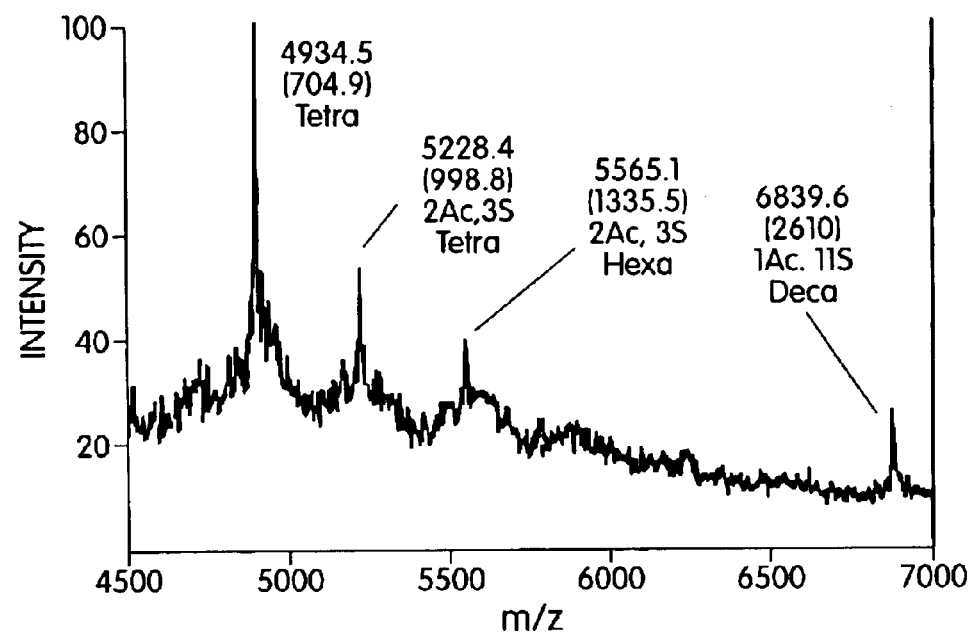

Results: Compositional studies of the HLGAG saccharide fragments generated upon heparinase treatment confirmed that the HLGAG fragments released from B16BL6 cells by hep I or hep III are compositionally different and structurally distinct (FIG. 13a–f). Capillary electrophoresis, in combination with exhaustive enzymatic digest, was used to derive compositional information on the saccharide fragments (FIG. 13). The saccharide fragments derived from hep III treatment had more of tri and di-sulfated disaccharides while the hep I-treated HLGAGs had more mono and un-sulfated disaccharides (FIG. 13a, b). This is consistent with the known substrate specificities of the heparinases. In addition, mass spectrometric investigation of HLGAGs, yielded a "fingerprint" of oligosaccharides generated from each of the treatments and proved that the saccharide fragments generated from the different treatments are structurally distinct (FIG. 13 e, f).

The compositional analysis of the 2-OST antisense construct, demonstrating the deficiency that these mutants have in sulfated HLGAGs specifically 2-O sulfation. Comparison between the composition of the cell surface HLGAGs for this mutant and those for hep I and hep III generated fragments from non-transfected B16BL6 cells indicates that the HLGAGs of the mutant are chemically closer in comparison to hep I generated fragments than of hep III generated fragments.

Example 6
Mechanism of Action: HLGAGs Impinge on the Biological Activity of Specific Signaling Molecules Having observed the marked and opposite effects that distinct HLGAG fragments have on both the tumor and vascular compartments, we sought to elucidate the underlying molecular mechanism of HLGAGs in tumor progression. As many HLGAG binding proteins are growth factors and cytokines, we therefore systematically explored HLGAG-binding growth factors that play key roles in tumor pathobiology to identify an immediate target of the HLGAG fragments generated from the surface of tumor cells. FGF2 signaling has been shown to be a prerequisite for melanoma progression promoting tumor growth in an autocrine fashion, and the interruption of the FGF2 autocrine loop by interfering with either FGF2 or FGF receptor (FGFR) activity results in inhibition of melanoma progression (Rodeck, U. et al. Constitutive expression of multiple growth factor genes by melanoma cells but not normal melanocytes. *J Invest Dermatol* 97, 20–6 (1991). Becker, D., Meier, C. B. & Herlyn, M. Proliferation of human malignant melanomas is inhibited by antisense oligodeoxynucleotides targeted against basic fibroblast growth factor. *Embo J* 8, 3685–91 (1989). Becker, D., Lee, P. L., Rodeck, U. & Herlyn, M. Inhibition of the fibroblast growth factor receptor 1 (FGFR-1) gene in human melanocytes and malignant melanomas leads to inhibition of proliferation and signs indicative of differentiation. *Oncogene* 7, 2303–13 (1992). Torcia, M. et al. Interferon-alpha-induced inhibition of B16 melanoma cell proliferation: interference with the bFGF autocrine growth circuit. *Biochem Biophys Res Commun* 262, 838–44 (1999).). On the other hand, upregulation of the expression of FGF2 in normal melanocytes result in their malignant transformation (Nesbit, M. et al. Basic fibroblast growth factor induces a transformed phenotype in normal human melanocytes. *Oncogene* 18, 6469–76 (1999).). Furthermore, FGF2 is a potent and essential angiogenic factor regulating melanoma neovascularization (Wang, Y. & Becker, D. Antisense targeting of basic fibroblast growth factor and fibroblast growth factor receptor-1 in human melanomas blocks intratumoral angiogenesis and tumor growth. *Nat Med* 3, 887–93 (1997). Birck, A., Kirkin, A. F., Zeuthen, J. & Hou-Jensen, K. Expression of basic fibroblast growth factor and vascular endothelial growth factor in primary and metastatic melanoma from the same patients. *Melanoma Res* 9, 375–81 (1999).) Most importantly, specific HLGAG structures are known to bind and modulate FGF2 activity, and there is increasing evidence that, HLGAG sequences, depending on their structure, can either promote or inhibit FGF2 activity (Guimond, S. E. & Turnbull, J. E. Fibroblast growth factor receptor signaling is dictated by specific heparan sulphate saccharides. *Curr Biol* 9, 1343–6 (1999).). Given the multiple lines of evidence implicating FGF2 as a key switch in melanoma progression, taken together with FGF's strict dependence on HLGAGs for its activity, we sought to determine whether the immediate target of tumor-derived HLGAG fragments is indeed FGF2.

To test whether hep I and hep III-derived fragments bind to FGF2 and affect its activity, we first established that hep III treatment inhibit FGF-induced proliferation of B16BL6 cells in vitro, and additionally and directly confirmed this by examining FGF-mediated downstream signaling pathways, viz., the MAP kinase pathway (ie., Erk-1, 2), the principle signal transduction pathway of FGF2 leading to cell proliferation and differentiation (Seger, R. & Krebs, E. G. The MAPK signaling cascade. *Faseb J* 9, 726–35 (1995).).

a. Methods: B16BL6 cells in 10 cm culture dishes were serum starved for 48 hours before stimulation with 50 ng/ml FGF2. Cells were stimulated for 20 minutes before whole cell lysates were prepared with 1 ml modified RIPA buffer containing various enz me inhibitors (50 mM Tris-HCl, pH 7.4, 1% NP-40, 0.25% Na-deoxycholate, 150 mM NaCl, 1 EDTA, 1 mM EDTA, 1 mM PMSF, 1 μg/ml aprotinin, leupeptin, and pepstatin, 1 mM activated $Na_3VO_4$, 1 mM NaF). Protein concentration in the lysate was determined using the Bio-Rad protein assay kit (BioRad) and adjusted accordingly for electrophoresis analysis. For the heparinase treated groups, cells were treated with either hep I or hep III (200 nM) for 30 mm at 37° C. prior to addition of FGF2. The immunoblot was probed with anti-Erk-1, 2 or anti-phospho-Erk-1, 2 antibody (New England Biolabs; MA) and detected by anti-rabbit IgG conjugated to HRP using SuperSignal West Pico Chemiluminescent substrate (Pierce, Ill).

b. FGF-mediated proliferation of BaF3 cells with transfected FGFR in the presence of HLGAG fragments generated with either hep I or III BaF3 cells expressing FGFR were grown in the following fashion. The initial cell number was counted by Coulter counter, and resuspended to a density of $1 \times 10^5$ cells/ml into 12 samples of 6 ml. Each sample of cells was centrifuged 3 min at room temperature at 1085×g, and resuspended in HLGAG preparations in PBS, producing two sets of cells in the same media. One of each set was supplemented with 50 ng/ml FGF2 (▥) while the other was unsupplemented (▣). 1 ml from each set was added to each of 3 wells on a 24-well tissue culture plate. The cells were incubated for 72 hr at 37° C./5% $CO_2$. Whole cell number was counted at the experimental endpoint by Coulter counter. This procedure was repeated three times. Collected data was normalized using a proliferative index (PI), as previously described (Padera, R., Venkataraman, G., Berry, D., Godavarti, R. & Sasisekharan, R. FGF-2/ fibroblast growth factor receptor/heparin-like glycosaminoglycan interactions: a compensation model for FGF-2 signaling. *Faseb J* 13, 1677–87 (1999).). The index is defined as the increase in cell number for the experimental case divided by the increase in cell number for the positive control. The positive control was cells in DMEM with 10% BCS, 2 mM L-glutamine, 100 U/ml penicillin, 100 µg/ml streptomycin, 500 ng/ml heparin, and 50 ng/ml FGF2. The negative control was cells in DMEM with 10% BCS, 2 mM L-glutamine, 100 U/ml penicillin, 100 µg/ml streptomycin, and 500 ng/ml heparin.

c, Effect of treatment of tumor with hep I and hep III in FGFR1 activation compared to PBS. Level of phosphorylated FGFR1 in tumor samples was assessed by standard immunoprecipitation followed by Westernblotting with phosphotyrosine specific antibody. Primary B16BL6 tumors were grown and treated as described earlier and at day 15 the tumor was harvested in cold modified RIPA buffer containing enzyme inhibitors and homogenized. The homogenates were past through 25-gauge needle 3 times and centrifuged. The supernatant was adjusted for protein concentration using the Bio-Rad protein assay kit (Bio-Rad). FGFR1 was immunoprecipitated with poly-clonal anti-FGFR1 antibody (Santa Cruz Biotechnology, Inc., CA.). Samples were then pelleted, washed, and eluted from the beads by addition of sample buffer and boiled for 3 minutes (Kapila, Y. L., Wang, S. & Johnson, P. W. Mutations in the heparin binding domain of fibronectin in cooperation with the V region induce decreases in pp125(FAK) levels plus proteoglycan-mediated apoptosis via caspases. *J Biol Chem* 274, 30906–13 (1999).). After electrophoresis, the gel was transferred to nitrocellulose membrane by standard methods. The immunoblot was probed with phosphotyrosine specific antibody conjugated to HRP (RC20; Transduction Laboratories, Lexington, Ky.) and developed with SuperSignal West Pico Chemiluminescent substrate. The molecular weight of FGFR1 is 120 KDa.

d, Effect of heparinase treatment on activation of FAK in B16BL6 tumor. The FAK protein was immunoprecipitated with mouse anti-FAK monoclonal antibody (Transduction Laboratories, Lexington, Ky.) according to the procedures described above. The phosphorylated FAK was detected using phosphotyrosine specific antibody RC20.

e, Level of total and phosphorylated Erk-1, 2 in heparinase-treated B16BL6 tumor. Tumor homogenates were prepared and processed as described in c. The supernatant was used for total protein concentration assay and immunoblotting. The immunoblot was detected as described in a.

f, Effect of heparinase treatment on Akt activation. The primary tumor was treated and processed as described above. Akt antibody and phospho-Akt antibody from New England Biolabs were used to probe the immunoblot.

Figure 14:
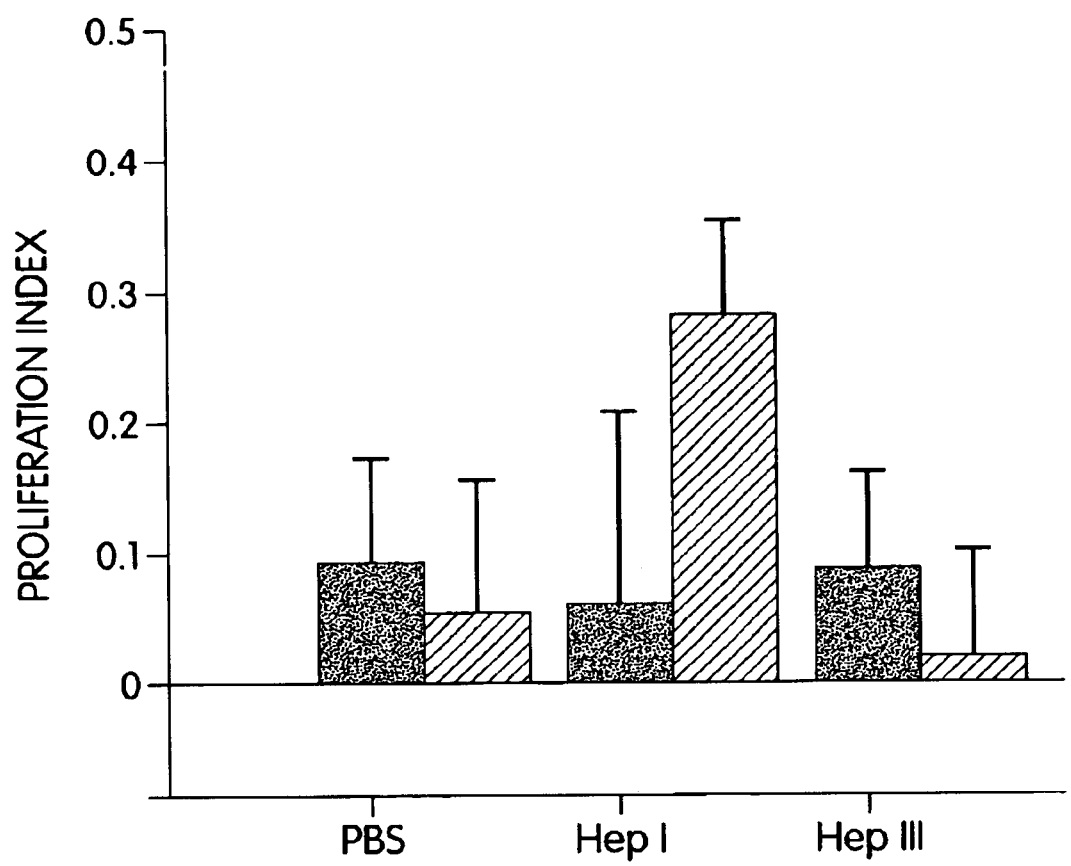
FIG. 14 is a bar graph depicting FGF2 signaling modulated by HLGAG fragments

Results: Upon FGF2 stimulation, decreased Erk-1, 2 activation was seen in hep III treated cells while increased Erk-1, 2 activation was seen with cells treated with hep I. The in vitro data was further confirmed using F32 cells, a pre-lymphocyte cell line that has been transfected with FGFR, and that often has been used as a model system to study FGF-mediated signaling in cell culture unfettered by complications associated with signaling events initiated by other growth factors and/or receptors (Ornitz, D. M. et al. Receptor specificity of the fibroblast growth factor family. *J Biol Chem* 271, 15292–7 (1996).). Similar to what was observed in B16BL6 cells, hep I fragments promote, whereas hep III fragments inhibited FGF2-mediated cellular proliferation in these cells (FIG. 14). Together, the in vitro findings point to the fact that HLGAG fragments derived from the cell surface can substantially and specifically affect FGF2 signaling.

Consistent with the in vitro observations, we find that hep I and hep III-derived B16BL6 fragments significantly affect FGF signaling pathways in vivo. Within the tumor in the animals, we examined both FGFR phosphorylation in hep I and hep III-treated animals as well as Erk-1 and 2 signaling. Treatment of the primary tumor with hep III (or its generated fragments) inhibited phosphorylation of FGFR1 while hep I treatment had the opposite effect on the phosphorylation of FGFR1. Consistently, treatment of the primary tumor with hep III resulted in a lower level of activated Erk-1, 2. Additional intracellular signaling events such as focal adhesion kinase (FAK) activity, which is implicated in cell adhesion and migration processes (Rodriguez-Fernandez, J. L. Why do so many stimuli induce tyrosine phosphorylation of FAK? *Bioessays* 21, 1069–75 (1999). Schlaepfer, D. D., Hauck, C. R. & Sieg, D. J. Signaling through focal adhesion kinase. *Prog Biophys Mol Biol* 71, 435–78 (1999).), was similarly modulated by hep I and III treatment of the tumor. Consistent with these findings, hep III treatment inhibited FAK activation. Notably there was no change in activation of Akt with either hep I or hep III treatment, indicating that the changes in phosphorylation were specific and resulted from down-regulation of only certain signaling pathways. Together, these results suggest that HLGAG fragments mediate FGF2 signaling with hep I-derived fragments promoting FGF2 activity and hep III-generated fragments inhibiting it. This effect was observed in key steps of FGF-mediated signaling, from the cell surface receptor (FGFR) through downstream signaling events.

Example 7

Modulation of FGF2 Activity in vivo by B16BL6Fragments

Methods: Assessment of FGF2 signaling in vivo with the rat corneal pocket assay. Representative slit lamp photographs of rat corneas on day 6 after implantation with Hydron pellets containing FGF2, hep I fragments with FGF2, and hep III fragments with FGF2. The amount of FGF2 loaded into each pellet was ~120 ng, and the amount of HLGAG fragments was approximately 1 ng. The pellets were prepared and implanted essentially as described (Kenyon, B. M. et al. A model of angiogenesis in the mouse cornea. Invest Ophthalmol Vis Sci 37, 1625–32 (1996)). On day 6 after the implantation into the cornea of Sprague-Dawley rats (n=5), the corneal neovascularization was photographed with a slit lamp and the extent of neovascularization was expressed as linear length and circumferential clock hours as described (Kenyon, B. M. et al. A model of angiogenesis in the mouse cornea. Invest Ophthalmol Vis Sci 37, 1625–32 (1996)). Results are summarized in the table. Control pellets co taming no FGF2 failed to induce neovascularization. It was noted that the inhibition of neovascularization by hep III derived fragments are dose dependent, with initial inhibition observed at about 0.02 ng/pellet. In addition, the inhibition of neovascularization by hep III derived fragment was found to be independent of the site of implantation, with similar inhibition observed when hep III derived fragments was implanted as a second pellet in between the FGF2 only pellet d the limbus. Indicates mean and SE.

Model of the formation of cryptic HLGAG modulators of FGF2 signaling. Interaction of HLGAGs (as part of proteoglycans) with the heparin-binding domains of FGF2 and FGFR allows the formation of a ternary complex at the cell surface that forms e basis of FGF2 signaling. Digestion of the cell HLGAG coat with hep I releases fragments with an appropriate spatial display of 2 O-, 6 O- and N-sulfated groups that would allow an optical "fit" to both FGF2 and FGFR, leading to signaling through tyrosine kinase activation. Conversely, hep III-generated HLGAG fragments display another pattern of sulfated groups are still able to bind FGF2 but fail to form a constructive signaling complex at the cell surface, thus inhibiting FGF2 activity.

Figures 15A, 15B:
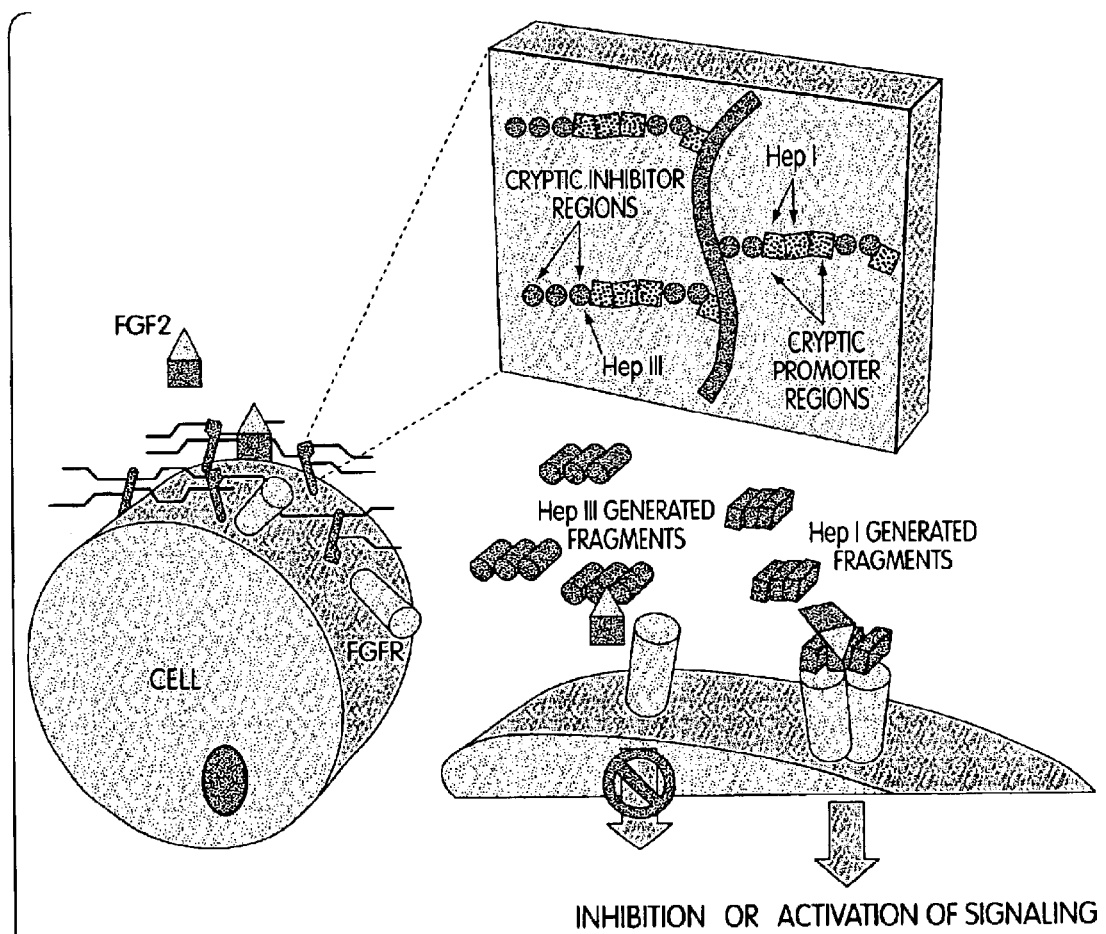
FIG. 15 is a table (15*a*) and a schematic depicting the modulation of FGF2 activity in vivo by B16BL6 fragments (15*b*).

Results: To demonstrate a direct interaction between B16BL6 HLGAG fragments and their immediate target FGF2 in vivo, we evaluated the ability of B16BL6 HLGAG fragments to modulate FGF2-induced responses leading to cell migration, proliferation, and differentiation in vivo using corneal neovascularization assay (FIG. 15a table). In this model, hep I-generated fragments mixed with FGF2 bound to the growth factor and promoted the in vivo neovascularization response to FGF2 (FIG. 15a table) whereas hep III-generated fragments, mixed with FGF2, bound to the growth factor but dramatically inhibited its activity (FIG. 15a table). This result is consistent with the changes in neovascularization observed in the immunohistological study of tumor. Taken together, the above results indicate that a direct in vivo target of the HLGAG fragments released by heparinase treatment is FGF2. Thus, it can be concluded that hep I-generated fragments act to bridge FGF2 to its cognate receptor activating intracellular signaling pathways, while hep III-derived fragments are antagonists, preventing the formation of a signaling complex at the cell surface. Thus, by either directly activating or inhibiting FGF2 signaling, these bioactive fragments are potent modulators of tumor growth and metastasis. The results presented here do not preclude a direct or indirect effect of HLGAG fragments on other HLGAG binding growth factors playing a role in tumor pathophysiology. However, based on the many lines of evidence presented here, it appears that FGF2 is indeed an immediate target for enzymatically derived HLGAG fragments.

The results presented herein demonstrate that by impinging on the biological activity of specific signaling molecules, HLGAGs play a direct role in tumor growth and metastasis. Most importantly, HLGAGs at the cell surface of tumor cells contain both 'activatory' and 'inhibitory' HLGAG sequences that are in balance (FIG. 15b). The specific degradation of one set of sequences (eg., by hep I) results in the release of fragments that promote the biological activity of HLGAG-binding signaling molecules, and thus act as a switch for tumor growth and metastasis. Conversely, degradation by an enzyme with an orthogonal substrate specificity (eg., hep III) tips the balance in the opposite direction, releasing fragments that antagonize HLGAG-binding signaling molecules, leading to the inhibition of tumor growth and metastasis. Thus, we have demonstrated here for the first time that chemically complex HLGAGs at the cell surface are "cryptic" promoters or inhibitors of tumor growth and metastasis that become biologically active upon their release from the cell surface by specific HLGAG degrading enzymes.

Just as collagenases clip the proteinaceous compartment of the ECM, serving either to increase tumor growth (eg., breakdown of the basement membrane) or to inhibit tumors (eg., the formation of endostatin from collagen XVIII), the polysaccharide compartment exhibits a similar phenomenon. Importantly, like the proteolytically cleaved collagen fragment endostatin, distinct HLGAG oligosaccharides upon release by enzymatic cleavage from the tumor cell surface can serve as potent inhibitors of tumor progression. Thus, the present study not only allows a new paradigm of how the polysaccharides modulate tumor growth and metastasis, but it identifies a novel therapeutic target by providing a framework towards the development of HLGAG-based novel anti-cancer molecules.

The data presented herein demonstrate important findings relating to the possible mechanisms and physiological implications of how HLGAGs regulate tumor growth and metastasis. HLGAG fragments may exert their effects through many pathways including autocrine growth and angiogenic factors, or through interactions with ECM molecules. Additionally, the sources of the endogenous HLGAG-degrading enzymes and it substrate specificity also become important. Production of HLGAG-degrading enzyme, presumably by the tumor cells, with substrate specificity similar to heparinase I will be advantageous to tumor cells. Secretion of HLGAG-degrading enzyme by a tumor cell would lead to the production of specific HLGAG sequences (from it own coat or the tumor bed ECM) which might exert effects via autocrine and angiogenic growth factors, or through other signaling pathways to support tumor growth and metastasis. On the other hand production of an HLGAG-degrading enzyme with substrate specificity similar to heparinase III would be extremely beneficial to the host. For instance, the endothelial cells in the vicinity of a tumor or macrophages can secrete an enzyme with substrate specificity of heparinase III leading to the production of specific HLGAG sequences that inhibit tumor growth and metastasis. Consistent with such a model priming the animal with heparinase III does significantly inhibit tumor growth, suggesting a tumor-suppressor property of heparinase III. A balance in the regulation of the bioavailibility of unique HLGAG sequences through HLGAG-degrading enzymes or through other mechanisms may play a key switch to either support or inhibit tumor growth and metastasis.

As described above, hep III treatment caused a significant inhibition in primary tumor growth both in nude mice and C57BL/6 mice with subcutaneous injections of hep III. These results indicate that the response to hep III treatment is not dependent on route of administration nor is it immune mediated.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

What is claimed is:

1. A substantially pure heparinase III, comprising:
a polypeptide having the amino acid sequence of the mature peptide of SEQ ID NO: 2, wherein at least one histidine residue selected from the group consisting of His 36, His105, His110, His139, His152, His225, His234, His241, His424, His469, and His539 has been substituted with a residue selected from the group consisting of alanine, serine, tyrosine, threonine, and lysine.

2. A substantially pure heparinase III comprising:
a modified heparinase III having a modified product profile, wherein the modified product profile of the modified heparinase III is at least 10% different than a native product profile of a native heparinase III, wherein the substantially pure heparinase III has the amino acid sequence of the mature peptide of SEQ ID NO: 2 where at least one histidine residue selected from the group consisting of His 36, His105, His110, His139, His152, His225, His234, His241, His424, His469, and His539 has been substituted with a residue selected from the group consisting of alanine, serine, tyrosine, threonine, and lysine.

3. A substantially pure heparinase III comprising:
a modified heparinase III that can cleave a heparan sulfate substrate having modified heparinase III $k_{cat}$ value, wherein the modified heparinase III $k_{cat}$ value is at leas 10% different than a native heparinase III $k_{cat}$ value, wherein the substantially pure heparinase III has the amino acid sequence of the mature peptide of SEQ ID NO: 2 where at least one histidine residue selected from the group consisting of His 36, His105, His110, His139, His152, His225, His234, His241, His424, His469, and His539 has been substituted with a residue selected from the group consisting o alanine, serine, tyrosine, threonine, and lysine.

4. A pharmaceutical preparation comprising a sterile formulation of the substantially pure heparinase III of claim 1 and a pharmaceutically acceptable carrier.

5. An immobilized substantially pure modified heparinase III comprising:
   a modified heparinase III as in claim 1, and
   a solid support, wherein the modified heparinase III is immobilized on the solid support.

6. The substantially pure heparinase III of claim 1, wherein the polypeptide has at least one substitution within a histidine residue selected from the group consisting of His 110, His225, and His241.

7. The substantially pure heparinase III of claim 1, wherein the polypeptide has a substitution at His110.

8. The substantially pure heparinase III of claim 1, wherein the polypeptide has a substitution at His241.

9. The substantially pure heparinase III of claim 1, wherein the polypeptide has a substitution at His225.

10. The substantially pure heparinase III of claim 9, wherein the His225 is substituted with alanine.

* * * * *

UNITED STATES PATENT AND TRADEMARK OFFICE
CERTIFICATE OF CORRECTION

PATENT NO. : 6,869,789 B2
DATED : March 22, 2005
INVENTOR(S) : Liu et al.

It is certified that error appears in the above-identified patent and that said Letters Patent is hereby corrected as shown below:

Column 54,
Line 60, please replace "leas" with -- least --.

Column 55,
Line 1, please replace "o" with -- of --.

Signed and Sealed this

Seventh Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,869,789 B2
APPLICATION NO. : 09/802285
DATED : March 22, 2005
INVENTOR(S) : Dongfang Liu et al.

It is certified that error appears in the above-identified patent and that said Letters Patent is hereby corrected as shown below:

At column 1, lines 10-12, please delete

"Some aspects of the invention were made with government support under NIH Contract No. GM57073. The government may have certain rights in the invention."

and insert

-- This invention was made with government support under Grant No. R01 GM57073, awarded by the National Institutes of Health. The government has certain rights in this invention. --

Signed and Sealed this
Twenty-sixth Day of April, 2011

David J. Kappos
*Director of the United States Patent and Trademark Office*

SEQUENCE LISTING

<160> NUMBER OF SEQ ID NOS: 3

<210> SEQ ID NO 1
<211> LENGTH: 1980
<212> TYPE: DNA
<213> ORGANISM: Pedobacter heparinus -continued

```
<400> SEQUENCE: 1
atgactacga aaattttaa aaggatcatt gtatttgctg taattgccct atcgtcggga        60
aatatacttg cacaaagctc ttccattacc aggaaagatt ttgaccacat caaccttgag      120
tattccggac tggaaaaggt taataaagca gttgctgccg caactatga cgatgcggcc      180 aaagcattac tggcatacta cagggaaaaa gtaaggcca gggaacctga tttcagtaat      240
gcagaaaagc ctgccgatat acgccagccc atagataagg ttacgcgtga atggccgac      300 aaggctttgg tccaccagtt tcaaccgcac aaaggctacg ctattttga ttatggtaaa      360 gacatcaact ggcagatgtg gccggtaaaa gacaatgaag tacgctggca gttgcaccgt      420
gtaaaatggt ggcaggctat ggccctggtt tatcacgcta cgggcgatga aaaatatgca      480
agagaatggg tatatcagta cagcgattgg gccagaaaaa acccattggg cctgtcgcag      540
gataatgata aatttgtgtg gcggccccctt gaagtgtcgg acagggtaca aagtcttccc      600
ccaaccttca gctatttgt aaactcgcca gcctttaccc cagccttttt aatggaattt      660
ttaaacagtt accaccaaca ggccgattat ttatctacgc attatgccga cagggaaac      720 caccgtttat ttgaagccca acgcaacttg tttgcagggg tatctttccc tgaatttaaa      780
gattcaccaa gatggaggca accggcata tcggtgctga acaccgagat caaaaaacag      840
gtttatgccg atgggatgca gtttgaactt tcaccaattt accatgtagc tgccatcgat      900
atcttcttaa aggcctatgg ttctgcaaaa cgagttaacc ttgaaaaaga atttccgcaa      960
tcttatgtac aaactgtaga aaatatgatt atggcgctga tcagtatttc actgccagat    1020
tataacaccc ctatgtttgg agattcatgg attacagata aaatttcag gatggcacag    1080 tttgccagct gggcccgggt ttttccggca aaccaggcca taaatatttt tgctacagat    1140
ggcaaacaag gtaaggcgcc taactttta tccaaagcat tgagcaatgc aggctttat    1200 acgtttagaa gcggatggga taaaaatgca accgttatgg tattaaaagc cagtcctccc    1260
ggggaatttc atgcccagcc ggataacggg acttttgaac tttttataaa gggcagaaac    1320
tttaccccag acgccggggt atttgtgtat agcggcgacg aagccatcat gaaactgcgg    1380
aactggtacc gtcaaacccg catacacagc acgcttacac tcgacaatca aaatatggtc    1440
attaccaaag cccggcaaaa caatgggaa acaggaaata accttgatgt gcttacctat    1500
accaacccaa gctatccgaa tctggaccat cagcgcagtg tactttttcat caacaaaaaa    1560 tactttctgg tcatcgatag ggcaataggc gaagctaccg gaaacctggg cgtacactgg    1620
cagcttaaag aagacagcaa ccctgttttc gataagacaa agaaccgggt ttacaccact    1680
tacagagatg gtaacaacct gatgatccaa tcgttgaatg cggacaggac cagcctcaat    1740
gaagaagaag gaaaggtatc ttatgtttac aataaggagc tgaaaagacc tgctttcgta    1800
tttgaaaagc ctaaaaagaa tgccggcaca caaaattttg tcagtatagt ttatccatac    1860
gacggccaga aggctccaga gatcagcata cgggaaaaca agggcaatga ttttgagaaa    1920
ggcaagctta atctaaccct taccattaac ggaaaacaac agcttgtgtt ggttccttag    1980

<210> SEQ ID NO 2
<211> LENGTH: 659
<212> TYPE: PRT
<213> ORGANISM: Pedobacter heparinus

<400> SEQUENCE: 2

Met Thr Thr Lys Ile Phe Lys Arg Ile Ile Val Phe Ala Val Ile Ala
1               5                   10                  15
```

-continued

```
Leu Ser Ser Gly Asn Ile Leu Ala Gln Ser Ser Ile Thr Arg Lys
         20                  25                  30
Asp Phe Asp His Ile Asn Leu Glu Tyr Ser Gly Leu Glu Lys Val Asn
             35                  40                  45
Lys Ala Val Ala Ala Gly Asn Tyr Asp Ala Ala Lys Ala Leu Leu
 50                  55                  60
Ala Tyr Tyr Arg Glu Lys Ser Lys Ala Arg Glu Pro Asp Phe Ser Asn
 65                  70                  75                  80
Ala Glu Lys Pro Ala Asp Ile Arg Gln Pro Ile Asp Lys Val Thr Arg
                 85                  90                  95
Glu Met Ala Asp Lys Ala Leu Val His Gln Phe Gln Pro His Lys Gly
                100                 105                 110
Tyr Gly Tyr Phe Asp Tyr Gly Lys Asp Ile Asn Trp Gln Met Trp Pro
             115                 120                 125
Val Lys Asp Asn Glu Val Arg Trp Gln Leu His Arg Val Lys Trp Trp
 130                 135                 140
Gln Ala Met Ala Leu Val Tyr His Ala Thr Gly Asp Glu Lys Tyr Ala
145                 150                 155                 160
Arg Glu Trp Val Tyr Gln Tyr Ser Asp Trp Ala Arg Lys Asn Pro Leu
                165                 170                 175
Gly Leu Ser Gln Asp Asn Asp Lys Phe Val Trp Arg Pro Leu Glu Val
             180                 185                 190
Ser Asp Arg Val Gln Ser Leu Pro Pro Thr Phe Ser Leu Phe Val Asn
         195                 200                 205
Ser Pro Ala Phe Thr Pro Ala Phe Leu Met Glu Phe Leu Asn Ser Tyr
 210                 215                 220
His Gln Gln Ala Asp Tyr Leu Ser Thr His Tyr Ala Glu Gln Gly Asn
225                 230                 235                 240
His Arg Leu Phe Glu Ala Gln Arg Asn Leu Phe Ala Gly Val Ser Phe
                245                 250                 255
Pro Glu Phe Lys Asp Ser Pro Arg Trp Arg Gln Thr Gly Ile Ser Val
             260                 265                 270
Leu Asn Thr Glu Ile Lys Lys Gln Val Tyr Ala Asp Gly Met Gln Phe
         275                 280                 285
Glu Leu Ser Pro Ile Tyr His Val Ala Ala Ile Asp Ile Phe Leu Lys
 290                 295                 300
Ala Tyr Gly Ser Ala Lys Arg Val Asn Leu Glu Lys Glu Phe Pro Gln
305                 310                 315                 320
Ser Tyr Val Gln Thr Val Glu Asn Met Ile Met Ala Leu Ile Ser Ile
                325                 330                 335
Ser Leu Pro Asp Tyr Asn Thr Pro Met Phe Gly Asp Ser Trp Ile Thr
             340                 345                 350
Asp Lys Asn Phe Arg Met Ala Gln Phe Ala Ser Trp Ala Arg Val Phe
         355                 360                 365
Pro Ala Asn Gln Ala Ile Lys Tyr Phe Ala Thr Asp Gly Lys Gln Gly
 370                 375                 380
Lys Ala Pro Asn Phe Leu Ser Lys Ala Leu Ser Asn Ala Gly Phe Tyr
385                 390                 395                 400
Thr Phe Arg Ser Gly Trp Asp Lys Asn Ala Thr Val Met Val Leu Lys
                405                 410                 415
Ala Ser Pro Pro Gly Glu Phe His Ala Gln Pro Asp Asn Gly Thr Phe
             420                 425                 430
Glu Leu Phe Ile Lys Gly Arg Asn Phe Thr Pro Asp Ala Gly Val Phe
```

```
                    435             440             445
Val Tyr Ser Gly Asp Glu Ala Ile Met Lys Leu Arg Asn Trp Tyr Arg
    450                     455                 460

Gln Thr Arg Ile His Ser Thr Leu Thr Leu Asp Asn Gln Asn Met Val
465                     470                 475                 480

Ile Thr Lys Ala Arg Gln Asn Lys Trp Glu Thr Gly Asn Asn Leu Asp
                485                 490                 495

Val Leu Thr Tyr Thr Asn Pro Ser Tyr Pro Asn Leu Asp His Gln Arg
            500                 505                 510

Ser Val Leu Phe Ile Asn Lys Lys Tyr Phe Leu Val Ile Asp Arg Ala
            515                 520                 525

Ile Gly Glu Ala Thr Gly Asn Leu Gly Val His Trp Gln Leu Lys Glu
    530                 535                 540

Asp Ser Asn Pro Val Phe Asp Lys Thr Lys Asn Arg Val Tyr Thr Thr
545                 550                 555                 560

Tyr Arg Asp Gly Asn Asn Leu Met Ile Gln Ser Leu Asn Ala Asp Arg
                565                 570                 575

Thr Ser Leu Asn Glu Glu Glu Gly Lys Val Ser Tyr Val Tyr Asn Lys
            580                 585                 590

Glu Leu Lys Arg Pro Ala Phe Val Phe Glu Lys Pro Lys Lys Asn Ala
        595                 600                 605

Gly Thr Gln Asn Phe Val Ser Ile Val Tyr Pro Tyr Asp Gly Gln Lys
        610                 615                 620

Ala Pro Glu Ile Ser Ile Arg Glu Asn Lys Gly Asn Asp Phe Glu Lys
625                 630                 635                 640

Gly Lys Leu Asn Leu Thr Leu Thr Ile Asn Gly Lys Gln Gln Leu Val
                645                 650                 655

Leu Val Pro

<210> SEQ ID NO 3
<211> LENGTH: 25
<212> TYPE: PRT
<213> ORGANISM: Flavobacterium heparinum

<400> SEQUENCE: 3

Gln Val Tyr Ala Asp Gly Met Gln Phe Glu Leu Ser Pro Ile Tyr His
1               5                   10                  15

Val Ala Ala Ile Asp Ile Phe Leu Lys
                20                  25
```